(12) United States Patent
Jung et al.

(10) Patent No.: US 11,535,629 B2
(45) Date of Patent: Dec. 27, 2022

(54) DIOXOLOISOQUINOLINONE DERIVATIVES AND USE THEREOF

(71) Applicant: HANMI PHARMACEUTICAL CO., LTD., Hwaseong-si (KR)

(72) Inventors: Seung Hyun Jung, Hwaseong-si (KR); Dong Jin Hong, Hwaseong-si (KR); Ji Young Hwang, Hwaseong-si (KR); Seo Hee Kim, Hwaseong-si (KR); So Min Park, Hwaseong-si (KR); Shin Mee Mah, Hwaseong-si (KR); Young Gil Ahn, Hwaseong-si (KR)

(73) Assignee: HANMI PHARMACEUTICAL CO., LTD., Hwaseong-si (KR)

( * ) Notice: Subject to any disclaimer, the term of this patent is extended or adjusted under 35 U.S.C. 154(b) by 0 days.

(21) Appl. No.: 17/605,883

(22) PCT Filed: May 20, 2021

(86) PCT No.: PCT/KR2021/095037
§ 371 (c)(1),
(2) Date: Oct. 22, 2021

(87) PCT Pub. No.: WO2022/035303
PCT Pub. Date: Feb. 17, 2022

(65) Prior Publication Data
US 2022/0275000 A1    Sep. 1, 2022

(30) Foreign Application Priority Data
Aug. 13, 2020 (KR) .................. 10-2020-0102034

(51) Int. Cl.
*C07D 491/056* (2006.01)
*A61P 35/00* (2006.01)

(52) U.S. Cl.
CPC .......... *C07D 491/056* (2013.01); *A61P 35/00* (2018.01)

(58) Field of Classification Search
CPC ............................. C07D 491/056; A61P 35/00
See application file for complete search history.

(56) References Cited

U.S. PATENT DOCUMENTS

| 2015/0175572 A1 | 6/2015 | Edwards et al. |
| 2017/0073335 A1 | 3/2017 | Kanno et al. |

FOREIGN PATENT DOCUMENTS

| KR | 10-2020-0101219 A | 8/2020 | |
| WO | 2013/067302 A1 | 5/2013 | |
| WO | 2019/226491 A1 | 11/2019 | |
| WO | WO 2019/226491 * | 11/2019 | ......... C07D 491/056 |
| WO | 2020/171606 A1 | 8/2020 | |

OTHER PUBLICATIONS

Pei-Pei Kung, et al., "Design and Synthesis of Pyridone-Containing 3,4-Dihydroisoquinoline-1 (2H)-ones as a Novel Class of Enhancer of Zeste Homolog 2 (EZH2) Inhibitors", Journal of Medicinal Chemistry, 2016, pp. 8306-8325, vol. 59, No. 18.
International Search Report for PCT/KR2021/095037 dated Aug. 27, 2021.
Australian IP Office, Full Examination Report dated Jun. 24, 2021 in Australian Application No. 2021203261.

* cited by examiner

*Primary Examiner* — Erich A Leeser
(74) *Attorney, Agent, or Firm* — Sughrue Mion, PLLC

(57) ABSTRACT

Disclosed are novel dioxoisoquinolinone derivative compounds, pharmaceutically acceptable salts thereof, optical isomers, hydrates, and solvates thereof as well as uses thereof. More specifically, the novel dioxoisoquinolinone derivative compounds, pharmaceutically acceptable salts, optical isomers, hydrates, solvates show inhibition activity of EZH1 (Enhancer of zeste homolog 1) and/or EZH2 (Enhancer of zeste homolog 2) activity. Pharmaceutical compositions containing the compound is also disclosed.

15 Claims, No Drawings

DIOXOLOISOQUINOLINONE DERIVATIVES AND USE THEREOF

CROSS REFERENCE TO RELATED APPLICATIONS

This application is a National Stage of International Application No. PCT/KR2021/095037 filed May 20, 2021, claiming priority based on Korean Patent Application No. 10-2020-0102034 filed Aug. 13, 2020.

TECHNICAL FIELD

The present invention relates to novel dioxoisoquinolinone derivative compounds and use thereof. More specifically, the present invention relates to novel dioxoisoquinolinone derivative compounds with inhibition activity of EZH1 (Enhancer of zeste homolog 1) and/or EZH2 (Enhancer of zeste homolog 2) activity, pharmaceutically acceptable salts thereof, and/or pharmaceutical compositions comprising the same.

BACKGROUND ART

A chromosome dynamically controls the replication or transcription of genes by changing its higher-order structure through methylation of DNA, its constituent component, or through various additions or subtractions (acetylation, methylation, phosphorylation, ubiquitination, etc.) of histones (histones H2A, H2B, H3 and H4).

Generally, trimethylation of the fourth lysine from the N-terminal of the histone H3 (H3K4me3) functions to activate transcription, and trimethylation of the 27$^{th}$ lysine (H3K27me3) inhibits transcription, with addition and subtraction carried out by a trithorax complex in the former and by Polycomb Repressive Complex 2 (PRC2) in the latter (Cell 2007, 128, 735-745; Nat. Rev. Cancer 2010, 10, 669-682).

The polycomb gene group are identified as genes which control embryogenesis in drosophilia and these are preserved in chordates (Nat. Rev. Genet. 2007, 8, 9-22). In drosophilia, the enhancer of zeste protein is a catalytic subunit in charge of H3K27 methylation of PRC2, and EZH1 (Enhancer of zeste homolog 1 (*Drosophila*)) and EZH2 (Enhancer of zeste homolog 2 (*Drosophila*)) are together mammalian homologs of drosophilia enhancer of zeste (EMBO J. 1997, 16, 3219-3232; Mamm. Genome. 1999, 10, 311-314). The enzyme activity domains (SET domains) of EZH1 and EZH2 have high homology, and in humans and mice, two types of PRC2 (PRC2-EZH1 and PRC2-EZH2) wherein EZH1 or EZH2 is a catalytic subunit exist (PRC2-EZH1, PRC2-EZH2) (Mol. Cell 2008, 32, 491-502; Mol. Cell 2008, 32, 503-518).

In embryonic stem cells (ES cells), EZH1 and EZH2 function cooperatively or complementarily, and are involved in maintenance of ES cells (Mol. Cell 2008, 32, 491-502). EZH1 and EZH2 are also reported as working cooperatively in the formation and maintenance of hair follicles, and in Merkel cell differentiation (Genes Dev. 2011, 25, 485-498; EMBO J. 2013, 32, 1990-2000; Blood 2011, 118, 6553-6561; Cell Stem Cell 2012, 11, 649-662; Cell Stem Cell 2014, 14, 68-80).

Heightened expression of EZH2 has been reported in a variety of carcinomas including prostate cancer, breast cancer, stomach cancer, lung cancer, ovarian cancer, pancreatic cancer and head & neck cancer, in some of which heightened EZH2 expression is reported to be correlated with poor prognosis (Nature 2002, 419, 624-629; Proc. Natl. Acad. Sci. USA 2003, 100, 11606-11611; Asian Pac. J. Cancer Prev. 2012, 13, 3173-3178; Clin, Cancer Res. 2013, 19, 6556-6565; Cancer Cell 2010, 18, 185-197; Hum. Pathol. 2010, 41, 1205-1209; BMC Cancer 2010, 10, 524; Cancer 2012, 118, 2858-2871; Mutat. Res. 2008, 647, 21-29).

The present inventors, by confirming that novel dioxoisoquinolinone derivative compounds have inhibition activity with regard to EZH1 and/or EZH2, have come to complete the present invention.

DISCLOSURE OF THE INVENTION

Technical Problem

One purpose of the present invention is to provide novel dioxoisoquinolinone derivative compounds having outstanding EZH1 and/or EZH2 inhibition activity.

Another purpose of the present invention is to provide a pharmaceutical composition comprising the above derivatives in a therapeutically effective dose.

Technical Solution

One embodiment of the present invention provides a compound selected from the group consisting of dioxoisoquinolinone derivative compounds of the following Formula 1a or the following Formula 1b, and a pharmaceutically acceptable salt, an optical isomer, a hydrate and a solvate thereof:

[Formula 1a]

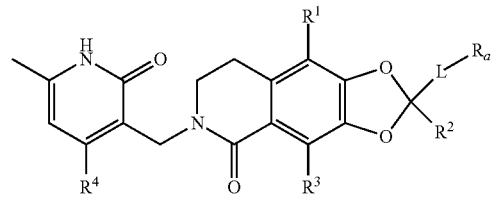

In Formula 1a, $R^1$ is H, halogen, $C_{1-6}$ alkyl, $C_{2-6}$ alkenyl, $C_{2-6}$ alkynyl, $C_{3-6}$ cycloalkyl, $C_{3-6}$ cycloalkenyl, nitrile, aryl, a 5 to 6-membered aromatic heterocyclyl comprising 1 to 3 heteroatoms independently selected from a group comprised of N, O and S, or an aliphatic heterocyclyl including or not including unsaturated bonds in parts of a 5 to 6-membered ring, wherein the ring comprises 1 to 2 heteroatoms selected independently from a group comprised of N, O and S; the $C_{3-6}$ cycloalkyl, $C_{3-6}$ cycloalkenyl, aryl, or a 5 to 6-membered aromatic heterocyclyl comprising 1 to 3 heteroatoms independently selected from a group comprised of N, O and S, or an aliphatic heterocyclyl including or not including unsaturated bonds in parts of a 5 to 6-membered ring, wherein the ring comprises 1 to 2 heteroatoms selected independently from a group comprised of N, O and S, is substituted or unsubstituted by 1 to 3 selected independently from the following group A;

L is a bond or $C_{1-6}$ alkylene;

$R_a$ is a substituted $C_{5-9}$ bicycloalkyl, and the substituted $C_{5-9}$ bicycloalkyl is substituted with $NR^5R^6$, where the $R^5$ and the $R^6$ are each independently H or $C_{1-6}$ alkyl;

$R^2$ is H or $C_{1-6}$ alkyl;

$R^3$ is H, halogen or $C_{1-6}$ alkyl;

$R^4$ is $C_{1-6}$ alkyl, $C_{1-6}$ alkoxy or thio-$C_{1-6}$ alkyl;

Group A comprises halogen, $C_{1-6}$ alkyl, $C_{1-6}$ alkoxy, a 5 to 6-membered aliphatic heterocyclyl whose ring comprises 1 to 2 heteroatoms independently selected from a group comprised of N, O and S, wherein the $C_{1-6}$ alkyl, $C_{1-6}$ alkoxy and a 5 to 6-membered aliphatic heterocyclyl are substituted or unsubstituted with 1 to 3 selected independently from the following Group B;

Group B comprises halogen, $C_{1-6}$ alkyl, $C_{1-6}$ alkoxy, a 5 to 6-membered aliphatic heterocyclyl whose ring comprises 1 to 2 heteroatoms independently selected from a group comprised of N, O and S, wherein the $C_{1-6}$ alkyl, $C_{1-6}$ alkoxy and a 5 to 6-membered aliphatic heterocyclyl are substituted or unsubstituted with 1 to 3 selected independently from the following Group C; and, Group C is halogen, $C_{1-6}$ alkyl, or a 5 to 6-membered aliphatic heterocyclyl whose ring comprises 1 to 2 heteroatoms independently selected from a group comprised of N, O and S.

Another embodiment of the present invention provides a compound selected from the group consisting of dioxoisoquinolinone derivative compounds of the following Formula 1b, a pharmaceutically acceptable salt, an optical isomer, a hydrate and a solvate thereof:

[Formula 1b]

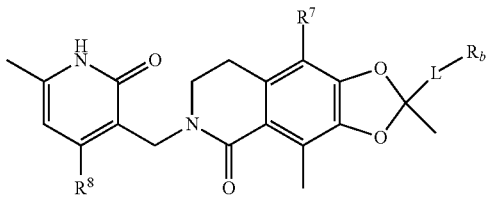

In Formula 1b,
$R_b$ is a substituted cyclohexyl;
$R^7$ is selected from a group comprised of H, furan-2-yl, furan-3-yl, 5-methylfuran-2-yl, thiophen-2-yl, thiophen-3-yl, 5-methylthiophen-2-yl, 1-methyl-1H-pyrazol-4-yl, 1-methyl-1H-pyrrol-2-yl, thiazol-5-yl, 1H-imidazol-1-yl, pyridin-3-yl, pyridin-4-yl, 6-fluoropyridin-3-yl and pyrimidin-5-yl;
L is a bond; and,
$R^8$ is $C_{1-6}$ alkyl, $C_{1-6}$ alkoxy or thio-$C_{1-6}$ alkyl.

According to yet another embodiment of the present invention, a pharmaceutical composition and pharmaceutical formulation for prevention or treatment of the various aforementioned illnesses associated with EZH1 and/or EZH2, the pharmaceutical composition or formulation comprising the above compounds in a therapeutically effective dose.

Benefit(s) of the Invention

The dioxoisoquinolinone derivative represented by Formula 1a or Formula 1b provided by the present invention has outstanding EZH1 and/or EZH2 inhibition activity, accordingly has anti-cancer activity with regard to cancers associated with EZH1, EZH2 or both EZH1 and EZH2 activity, and can be useful as a therapeutic agent therefor.

BEST MODE(S) FOR CARRYING OUT THE INVENTION

Definitions of various terms used to describe the present invention follow. These definitions, unless otherwise limited, shall apply to the present specification in its entirety either individually or as part of terms in which they are included.

The term 'halogen' as used in the present specification, unless mentioned otherwise, refers to fluorine, chlorine, bromine or iodine.

The term 'hydroxy' as used in the present specification, unless mentioned otherwise, refers to an —OH group.

The term 'alkyl' as used in the present specification, unless mentioned otherwise, refers to a saturated, straight chain or branched hydrocarbon radical represented by $C_nH_{2n+1}$, and specifically refers to a saturated, straight chain or branched hydrocarbon radical comprising, respectively, between 1 and 6, between 1 and 8, and between 1 and 10 or between 1 and 20 carbon atoms. Non-limiting examples of such radicals include methyl, ethyl, propyl, isopropyl, n-butyl, t-butyl, neopentyl, n-hexyl, heptyl and oxyl radicals. For example, the term '$C_{1-6}$ alkyl', unless otherwise mentioned, refers to a straight train or branched hydrocarbon residue having a carbon number of 1 to 6. Non-limiting examples of such include methyl, ethyl, propyl, isopropyl, n-butyl, sec-butyl, t-butyl, n-pentyl and n-hexyl.

The term 'alkenyl' as used in the present specification, unless mentioned otherwise, refers to a monovalent group derived from an unsaturated, straight chain or branched hydrocarbon moiety having at least one carbon-carbon double bond, specifically an unsaturated, straight chain or branched monovalent group comprising, respectively, between 2 and 6, between 2 and 8, and between 2 and 10 or between 2 and 20 carbon atoms. Non-limiting examples of these include ethenyl, propenyl, butenyl, 1-methyl-2-buten-1-yl, heptenyl and octenyl radicals.

The term 'alkynyl' as used in the present specification, unless mentioned otherwise, refers to a monovalent group derived from an unsaturated, straight chain or branched hydrocarbon moiety having at least one carbon-carbon triple bond.

The term 'alkoxy' as used in the present specification, unless mentioned otherwise, refers to an oxygen radical represented by $OC_nH_{2n+1}$ and having a monovalent group derived from a saturated, straight chain or branched hydrocarbon moiety comprising, respectively, between 1 and 6, between 1 and 8, and between 1 and 10 or between 1 and 20 carbon atoms. For example, '$C_{1-6}$ alkoxy' refers to, unless otherwise mentioned, refers to an oxygen radical having a straight chain or branched hydrocarbon residue with a carbon number of 1 to 6. Non-limiting examples include methoxy, ethoxy, propoxy, isopropoxy, n-butoxy, sec-butoxy, t-butoxy, pentoxy and hexoxy, etc.

The term 'cycloalkyl' as used in the present specification, unless mentioned otherwise, refers to a monovalent group derived from a saturated monocyclic or partially unsaturated single ring carbocyclic ring compound. For example, the term '$C_{3-7}$ cycloalkyl' used in the present specification, unless otherwise mentioned, refers to a single ring saturated or partially unsaturated hydrocarbon functional group having a carbon number of 3 to 7. Non-limiting examples of a saturated cycloalkyl include cyclopropyl, cyclobutyl, cyclopentyl, cyclohexyl and cycloheptyl, etc.

The term 'heterocyclyl' as used in the present specification, unless mentioned otherwise, refers to a 3 to 7-membered single ring monovalent group comprising 1 to 3 heteroatoms or functional groups selected from among N, O, S, SO and $SO_2$. Non-limiting examples include oxetane-3-yl, tetrahydrofurane-3-yl, tetrahydro-2H-pyran-4-yl, tetrahydro-2H-pyran-3-yl, oxepane-4-yl, oxepane-3-yl, piperidine-1-yl, piperidine-3-yl, piperidine-4-yl, piperazine-1-yl, morpholine-4-yl, thiomorpholine-4-yl, 1,1-dioxide thiomorpholine-4-yl, pyrrolidine-1-yl, pyrroliding-3-yl, azetidine-1-yl, azetidine-3-yl, aziridine-1-yl, azepane-1-yl, azepane-3-yl and azepane-4-yl.

The term 'aryl' as used in the present specification, unless mentioned otherwise, refers to a mono- or poly-cyclic carbocyclic ring system having at least one fused or non-fused aromatic ring, and non-limiting examples of aryls include phenyl, naphthyl, tetrahydronaphthyl, indenyl and anthracenyl, etc.

The term 'heteroaryl' as used in the present specification, unless mentioned otherwise, refers to a monocyclic or bicyclic or higher, 5 to 12-membered, preferably 5 to 7-membered aromatic group comprising at least 1, for example 1 to 4, and preferably 1 to 3 heteroatoms selected from among O, N and S. Non-limiting examples of a monocyclic heteroaryl include thiazolyl, oxazolyl, thiophenyl, furanyl, pyrrolyl, imidazolyl, isooxazolyl, pyrazolyl, triazolyl, thiadiazolyl, tetrazolyl, oxathiazolyl, pyridinyl, pyridazinyl, pyrimidinyl, pyrazinyl and groups similar thereto. Non-limiting examples of a bicylic heteroaryl include indolyl, benzothiophenyl, benzofuranyl, benzimidazolyl, benzoxazolyl, benzisoxazolyl, benzothiazolyl, benzothiadiazolyl, benzotriazolyl, quinolinyl, isoquinolinyl, purinyl, puropyridinyl and groups similar thereto.

The term '$C_{5-9}$ bicycloalkyl' as used in the present specification, unless mentioned otherwise, refers to a group derived from an aliphatic hydrocarbon compound wherein two cycloalkyl rings are sharing two atoms, and may preferably include, but are not limited to, bicyclo [2.1.1] hexyl, bicyclo [2.2.1] heptyl, bicyclo [3.2.1] oxtyl, bicyclo [2.2.2] oxtyl, bicyclo [3.2.2] nonanyl, bicyclo [3.3.1]nonanyl, or bicyclo [3.3.2] decanyl, which may all be substituted or unsubstituted.

The term 'optical isomer' or 'enantiomer' as used in the present specification, unless mentioned otherwise, refers to a pair of stereoisomers which are non-overlapping mirror images of one another, and specifically, a stereoisomer mixture may be a stereoisomer mixture of a compound having an asymmetric carbon atom. More specifically, the compound having an asymmetric carbon atom may be a compound having the structure of the following Formula 1a or the following Formula 1b. Meanwhile, a 1:1 mixture of a pair of enantiomers shall be referred to as a "racemic" mixture.

The term 'asymmetric carbon atom' as used in the present specification, unless mentioned otherwise, refers to a case wherein a carbon atom in a molecule is bonded to four different types of atoms, groups or atoms, or functional groups. A compound comprising such asymmetric carbon atoms has a chiroptical property or an optical isomer.

The term 'enantiomeric excess (ee)' as used in the present specification, unless mentioned otherwise, refers generally to all increases in the ratio of an enantiomer, including not only enantiomeric excesses relative to a racemic mixture but also cases where the ratio of enantiomers (in a racemic mixture) is not 1:1, where the ratio of one enantiomer is greater than that of the other. Specifically, the enantiomeric excess may be one with an optical purity ("% ee") of at least 80%, at least 90%, at least 95%, at least 96%, at least 97%, at least 98% or at least 99%.

The term 'EZH1 and/or EZH2 enzyme activity' as used in the present specification, unless mentioned otherwise, refers to enzymatic activity which introduces a methyl group at the 27th lysine of the histone H3 had by EZH1 and/or EZH2, and 'heightened expression of EZH1 and/or EZH2' means that the amount of expression of the EZH1 protein and/or EZH2 protein is being increased by heightened gene transcription activity, promotion of gene translation, inhibition of protein degradation, or improvement of protein stabilization, etc.

The term 'EZH1 and/or EZH2 has a mutation' as used in the present specification, unless mentioned otherwise, refers to the existence of mutations in the base sequence and/or amino acid sequence of EZH1 and/or EZH2. Examples include somatic mutations (Y641F, Y641N, Y641S, Y641C, A677G and A687V) at the 641st tyrosine, 677th alanine, and 687th alanine of EZH2.

The present invention will be explained in further detail below.

The present invention relates to novel dioxoisoquinolinone derivative compounds and use thereof. More specifically, the present invention relates to novel dioxoisoquinolinone derivative compounds with inhibition activity of EZH1 (Enhancer of zeste homolog 1) and/or EZH2 (Enhancer of zeste homolog 2) activity, pharmaceutically acceptable salts thereof, and/or pharmaceutical compositions comprising the same.

Specifically, one embodiment of the present invention provides a compound selected from among the dioxoisoquinolinone derivative of the following Formula 1a or the following Formula 1b, and pharmaceutically acceptable salts, optical isomers, hydrates and solvates thereof:

[Formula 1a]

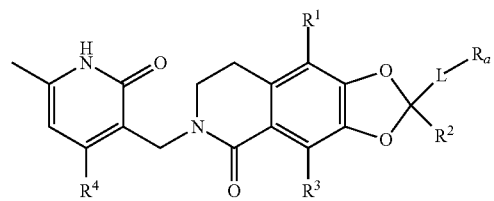

In Formula 1a, $R^1$ is H, halogen, $C_{1-6}$ alkyl, $C_{2-6}$ alkenyl, $C_{2-6}$ alkynyl, $C_{3-6}$ cycloalkyl, $C_{3-6}$ cycloalkenyl, nitrile, aryl, a 5 to 6-membered aromatic heterocyclyl comprising 1 to 3 heteroatoms independently selected from a group comprised of N, O and S, or an aliphatic heterocyclyl including or not including unsaturated bonds in parts of a 5 to 6-membered ring, wherein the ring comprises 1 to 2 heteroatoms selected independently from a group comprised of N, O and S;

The $C_{3-6}$ cycloalkyl, $C_{3-6}$ cycloalkenyl, aryl, or a 5 to 6-membered aromatic heterocyclyl comprising 1 to 3 heteroatoms independently selected from a group comprised of N, O and S, or an aliphatic heterocyclyl including or not including unsaturated bonds in parts of a 5 to 6-membered ring, wherein the ring comprises 1 to 2 heteroatoms selected independently from a group comprised of N, O and S, is substituted or unsubstituted by 1 to 3 selected independently from the following group A;

L is a bond or $C_{1-6}$ alkylene;

$R_a$ is a substituted $C_{5-9}$ bicycloalkyl, and the substituted $C_{5-9}$ bicycloalkyl is substituted with $NR^5R^6$, where the $R^5$ and the $R^6$ are each independently H or $C_{1-6}$ alkyl;

$R^2$ is H or $C_{1-6}$ alkyl;

$R^3$ is H, halogen or $C_{1-6}$ alkyl;

$R^4$ is $C_{1-6}$ alkyl, $C_{1-6}$ alkoxy or thio-$C_{1-6}$ alkyl;

Group A comprises halogen, $C_{1-6}$ alkyl, $C_{1-6}$ alkoxy, a 5 to 6-membered aliphatic heterocyclyl whose ring comprises 1 to 2 heteroatoms independently selected from a group comprised of N, O and S, wherein the $C_{1-6}$ alkyl, $C_{1-6}$ alkoxy and a 5 to 6-membered aliphatic heterocyclyl are substituted or unsubstituted with 1 to 3 selected independently from the following Group B;

Group B comprises halogen, $C_{1-6}$ alkyl, $C_{1-6}$ alkoxy, a 5 to 6-membered aliphatic heterocyclyl whose ring comprises 1 to 2 heteroatoms independently selected from a group comprised of N, O and S, wherein the $C_{1-6}$ alkyl, $C_{1-6}$ alkoxy and a 5 to 6-membered aliphatic heterocyclyl are substituted or unsubstituted with 1 to 3 selected independently from the following Group C; and, Group C is halogen, $C_{1-6}$ alkyl, or a 5 to 6-membered aliphatic heterocyclyl whose ring comprises 1 to 2 heteroatoms independently selected from a group comprised of N, O and S.

Preferably, the compound selected from the group consisting of dioxoisoquinolinone derivative compounds of Formula 1a of the present invention and a pharmaceutically acceptable salt, an optical isomer, a hydrate and a solvate thereof may be a compound where $R_a$ is bicyclo [2.2.2]octyl, and more preferably, the bicyclo [2.2.2] oxyl may be substituted with $NR^5R^6$, where the $R^5$ and $R^6$ are each independently H or $C_{1-6}$ alkyl.

Preferably, the compound selected from the group consisting of dioxoisoquinolinone derivative compounds of Formula 1a of the present invention and a pharmaceutically acceptable salt, an optical isomer, a hydrate and a solvate thereof may be a compound wherein $R^1$ is H, halogen, $C_{1-3}$ alkyl, $C_{2-3}$ alkenyl, $C_{2-3}$ alkynyl, $C_{3-5}$ cycloalkyl or $C_{3-5}$ cycloalkenyl.

Preferably, the compound selected from the group consisting of dioxoisoquinolinone derivative compounds of Formula 1a of the present invention and a pharmaceutically acceptable salt, an optical isomer, a hydrate and a solvate thereof may be a compound wherein $R^2$ is methyl.

Preferably, the compound selected from the group consisting of dioxoisoquinolinone derivative compounds of Formula 1a of the present invention and a pharmaceutically acceptable salt, an optical isomer, a hydrate and a solvate thereof may be a compound wherein $R^3$ is methyl or halogen.

Preferably, the compound selected from the group consisting of dioxoisoquinolinone derivative compounds of Formula 1a of the present invention and a pharmaceutically acceptable salt, an optical isomer, a hydrate and a solvate thereof may be a compound wherein $R^4$ is methyl, propyl, methoxy or thiomethyl.

Further preferable examples of the compound of Formula 1a according to the present invention include, but are not limited to, the following:

9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer A;

9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer B;

9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one;

9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one isomer A;

9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one isomer B;

9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one;

9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one isomer A;

9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one isomer B;

9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer A;

9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer B;

9-cyclopropyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-(cyclopent-1-en-1-yl)-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-cyclopentyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4-dimethyl-9-vinyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-9-ethyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4-dimethyl-9-(prop-1-en-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-9-isopropyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-9-ethyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one isomer A;

6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one isomer B;

2-(4-(dimethylamino)bicyclo[2.2.2]octan-1-yl)-6-((4-methoxy-6-methyl-2-oxo-1,2-dihydropyridin-3-yl)methyl)-2,4,9-trimethyl-7,8-dihydro[1,3]dioxolo[4,5-g]isoquinolin-5(6H)-one;

2-(4-(dimethylamino)bicyclo[2.2.2]octan-1-yl)-2,4,9-trimethyl-6-((6-methyl-2-oxo-4-propyl-1,2-dihydropyridin-3-yl)methyl)-7,8-dihydro[1,3]dioxolo[4,5-g]isoquinolin-5(6H)-one;

4-chloro-6-((4,6-dimethyl-2-oxo-1,2-dihydropyridin-3-yl)methyl)-2-(4-(dimethylamino)bicyclo[2.2.2]octan-1-yl)-2,9-dimethyl-7,8-dihydro-[1,3]dioxolo[4,5-g]isoquinolin-5(6H)-one;

4,9-dichloro-6-((4,6-dimethyl-2-oxo-1,2-dihydropyridin-3-yl)methyl)-2-(4-(dimethylamino)bicyclo[2.2.2]octan-1-yl)-2-methyl-7,8-dihydro-[1,3]dioxolo[4,5-g]isoquinolin-5(6H)-one; and 9-chloro-6-((4,6-dimethyl-2-oxo-1,2-dihydropyridin-3-yl)methyl)-2-(4-(dimethylamino)bicyclo[2.2.2]octan-1-yl)-4-methyl-7,8-dihydro-[1,3]dioxolo[4,5-g]isoquinolin-5(6H)-one.

Specifically, another embodiment of the present invention provides a compound selected from the group consisting of dioxoisoquinolinone derivative compounds of the following Formula 1b, and a pharmaceutically acceptable salt, an optical isomer, a hydrate and a solvate thereof:

[Formula 1b]

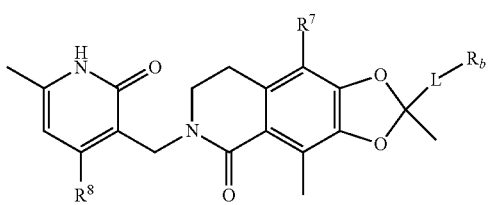

In Formula 1b, $R_b$ is a substituted cyclohexyl;

$R^7$ is selected from a group comprised of H, furan-2-yl, furan-3-yl, 5-methylfuran-2-yl, thiophen-2-yl, thiophen-3-yl, 5-methylthiophen-2-yl, 1-methyl-1H-pyrazol-4-yl, 1-methyl-1H-pyrol-2-yl, thiazol-5-yl, 1H-imidazol-1-yl, pyridin-3-yl, pyridin-4-yl, 6-fluoropyridin-3-yl and pyrimidin-5-yl;

L is a bond; and, $R^8$ is $C_{1-6}$ alkyl, $C_{1-6}$ alkoxy or thio-$C_{1-6}$ alkyl.

Preferable examples of the compound of Formula 1b according to the present invention are, but are not limited to, the following:

(R)-6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one;

(R)-2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one;

(R)-6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one; and, (S)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

Further preferable examples of the compound of Formula 1b of the present invention include, but are not limited to, the following:

6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one;

2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one; and, 6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one.

In the present invention, whereas there is no particular limitation on the method for preparing the compound represented by Formula 1a, said compound may, for example, be synthesized using the preparation method represented by Reaction Formula 1 or Reaction Formula 2 below:

[Reaction Formula 1]

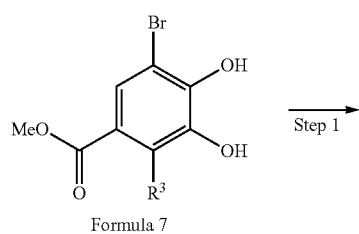

Formula 7

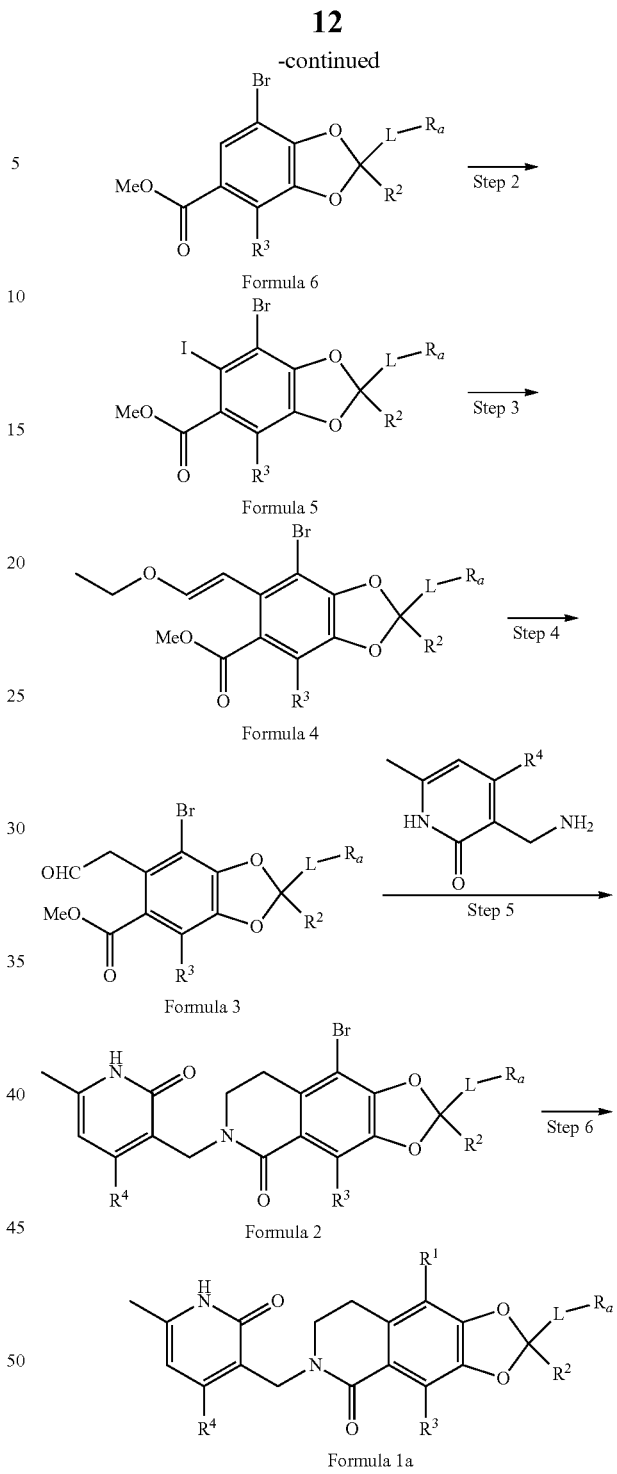

In Reaction Formula 1 above, $R^1$, $R^2$, $R^3$, $R^4$ and $R_a$ are as defined in Formula 1a.

In Reaction Formula 1, the ketalization reaction of Step 1 may be carried out under the conditions set forth in the following literature (Ming Li et. al., J. Org. Chem. 2008, 73, 8658-8660). This is a process wherein the compound of Formula 7 is stirred for 1 to 24 hours under heat in an inert enzyme using equivalent or excess acetylene derivate and 0.01 to 0.03 equivalent parts Ru catalyst to yield the compound of Chemical Equation 6. The iodination reaction of Step 2 is a process wherein iodine and equivalent or surplus silver triofluoroacetate are agitated for 1 to 24 hours at room temperature in a reaction inert solvent to obtain the compound of Formula 5. The Suzuki-Miyaura reaction of Step 3 is a process wherein equivalent or surplus (E)-2-(2-ethoxyvinyl)-4,4,5,5-tetramehyl-1,3,2-dioxaborane and 0.01 to 0.3 equivalents Pd catalyst are agitated for 1 to 24 hours under heat to obtain the compound of Formula 4. The reduction reaction of Step 4 is a process of 0.5 to 24 hours agitation in reaction inert solvent and in the presence of acid under chilling to obtain the compound of Formula 3. The cyclization reaction of Step 5 is a process wherein equivalent or surplus amino alkyl and borohydride in reaction inert solvent are agitated for 1 to 72 hours at room temperature to obtain the compound of Formula 2. The Suzuki-Miyaura reaction of Step 6 is a process wherein equivalent or surplus boronic acid or boronic acid pinacol ester and 0.01 to 0.3 equivalents Pd catalyst are agitated for 1 to 24 hours under heat to obtain the compound of Formula 1a.

hours to obtain the compound of Formula 8. The deprotection reaction of Step 3 is a process wherein the compound of Formula 8, which includes a benzyl group, is agitated with a Pd catalyst in reaction inert solvent in a hydrogen atmosphere for 0.5 to 24 hours to obtain the compound of Formula 1a.

Further, whereas the method for preparing the compound represented by Formula 1b is not particularly limited in the present invention, said compound may, for example, be synthesized using the preparation method of Reaction Formula 3

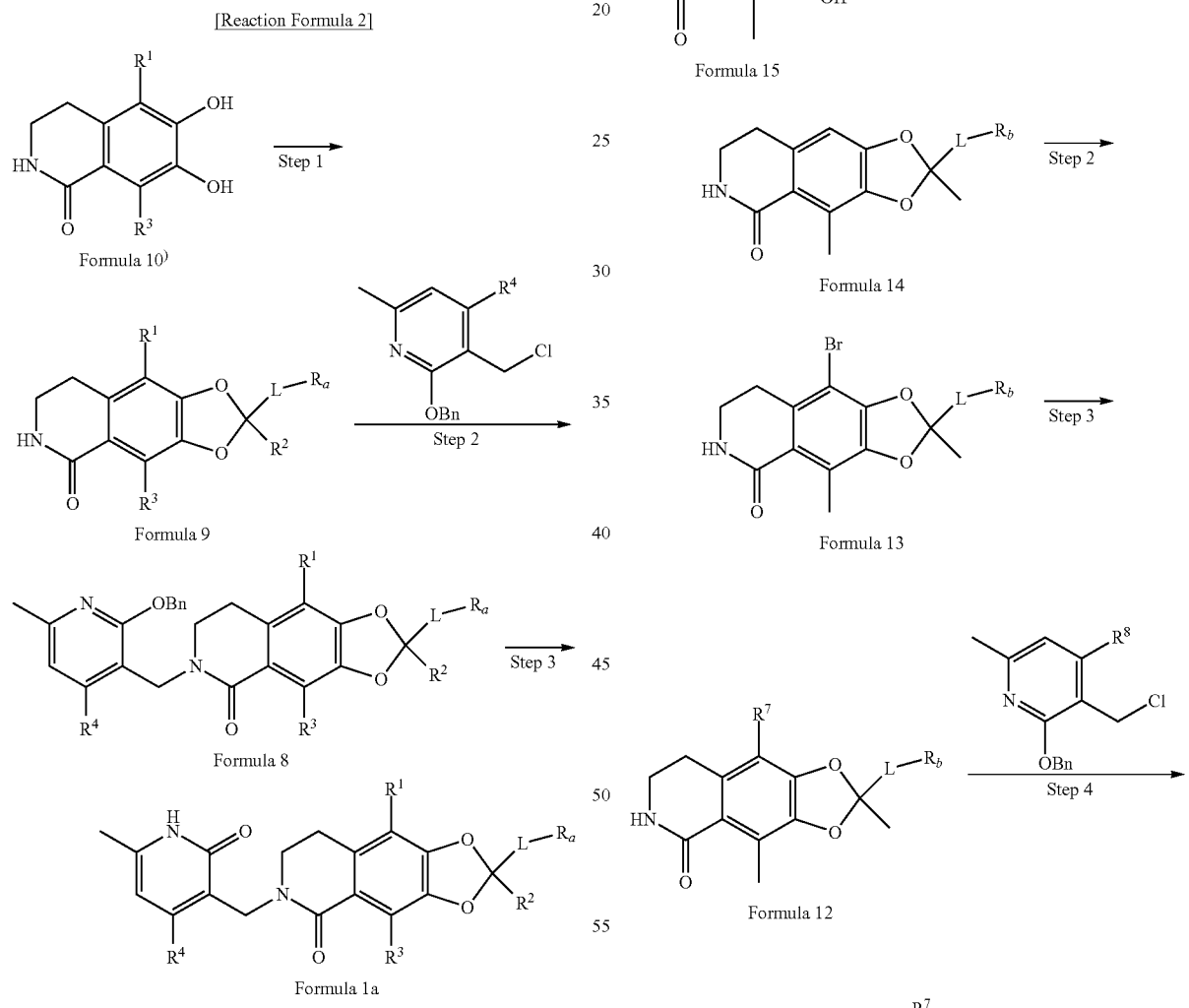

In Reaction Formula 2, $R^1$, $R^2$, $R^3$, $R^4$ and $R_a$ are as defined in Formula 1a.

In Reaction Formula 2, Step 1 is a process wherein the compound of Formula 9 is obtained using the same method as in Step 1 of Reaction Formula 2. The condensation reaction of Step 2 is a process wherein equivalent or surplus alkyl halide and a salt such as potassium t-butoxide in a reaction inert solvent are agitated under chilling for 1 to 24

-continued

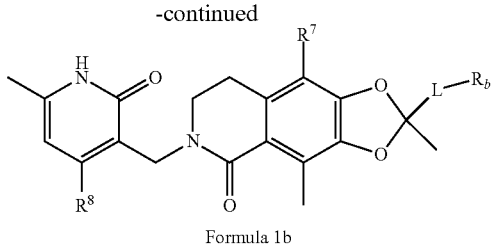

Formula 1b

In Reaction Formula 3, $R^7$, $R^8$, and $R_b$ are as defined in Formula 1b.

In Reaction Formula 3, Step 1 is a process wherein the compound of Formula 14 is obtained using the same method as Step 1 of Reaction Formula 1. The bromination reaction of Step 2 is a process where, in reaction inert solvent, equivalent or surplus N-bromosuccinimide is agitated for 1 to 24 hours under heat to obtain the compound of Formula 13. The Suzuki-Miyaura reaction of Step 3 is a process wherein equivalent or surplus boronic acid or boronic acid pinacol ester and 0.01 to 0.3 equivalents Pd catalyst are agitated for 1 to 24 hours under heat to obtain the compound of Formula 12. The condensation reaction of Step 4 is a process wherein equivalent or surplus alkyl halide and a salt such as potassium t-butoxide in a reaction inert solvent are agitated under chilling for 1 to 24 hours to obtain the compound of Formula 11. The deprotection reaction of Step 5 is a process wherein the compound of Formula 11, which includes a benzyl group, is agitated with a Pd catalyst in reaction inert solvent in a hydrogen atmosphere for 0.5 to 24 hours to obtain the compound of Formula 1b.

The compounds according to the present invention may further form a pharmaceutically acceptable salt. There is no particular limitation on such a pharmaceutically acceptable salt, so long as they are acids which form non-toxic acid addition salts containing pharmaceutically acceptable anions. Examples include acid addition salts formed by inorganic acids such as hydrochloric acid, sulfuric acid, nitric acid, phosphoric acid, hydrobromic acid, and hydroiodic acid; organic carbon acids such as tartaric acid, formic acid, citric acid, acetic acid, trichloroacetic acid, trifluoroacetic acid, gluconic acid, benzoic acid, lactic acid, fumaric acid and maleic acid; and, sulfonic acids such as methane sulfonic acid, benzene sulfonic acid, p-toluene sulfonic acid, and naphthalene sulfonic acid.

Meanwhile, the compounds of the present invention represented by Formula 1a or Formula 1b may have asymmetric carbon centers, thus may exist in the form of different enantiomers. Specifically, the compounds represented by Formula 1a or Formula 1b may exist in the form of all optical isomers and R or S enantiomers, racemic mixtures, diastereomer mixtures, or individual diastereomers, and all such isomers and mixtures thereof are included in the scope of the present invention. Further, the present invention comprises a use for a racemic mixture, one or more enantiomer forms or mixtures thereof, and may comprise isolation methods or preparation processes for isomers known to the art.

In addition, solvate and hydrate forms of Formula 1a and Formula 1b are included in the scope of the present invention.

Another example of the present invention provides a pharmaceutical composition which contains a compound selected from among the compounds of Formula 1a or Formula 1b and a pharmaceutically acceptable salt thereof in a therapeutically effective dose.

The compound represented by Formula 1a or Formula 1b contained in the pharmaceutical composition of the present invention inhibits activity of EZH1 and/or EZH2, and therefore the pharmaceutical composition of the present invention is useful in prevention or treatment of various illnesses associated therewith.

According to another example of the present invention, the pharmaceutical composition is a pharmaceutical composition for prevention or treatment of cancer or tumors which is able to treat by inhibiting EZH1 and/or EZH2 enzyme activity.

According to yet another example of the present invention, a pharmaceutical formulation comprising the above pharmaceutical composition is provided.

The pharmaceutical formulation of the present invention may be in the form of various forms for oral administration such as pills, tablets, powders, capsules, syrups or emulsions, or may be in forms for non-oral administration such as intramuscular, intravenous or subcutaneous injection. Preferably, it may be in a form for oral administration.

Further, the pharmaceutical composition may be formulated using ordinary methods, adding, in addition to the active ingredient, ordinary non-toxic and pharmaceutically acceptable additives, specifically at least one selected from a group comprised of carriers, reinforcing agents and excipients.

Excipients which may be used in the pharmaceutical formulation of the present invention may include, but are not limited to, sweeteners, binders, dissolving agents, solubilizing agents, wettings agents, emulsifiers, isotonic agents, adsorbents, disintegrating agents, antioxidants, preservatives, lubricants, fillers, and aromatics. For example, as excipients, lactose, dextrose, sucrose, mannitol, sorbitol, cellulose, glycine, silica, magnesium aluminum silicate, starch, gelatin, tragacanth gum, alginic acid, sodium alginate, methylcellulose, sodium carboxymethylcellulose, water, ethanol, polyethylene glycol, polyvinyl pyrrolidone, sodium chloride, calcium chloride, orange essence, strawberry essence and vanilla, etc. may be used.

In a case where the pharmaceutical formulation of the present invention is in a form for oral administration, non-limiting examples of carriers which may be used include cellulose, calcium silicate, corn starch, lactose, sucrose, dextrose, calcium phosphate, stearic acid, magnesium stearate, calcium stearate, gelatin, and talc.

In a case where the pharmaceutical formulation of the present invention is in the form of an injection, non-limiting examples of the carrier may include water, saline solution, aqueous glucose solution, similar aqueous sugar solutions, alcohol, glycol, ether, oil, fatty acid, fatty acid ester, and glyceride.

For use of the compound according to the present invention as a drug, the latter is prepared in the form of a pharmaceutical formulation, which comprises, in addition to active ingredient for oral or non-oral administration, pharmaceutically suitable inert organic or inorganic carrier substances, for example water, gelatin, gum Arabic, lactose, starch, plant oils, and polyalkylene glycol, etc. The pharmaceutical formulation may exist in solid form, for example, as tablets, sugar-coated tablets, suppositories or capsules, or in liquid form, for example, as a liquid, a suspension, or an emulsion. Further, these contain, optionally, supplementary agents, for example, preservatives, stabilizers, wetting agents, emulsifying agents, osmoregulatory salts or buffer agents.

In particular, for non-oral administration, injection liquids or suspensions are preferred.

As a carrier system, surfactant supplementary agents, for example bile salts, animal or plant phospholipids, mixtures thereof, liposomes and components thereof may be used.

For oral administration, tablets, sugar-coated tablets or capsules which comprise talc and/or hydrocarbon vehicles or binders, for example lactose or corn or potato starch are suitable. Further, administration is also possible in liquid form, for example in the form of a juice with added sweeteners.

The human dose for the compound of Formula 1a or Formula 1b of the present invention is preferably in a range of 0.1 mg/day to 2,000 mg/day for an adult patient weighing 70 kg. The compound according to the present invention may be administered once a day or divisionally across multiple administrations. Provided, that the administration dose may vary depending on the health, age, body weight, sex, form of administration and severity of illness of a patient, and therefore the scope of the present invention is not limited to the administration dose presented in the above.

According to yet another example of the present invention, a use for a compound selected from among the dioxoisoquinolinone derivative compound of Formula 1a or Formula 1b and a pharmaceutically acceptable salt, an enantiomer, a hydrate and a solvate thereof for treatment of cancer or tumors is provided.

In the following, the present invention will be described in further detail with reference to examples and embodiments. These are intended only to exemplify the present invention, and the scope of the present invention is not limited thereto.

Embodiments

EXAMPLES OF INTERMEDIATE SYNTHESIS

[Intermediate 1] 6,7-dihydroxy-5,8-dimethyl-3,4-dihydroisoquinolin-1(2H)-on

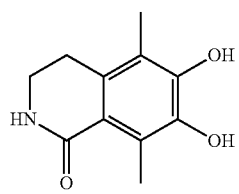

Step 1. Preparation of methyl 3,4-dimethoxy-2,5-dimethylbenzoate

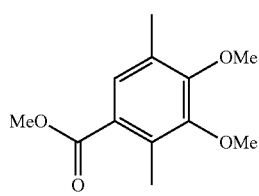 [SMILES: COC(=O)c1cc(C)c(OC)c(OC)c1C]

Methyl 3,4-dihydroxy-2,5-dimethylbenzoate (1.97 g, 10.0 mmol), potassium carbonate (6.94 g, 50.2 mmol) and iodi- methane (1.88 mL, 30.1 mmol) were sequentially added to acetone (20 mL), and the reaction mixture was agitated for 24 hours at room temperature. The reaction product was diluted with ethyl acetate and water, and the organic layer was extracted. The extracted organic layer was dried using anhydrous sodium sulfate, then distilled under vacuum. The product was used without additional purification.

Step 2. Preparation of 3,4-dimethoxy-2,5-dimethylbenzoic acid

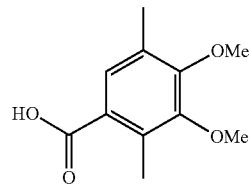

The methyl 3,4-dimethoxy-2,5-dimethylbenzoate (2.25 g, 10.4 mmol) synthesized in [Step 1] above and sodium hydroxide (1.2 g, 30.1 mmol) were added to a methanol/water (1/1, 50 mL) mixture, and the reaction solution was refluxed for 12 hours at 100° C. The reaction solution was chilled to 0° C., then a 6.0N hydrochloric acid solution was used to acidize to approximately pH 1. The solid generated was cold stirred for 1 hour and then collected, rinsed with water and dried to obtain the compound indicated in the title (2.06 g).

Step 3. Preparation of N-(2,2-dimethoxyethyl)-3,4-dimethoxy-2,5-dimethylbenzamide

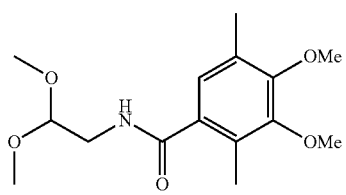 [SMILES: COc1c(C)cc(C(=O)NCC(OC)OC)c(C)c1OC]

The 3,4-dimethoxy-2,5-dimethylbenzoic acid (2.06 g, 9.8 mmol) synthesized in [Step 2] above was added to N,N-dimethylformamide (20 mL), then 1-hydroxybenzotriazole (1.72 g, 12.7 mmol), 1-ethyl-3-(3-dimethylaminopropyl) carbodiimide hydrochloride (2.44 g, 12.7 mmol) and triethylamine (1.78 mL, 12.7 mmol) were added in sequence before agitating for 0.5 hours at room temperature. A mixture of aminoacetaldehyde dimethyl acetal (1.38 mL, 12.7 mmol) and triethylamine (1.78 mL, 12.7 mmol) was added dropwise over approximately 5 minutes, and the mixture was agitated for 12 hours at room temperature. The reaction product was diluted with dichloromethane and water, and the organic layer was extracted. The extracted organic layer was washed with water and salt water and dried using anhydrous sodium sulfate, then distilled in vacuum to obtain the compound indicated in the title, which was used without additional purification.

Step 4. Preparation of 6,7-dihydroxy-5,8-dimethylisoquinolin-1-(2H)-one

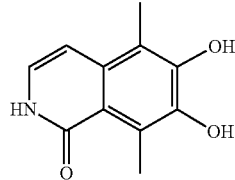

The N-(2,2-dimethoxyethyl)-3,4-dimethoxy-2,5-dimethylbenzamide (2.9 g, 9.8 mmol) synthesized in [Step 3] above was added to concentrated sulfuric acid (15 mL), and the reaction solution was agitated for 24 hours at 60° C. The reaction solution was chilled to room temperature then poured into ice water and agitated for 30 minutes. The generated solid was collected by filtration, washed with surplus water and dried to obtain the compound indicated in the title, which was used without further purification.

Step 5. Preparation of 6,7-dihydroxy-5,8-dimethyl-3,4-dihydroisoquinolin-1-(2H)-one

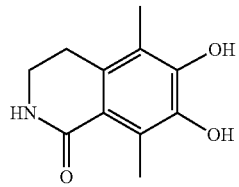

The 6,7-dihydroxy-5,8-dimethylisoquinolin-1-(2H)-one (1.8 g, 8.8 mmol) synthesized in [Step 4] above and 10% palladium/carbon (885 mg) were added to a methanol/ethanol (1/1, 36 mL) mixture, and a hydrogen balloon was installed. The reaction solution was heated to 60° C., agitated for 48 hours, then chilled to room temperature, celite filtered, and vacuum distilled. Dichloromethane was added to the residue and stirred. The solid generated was collected by filtration, rinsed with dichloromethane then dried to obtain the compound indicated in the title (776 mg).

[Intermediate 2] 8-chloro-6,7-dihydroxy-5-methyl-3,4-dihydroisoquinolin-1(2H)-one

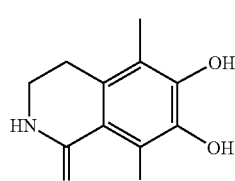

Step 1. Preparation of methyl 5-chloro-3,4-dihydroxy-2-methylbenzoate

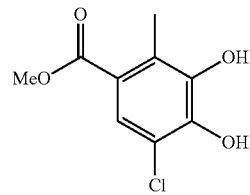

Methyl 3,4-dihydroxy-2-methylbenzoate (2.0 g, 11.0 mmol) was dissolved in ethylacetate (44 mL), and N-chlorosuccinimide (2.2 g, 16.5 mmol) was added. The reaction solution was agitated for 1 hour at room temperature, then p-anisole (1.2 mL, 11.0 mmol) was added. After 15 minutes additional agitation, the reaction product was diluted with ethyl acetate and water, and the organic layer was extracted. The organic layer obtained was dried using sodium sulfate and vacuum distilled. Dichloromethane (5 mL) was added to the residue and agitated for 30 minutes. The solid generated was collected by filtration, then washed with dichloromethane to obtain the compound indicated in the title (1.1 g).

Step 1. Preparation of methyl 5-chloro-3,4-dimethoxy-2-methylbenzoate

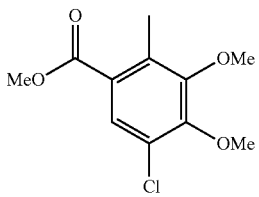 [SMILES: COC(=O)c1cc(Cl)c(OC)c(OC)c1C]

The compound indicated in the title was obtained (2.6 g) by carrying out the same reaction as in [Step 2] of [Intermediate 1], except that instead of methyl 3,4-dihydroxy-2,5-dimethylbenzoate, the methyl 5-chloro-3,4-dihydroxy-2-methylbenzoate prepared in [Step 1] above (2.3 g, 10.6 mmol) was used.

Step 3. Preparation of (5-chloro-3,4-dimethoxy-2-methylphenyl)methanol

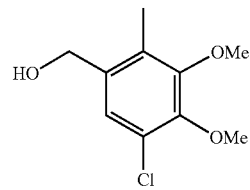

The methyl 5-chloro-3,4-dimethoxy-2-methylbenzoate (2.6 g, 10.63 mmol) synthesized in [Step 2] above was dissolved in tetrahydrofuran (26 mL) and argon substituted, then chilled to 0° C. Lithium aluminum hydride (403 mg, 10.63 mmol) was added to the reaction solution, then agitated for 1 hour at room temperature. The reaction product was chilled to 0° C., then surplus water and 15% sodium hydroxide solution (2.5 mL) was added dropwise. After two more hours agitation at room temperature, celite filtration was performed. The residue was extracted with ethyl acetate, dried with anhydrous sodium sulfate, then vacuum distilled to obtain the compound indicated in the title (2.3 g), which was used without additional purification.

Step 4. Preparation of 1-chloro-5-(chloromethyl)-2,3-dimethoxy-4-methylbenzene

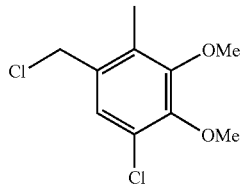

The (5-chloro-3,4-dimethoxy-2-methylphenyl)methanol (2.1 g, 9.69 mmol) synthesized in [Step 3] above was dissolved in ethyl acetate (50 mL), then chilled to 0° C. Thionyl chloride (1.1 mL, 14.53 mmol) was added dropwise to the reaction solution, which was agitated for 1 hour at 0° C. Surplus water was added dropwise to the reaction product, then extraction was performed using ethyl acetate. The organic layer obtained was dried using anhydrous sodium sulfate, then vacuum distilled to obtain the compound indicated in the title (2.3 g), which was used without further purification.

Step 5. Preparation of 2-(5-chloro-3,4-dimethoxy-2-methylphenyl)acetonitrile

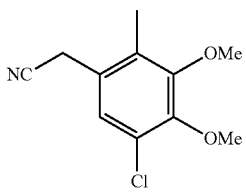

The 1-chloro-5-(chloromethyl)-2,3-dimethoxy-4-methylbenzene (2.3 g, 9.78 mmol) synthesized in [Step 4] above was dissolved in dimethylsulfoxide (23 mL), after which sodium cyanide (576 mg, 11.74 mmol) was added at room temperature. After agitating the reaction solution for 2 hours at room temperature, surplus water was added dropwise to the reaction product which was then extracted with ethyl acetate. The organic layer obtained was dried using anhydrous sodium sulfate, then vacuum distilled to obtain the compound indicated in the title (2.2 g), which was used without further purification.

Step 6. Preparation of 2-(5-chloro-3,4-dimethoxy-2-methylphenyl)ethane-1-amine

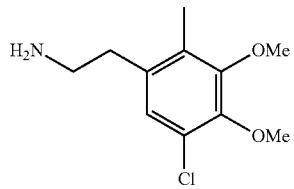

The 2-(5-chloro-3,4-dimethoxy-2-methylphenyl)acetonitrile (2.2 g, 9.75 mmol) synthesized in [Step 5] above and surplus Raney-nickel were dissolved in ethyl acetate (45 mL), and a hydrogen balloon was installed. The reaction solution was agitated for 18 hours at room temperature, celite filtered and vacuum distilled to obtain the compound indicated in the title (2.0 g), which was used without further filtration.

Step 7. Preparation of 4-nitrophenyl(5-chloro-3,4-dimethoxy-2-methylphenetyl)carbamate

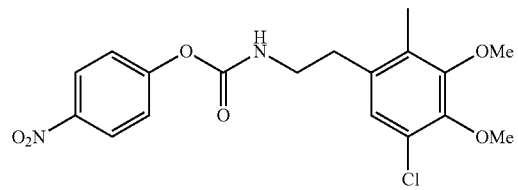 [SMILES: COc1c(Cl)cc(CCNC(=O)Oc2ccc([N+](=O)[O-])cc2)c(C)c1OC]

The 2-(5-chloro-3,4-dimethoxy-2-methylphenyl)ethane-1-amine synthesized in [Step 6] above (2.0 g, 8.71 mmol) and sodium carbonate (2.77 g, 26.12 mmol) were dissolved in 1,2-dichloroethane (40 mL), and 4-nitrophenylchloroformate (2.63 g, 13.06 mmol) was added. After agitating the reaction solution for 18 hours at room temperature, surplus water was added dropwise to the reaction product which was then extracted with dichloromethane. The organic layer obtained was dried using anhydrous sodium sulfate, then vacuum distilled. The residue was purified using silica gel column chromatography to obtain the compound indicated in the title (3.0 g).

Step 8. Preparation of 8-chloro-6,7-dimethoxy-5-methyl-3,4-dihydroisoquinolin-1-(2H)-one

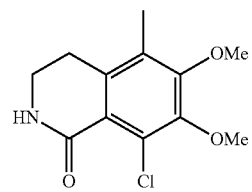 [SMILES: COc1c(C)c2c(c(Cl)c1OC)C(=O)NCC2]

The 4-nitrophenyl(5-chloro-3,4-dimethoxy-2-methylphenetyl)carbamate (3.0 g, 7.60 mmol) synthesized in [Step 7] above was dissolved in 1,2-dichloroethane (50 mL), then chilled to 0° C. Triflic acid (7.3 mL, 81.1 mmol) was slowly added dropwise to the reaction solution, then agitated for 2 hours at 70° C. After chilling the reaction product to room temperature, it was slowly added dropwise to surplus ice water, then agitated for 1 hour until all the ice had melted. The organic layer obtained by dichloromethane extraction was neutralized using a 2N sodium hydroxide aqueous solution. The organic layer was dried using sodium sulfate, and vacuum distilled. The residue was purified using silica gel column chromatography to obtain the compound indicated in the title (1.6 g).

Step 9. Preparation of 8-chloro-6,7-dihydroxy-5-methyl-3,4-dihydroisoquinolin-1(2H)-one

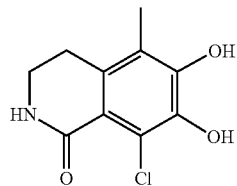

The 8-chloro-6,7-dimethoxy-5-methyl-3,4-dihydroisoquinolin-1-(2H)-one (1.6 g, 6.14 mmol) synthesized in [Step 8] above was added to dichloromethane (20 mL) in a nitrogen atmosphere, and the reaction solution was chilled to 0° C. Tribromo boron (1.3 mL, 13.51 mmol) was added, then slowly brought up to room temperature and agitated for 12 hours. Ice water was added to the reaction solution, and the solid generated was agitated for 1 hour and collected through filtration, then washed with surplus water and dichloromethane and dried to obtain the compound indicated in the title (1.2 g).

[Intermediate 3] 5,8-dichloro-6,7-dihydroxy-3,4-dihydroisoquinolin-1(2H)-one

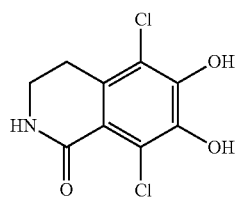

3,4-dihydrobenzoic acid (10.0 g, 64.88 mmol) was added to acetic acid (44 mL), and then sulfuryl chloride (12.6 mL, 155.72 mmol) was added. The reaction solution was heated to 50° C. and agitated for 14 hours. The reaction solution was brought to 0° C., and the generated solid was filtered, and recrystallized using an ethyl acetate/hexane solvent to yield 2,5-dichloro-3,4-dihydrobenzoic acid (4.2 g).

The compound indicated in the title (55 mg) was obtained by repeating up to [Step 9] of [Intermediate 2], except in that in [Step 2] of [Intermediate 2], the 2,5-dichloro-3,4-dihydrobenzoic acid (4.2 g, 18.92 mmol) synthesized above was used instead of methyl 3,4-dihydroxy-2-methylbenzoate.

[Intermediate 4] 6,7-dihydroxy-8-methyl-3,4-dihydroisoquinolin-1(2H)-one

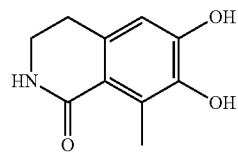

Step 1. Preparation of 7-hydroxy-6-methoxy-8-methylisoquinolin-1(2H)-one

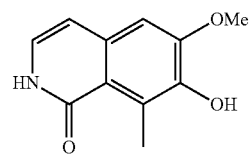

The compound indicated in the title (5.7 g) was obtained by repeating up to [Step 4] of [Intermediate 1], except in that in [Step 1] of [Intermediate 1], methyl 3,4-dihydroxy-2-methylbenzoate was used instead of methyl 3,4-dihydroxy-2,5-dimethylbenzoate.

Step 2. Preparation of 7-hydroxy-6-methoxy-8-methyl-3,4-diydroisoquinolin-1(2H)-one

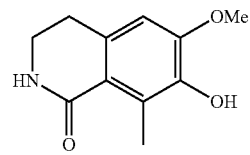

The compound indicated in the title (3.39 g) was obtained by repeating the process of [Intermediate 1], except in that in [Step 5] of [Intermediate 1], the 7-hydroxy-6-methoxy-8-methylisoquinolin-1(2H)-one synthesized in [Step 1] above was used instead of 6,7-dihydroxy-5,8-dimethylisoquinolin-1(2H)-one.

Step 3. Preparation of 6,7-dihydroxy-8-methyl-3,4-dihydroisoquinolin-1(2H)-one

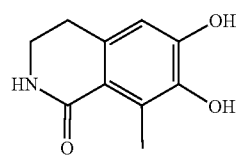

The 7-hydroxy-6-methoxy-8-methyl-3,4-diydroisoquinolin-1(2H)-one (100 mg, 0.482 mmol) synthesized in [Step 2] above was added to dichloromethane (2 mL) in a nitrogen atmosphere, and the reaction solution was chilled to 0° C. A tribromo boron (1 mL, 0.96 mmol, dichloromethane 1M solution) was added thereto, then slowly brought to room temperature and agitated overnight. Ice water was added to the reaction solution, and the solid generated was agitated for 1 hour and collected by filtration. The compound indicated in the title (53 mg) was obtained by washing with surplus water and dichloromethane, then drying.

[Synthesis Example 1] 9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 1]

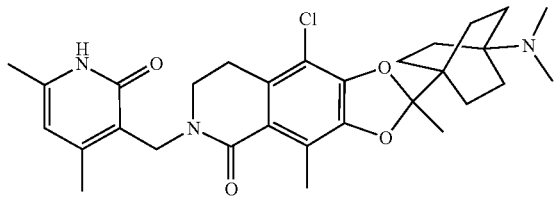

Step 1. Preparation of methyl 2-(4-((t-butoxycarbonyl)amino)bicyclo)[2.2.2]octan-1-yl)-7-chloro-2,4-dimethylbenzo[d][1,3]dioxole-5-carboxylate

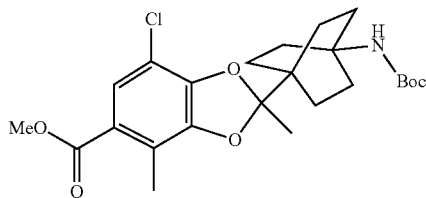 [SMILES: COC(=O)c1cc(Cl)c2c(c1C)OC(C)(C13CCC(NC(=O)OC(C)(C)C)(CC1)CC3)O2]

Methyl 5-chloro-3,4-dihydroxy-2-methylbenzonate (1.5 g, 6.92 mmol), t-butyl (4-ethynylbicyclo[2.2.2]octan-1-yl) carbamate (2.07 g, 8.31 mmol), $Ru_3(CO)_{12}$ (111 mg, 0.173 mmol) and Bippyphos (263 mg, 0.519 mmol) were added to toluene (37.5 mL) and substituted with nitrogen gas, then the mixture was refluxed for 12 hours at 120° C. The reaction solution was chilled to room temperature, then concentrated under vacuum. The residue was purified using silica gel column chromatography to obtain the compound indicated in the title (2.0 g).

Step 2. Preparation of ethyl 2-(4-((t-butoxycarbonyl)amino)bicyclo[2.2.2]octan-1-yl)-7-chloro-6-iodo-2,4-dimethylbenzo[d][1,3]dioxole-5-carboxylate

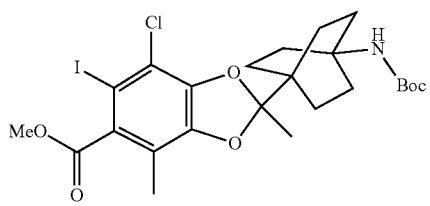 [SMILES: COC(=O)c1c(C)c2c(c(Cl)c1I)OC(C)(C13CCC(NC(=O)OC(C)(C)C)(CC1)CC3)O2]

The methyl 2-(4-((t-butoxycarbonyl)amino)bicyclo)[2.2.2]octan-1-yl)-7-chloro-2,4-dimethylbenzo[d][1,3]dioxole-5-carboxylate (1.85 g, 3.97 mmol) synthesized in [Step 1] above was added to chloroform (18.5 mL). Iodine (2.02 g, 7.97 mmol) and silver trifluoro acetate (1.75 g, 3.97 mmol) were added, and agitated for 4 hours at room temperature. The reaction product was diluted with dichloromethane and sodium thiosulfate aqueous solution, then the organic layer was extracted. The extracted organic layer was washed with salt water, dried using anhydrous sodium sulfate, and vacuum distilled. The residue was purified using basic silica gel column chromatography to obtain the compound indicated in the title (1.7 g).

Step 3. Preparation of methyl (2-(4-aminobicyclo[2.2.2]octan-1-yl)-7-chloro-6-iodo-2,4-dimethyl-benzo[d][1,3]dioxole-5-carboxylate

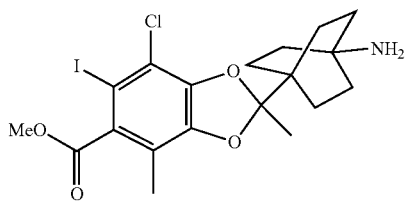 [SMILES: COC(=O)c1c(C)c2c(c(Cl)c1I)OC(C)(C13CCC(N)(CC1)CC3)O2]

The ethyl 2-(4-((t-butoxycarbonyl)amino)bicyclo[2.2.2]octan-1-yl)-7-chloro-6-iodo-2,4-dimethylbenzo[d][1,3]dioxole-5-carboxylate (1.7 g, 2.9 mmol) synthesized in [Step 2] above and trifluoroacetic acid (3.4 mL) were sequentially added to dichloromethane (17 mL), then the reaction solution was agitated for 2 hours at room temperature. After the reaction ended, saturated sodium bicarbonate water was added to neutralize, and extraction was performed using dichloromethane. The extracted organic layer was dried using anhydrous sodium sulfate. The dried organic layer was concentrated under vacuum, and the residue was purified using basic silica gel column chromatography to obtain the compound indicated in the title (1.1 g).

Step 4. Preparation of methyl 7-chloro-2-(4-(dimethylamino)bicyclo[2.2.2]octan-1-yl)-6-iodo-2,4-dimethylbenzo[d][1,3]dioxole-5-carboxylate

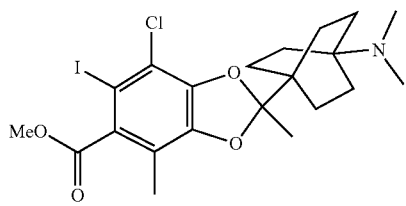 [SMILES: COC(=O)c1c(C)c2c(c(Cl)c1I)OC(C)(C13CCC(N(C)C)(CC1)CC3)O2]

The methyl (2-(4-aminobicyclo[2.2.2]octan-1-yl)-7-chloro-6-iodo-2,4-dimethylbenzo[d][1,3]dioxole-5-carboxylate (1.1 g, 2.2 mmol) synthesized in [Step 3] above and a 37% formaldehyde aqueous solution (0.68 mL, 8.9 mmol) were added sequentially to methanol (22 mL) at 5° C., then agitated for 1 hour at room temperature before adding sodium triacetoxyborohydride (2.84 g, 13 mmol) and agitating for 2 hours at room temperature. After the end of the reaction, saturated calcium carbonate aqueous solution was used to neutralize, and extraction was performed with dichloromethane. The extracted organic layer was washed with saturated sodium chloride aqueous solution, dried using anhydrous sodium sulfate, then vacuum distilled. The residue was purified using basic silica gel column chromatography to obtain the compound indicated in the title (1 g).

Step 5. Preparation of methyl (E)-7-chloro-2-(4-(dimethylamino)bicyclo[2.2.2]octan-1-yl)-6-(2-ethoxyvinyl)-2,4-dimethylbenzo[d][1,3]dioxole-5-carboxylate

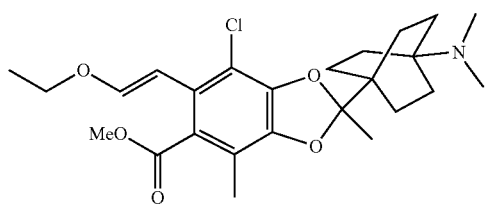 [SMILES: CCO/C=C/c1c(Cl)c2c(c(C)c1C(=O)OC)OC(C)(C13CCC(N(C)C)(CC1)CC3)O2]

The methyl 7-chloro-2-(4-(dimethylamino)bicyclo[2.2.2]octan-1-yl)-6-iodo-2,4-dimethylbenzo[d][1,3]dioxole-5-carboxylate (1 g, 1.9 mmol) synthesized in [Step 4] above, (E)-2-(2-ethoxyvinyl)-4,4,5,5-tetramethyl-1,3,2-dioxaborolan (0.572 g, 2.9 mmol), Tris(dibenzylidineacetone)dipalladium(0) (0.176 g, 0.19 mmol), triphenylphosphine (50 mg, 0.19 mmol) and cesium carbonate (1.25 g, 3.8 mmol) were added to dimethoxy ethane (10 mL). The mixture was nitrogen gas substituted, then reflux agitated for 5 hours at 84° C. After the end of the reaction, filtration was performed using silica sand, followed by washing with saturated sodium chloride aqueous solution. The organic layer was washed with water and saturated sodium chloride aqueous solution, dried using anhydrous sodium sulfate, then concentrated under vacuum. The residue was purified using basic silica gel column chromatography to obtain the compound indicated in the title (900 mg).

Step 6. Preparation of methyl 7-chloro-2-(4-(dimethylamino)bicyclo[2.2.2]octan-1-yl)-2,4-dimethyl-6(2-oxoethyl)benzo[d][1,3]dioxole-5-carboxylate

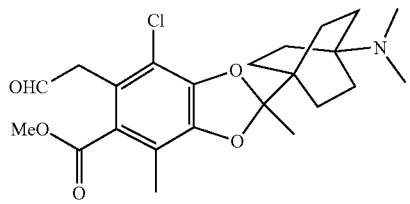 [SMILES: COC(=O)c1c(C)c2c(c(Cl)c1CC=O)OC(C)(C13CCC(N(C)C)(CC1)CC3)O2]

The methyl (E)-7-chloro-2-(4-(dimethylamino)bicyclo[2.2.2]octan-1-yl)-6-(2-ethoxyvinyl)-2,4-dimethylbenzo[d][1,3]dioxole-5-carboxylate (300 mg, 0.65 mmol) synthesized in [Step 5] above was added to dichloromethane (3 mL). Trifluoroacetic acid (0.12 mL, 1.6 mmol) was added at 5° C., followed by 1 hour of agitation. After the end of the reaction, neutralization was performed using saturated sodium bicarbonate water, and extraction was performed using dichloromethane. The extracted organic layer was washed using a saturated sodium chloride aqueous solution. The washed organic layer was dried using anhydrous magnesium sulfate, then concentrated under vacuum. The residue (280 mg) was used in the next reaction without purification.

Step 7. Preparation of 9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one

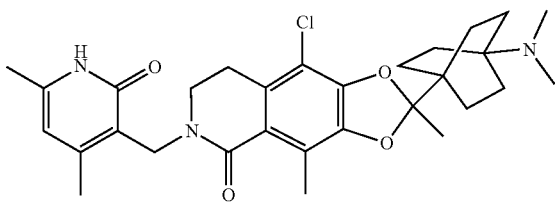

The methyl 7-chloro-2-(4-(dimethylamino)bicyclo[2.2.2]octan-1-yl)-2,4-dimethyl-6(2-oxoethyl)benzo[d][1,3]dioxole-5-carboxylate (280 mg, 0.65 mmol) synthesized in [Step 6] above and 3-(aminomethyl)-4,6-dimethylpyridin-2(1H)-one (118 mg, 0.78 mmol) were added to methanol (3 mL). The reaction mixture was agitated for 1 hour at room temperature. After the reaction ended, sodium borohydride (98 mg, 2.6 mmol) was added, followed by 30 minutes agitation. After 30 minutes, the reaction mixture was brought to room temperature, followed by agitation for 68 hours. After the reaction ended, saturated sodium bicarbonate water was added to neutralize, and extraction was performed using dichloromethane. The extracted organic layer was dried using anhydrous magnesium sulfate, then concentrated under vacuum. The residue was purified using basic silica gel column chromatography to obtain the compound indicated in the title (150 mg).

[Synthesis Example 2] 9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one Isomers A and B [Compound 2 and Compound 3]

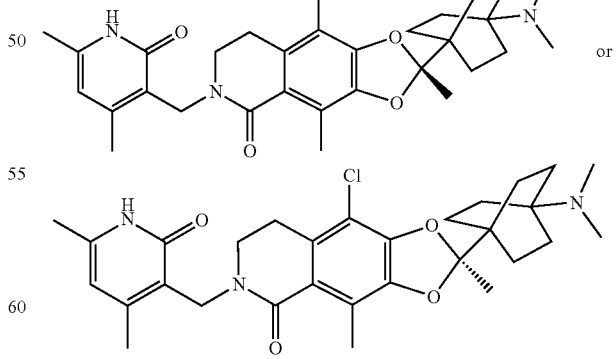

The 9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 1] synthesized in [Synthesis Example 1] was separated into isomers under the following conditions. The absolute stereochemistry of the respective isomers was not measured.
Column: Daicel Chiralcel OZ-H, 10×250 mm
Temperature: 35° C.
Flow rate: 1.8 mL/min
Wavelength: 270 nm
Elution solvent: ethanol:n-hexane:diethylamine=800:200:0.2 (v/v %)
1st peak: 21 minutes—Isomer A (>99.0% ee) [Compound 2]
2nd peak: 27 minutes—Isomer B (>99.0% ee) [Compound 3]

[Synthesis Example 3] 9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one [Compound 4]

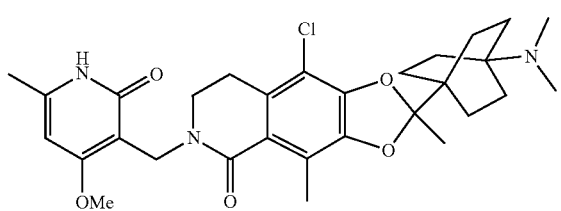

The compound indicated in the title (98 mg) was obtained by carrying out the same reactions as [Synthesis Example 1], except that in [Step 7] of [Synthesis Example 1], instead of 3-(aminomethyl)-4,6-dimethylpyridin-2(1H)-one, 3-(aminomethyl)-4-methoxy-6-methylpyridin-2(1H)-one was used.

[Synthesis Example 4] 9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one Isomers A and B [Compound 5, Compound 6]

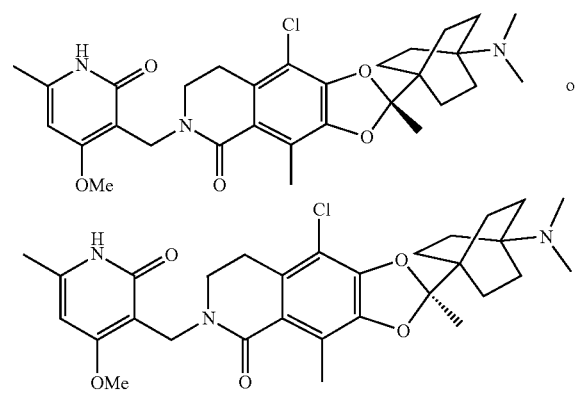

The 9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one synthesized in [Synthesis Example 3] was separated into isomers under the following conditions. The absolute stereochemistry of the respective isomers was not measured.

Column: Daicel Chiralcel OZ-H, 10×250 mm
Temperature: 35° C.
Flow rate: 2.2 mL/min
Wavelength: 270 nm
Elution solvent: ethanol:n-hexane:diethylamine=990:10:1 (v/v %)
1st peak: 50 minutes—Isomer A (>99.0% ee) [Compound 5]
2nd peak: 61 minutes—Isomer B (>99.0% ee) [Compound 6]

[Synthesis Example 5] 9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one [Compound 7]

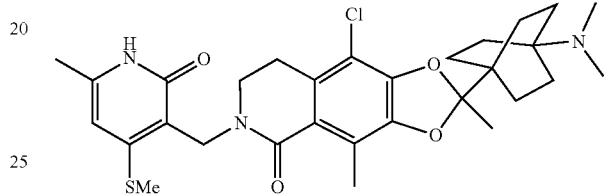

The compound indicated in the title (90 mg) was obtained by carrying out the same reactions as [Synthesis Example 1], except that in [Step 7] of [Synthesis Example 1], instead of 3-(aminomethyl)-4,6-dimethylpyridin-2(1H)-one, 3-(aminomethyl)-6-methyl-4-(methylthio)pyridin-2-(1H)-one was used.

[Synthesis Example 6] 9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one Isomers A and B [Compound 8, Compound 9]

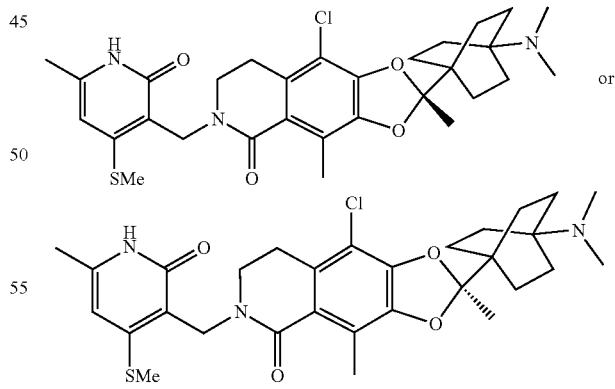

The 9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one synthesized in [Synthesis Example 5] was separated into isomers under the following conditions. The absolute stereochemistry of the respective isomers was not measured.

Column: Daicel Chiralcel OZ-H, 10×250 mm
Temperature: 35° C.
Flow rate: 2.2 mL/min
Wavelength: 270 nm
Elution solvent: ethanol:n-hexane:diethylamine=990:10:1 (v/v %)
$1^{st}$ peak: 49 minutes—Isomer A (>99.0% ee) [Compound 8]
$2^{nd}$ peak: 60 minutes—Isomer B (>99.0% ee) [Compound 9]

[Synthesis Example 7] 9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 10]

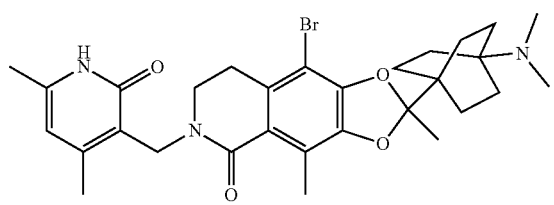

The compound indicated in the title (48 mg) was obtained by carrying out the same reactions as [Synthesis Example 1], except that in [Step 1] of [Synthesis Example 1], instead of methyl 5-chloro-3,4-dihydroxy-2-methylbenzoate, methyl 5-bromo-3,4-dihydroxy-2-methylbenzoate was used.

[Synthesis Example 8] 9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one Isomers A and B [Compound 11, Compound 12]

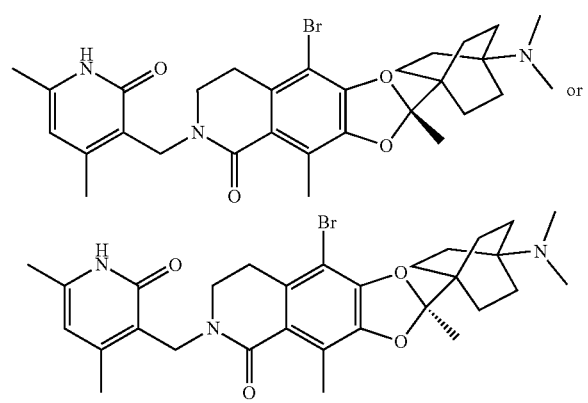

The 9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one synthesized in [Synthesis Example 7] was separated into isomers under the following conditions. The absolute stereochemistry of the respective isomers was not measured.

Column: Daicel Chiralcel OZ-H, 10×250 mm
Temperature: 35° C.
Flow rate: 1.8 mL/min
Wavelength: 270 nm
Elution solvent: ethanol:n-hexane:diethylamine=800:200:0.2 (v/v %)
$1^{st}$ peak: 22 minutes—Isomer A (>99.0% ee) [Compound 11]
$2^{nd}$ peak: 27 minutes—Isomer B (>99.0% ee) [Compound 12]

[Synthesis Example 9] 9-cyclopropyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 13] and 6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 14]

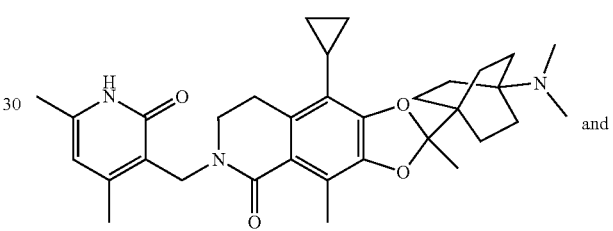

and

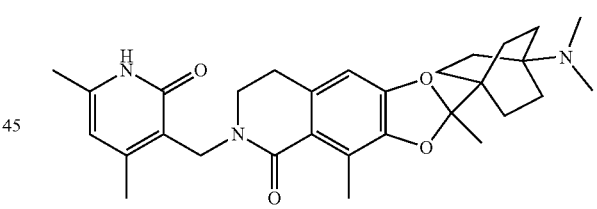

The 9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one synthesized in [Synthesis Example 7] (40 mg, 0.07 mmol, [Compound 10]), cyclopropylboronic acid (29 mg, 0.34 mmol), potassium phosphate (36 mg, 0.17 mmol) and [1,1'-bis(diphenylphosphino)ferrocene]palladium(II)dichloride dichloromethane complex (1:1) (7 mg, 0.01 mmol) were added sequentially to a 1,4-dioxane:water (0.5 mL, 4:1) mixture. After argon gas substitution, the mixture was refluxed for 13 hours at 90° C. After chilling the reaction solution to room temperature, dichloromethane and water were added, and the organic layer was extracted. The extracted organic layer was dried using anhydrous sodium sulfate, then vacuum distilled. The residue was purified using basic silica gel column chromatography to obtain Compound 13 (14 mg) and Compound 14 (8 mg).

[Synthesis Example 10] 9-(cyclopent-1-en-1-yl)-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 15]

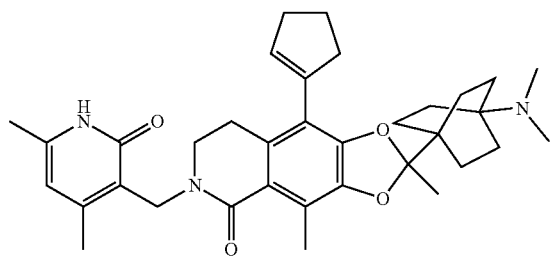

The compound indicated in the title (35 mg) was obtained by carrying out the same reactions as [Synthesis Example 9], except that 1-cyclopentenylboronic acid was used instead of cyclopropylboronic acid in [Synthesis Example 9].

[Synthesis Example 11] 9-cyclopentyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 16]

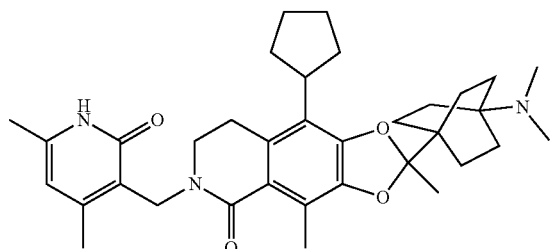

The 9-(cyclopent-1-en-1-yl)-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one synthesized in [Synthesis Example 10] (20 mg, 0.035 mmol) and 10% palladium/carbon (30 mg) were dissolved in ethyl acetate/methanol (1:1, 2 mL), then a hydrogen balloon was installed. The reaction solution was agitated at room temperature for 18 hours, followed by celite filtration and vacuum distillation. The residue was purified using silica gel column chromatography to obtain the compound indicated in the title (9 mg).

[Synthesis Example 12] 6-((4,6-dimethyl-2-oxo-1,2-dihydropyridin-3-yl)methyl)-2-(4-(dimethylamino)bicyclo[2.2.2]octan-1-yl)-2,4-dimethyl-9-vinyl-7,8-dihydro-[1,3]dioxolo[4,5-g]isoquinolin-5(6H)-one [Compound 17]

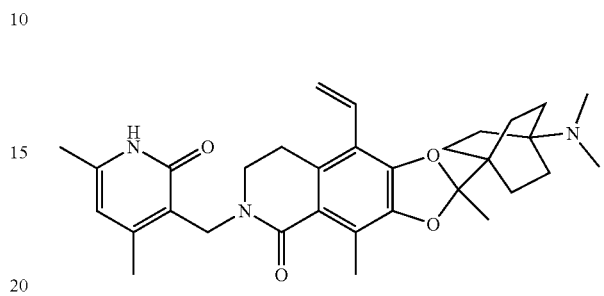

The compound indicated in the title (160 mg) was obtained by carrying out the same reactions as [Synthesis Example 9], except that 4,4,5,5-tetramethyl-2-vinyl-1,3,2-dioxaborolane was used instead of the cyclopropylboronic acid used in [Synthesis Example 9].

[Synthesis Example 13] 6-((4,6-dimethyl-2-oxo-1,2-dihydropyridin-3-yl)methyl)-2-(4-(dimethylamino)bicyclo[2.2.2]octan-1-yl)-9-ethyl-2,4-dimethyl-7,8-dihydro-[1,3]dioxolo[4,5-g]isoquinolin-5(6H)-one [Compound 18]

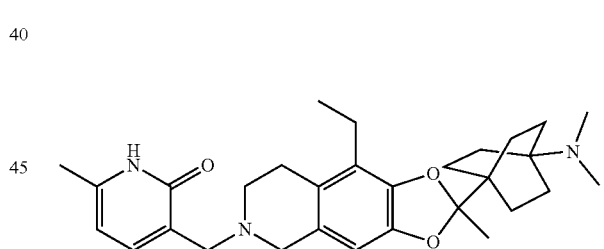

The compound indicated in the title (25.5 mg) was obtained by carrying out the same reactions as [Synthesis Example 11], except that 6-((4,6-dimethyl-2-oxo-1,2-dihydropyridin-3-yl)methyl)-2-(4-(dimethylamino)bicyclo[2.2.2]octan-1-yl)-2,4-dimethyl-9-vinyl-7,8-dihydro-[1,3]dioxolo[4,5-g]isoquinolin-5(6H)-one [Compound 17] was used instead of 9-(cyclopent-1-en-1-yl)-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 15] in [Synthesis Example 11].

[Synthesis Example 14] 6-((4,6-dimethyl-2-oxo-1,2-dihydropyridin-3-yl)methyl)-2-(4-(dimethylamino)bicyclo[2.2.2]octan-1-yl)-2,4-dimethyl-9-(prop-1-en-2-yl)-7,8-dihydro-[1,3]dioxolo[4,5-g]isoquinolin-5(6H)-one [Compound 19]

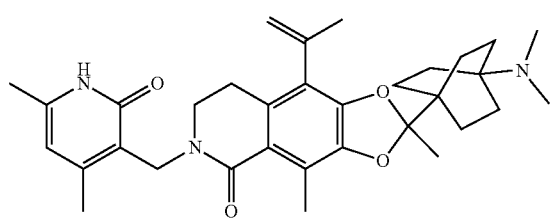

The compound indicated in the title (35 mg) was obtained by carrying out the same reactions as [Synthesis Example 10], except that 2-isopropenylboronic acid pinacol ester was used instead of cyclopropylboronic acid in [Synthesis Example 10].

[Synthesis Example 15] 6-((4,6-dimethyl-2-oxo-1,2-dihydropyridin-3-yl)methyl)-2-(4-(dimethylamino)bicyclo[2.2.2]octan-1-yl)-9-isopropyl-2,4-dimethyl-7,8-dihydro-[1,3]dioxolo[4,5-g]isoquinolin-5(6H)-one [Compound 20]

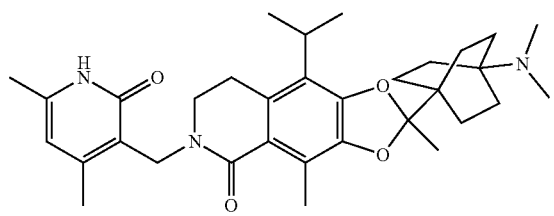

The compound indicated in the title (10 mg) was obtained by carrying out the same reactions as [Synthesis Example 11], except that 6-((4,6-dimethyl-2-oxo-1,2-dihydropyridin-3-yl)methyl)-2-(4-(dimethylamino)bicyclo[2.2.2]octan-1-yl)-2,4-dimethyl-9-(prop-1-en-2-yl)-7,8-dihydro-[1,3]dioxolo[4,5-g]isoquinolin-5(6H)-one [Compound 19] was used instead of 9-(cyclopent-1-en-1-yl)-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one [Compound 15] in [Synthesis Example 11].

[Synthesis Example 16] 6-((4,6-dimethyl-2-oxo-1,2-dihydropyridin-3-yl)methyl)-2-(4-(dimethylamino)bicyclo[2.2.2]octan-1-yl)-9-ethynyl-2,4-dimethyl-7,8-dihydro-[1,3]dioxolo[4,5-g]isoquinolin-5(6H)-one [Compound 21]

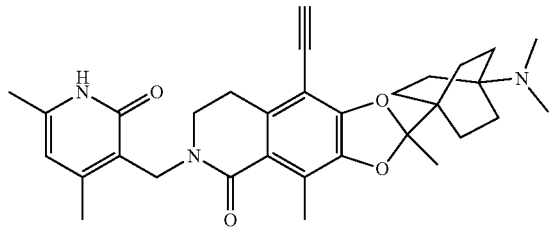

Step 1. Preparation of 6-((4,6-dimethyl-2-oxo-1,2-dihydropyridin-3-yl)methyl)-2-(4-(dimethylamino)bicyclo[2.2.2]octan-1-yl)-2,4-dimethyl-5-oxo-5,6,7,8-tetrahydro-[1,3]dioxolo[4,5-g]isoquinolin-9-carbaldehyde

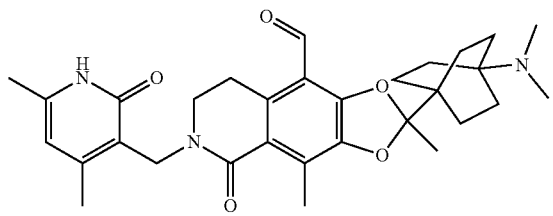

The 6-((4,6-dimethyl-2-oxo-1,2-dihydropyridin-3-yl)methyl)-2-(4-(dimethylamino)bicyclo[2.2.2]octan-1-yl)-2,4-dimethyl-9-vinyl-7,8-dihydro-[1,3]dioxolo[4,5-g]isoquinolin-5(6H)-one synthesized in [Synthesis Example 12] (106 mg, 0.199 mmol, [Compound 17]) was added to a mixture of tetrahydrofuran (2.0 mL) and water (1.0 mL), then 4% osmiumtetroxide (63 ul, 0.01 mmol) and sodium periodate (85 mg, 0.398 mmol) were added in sequence. The reaction solution was agitated for 17 hours at room temperature, and the insoluble solids were removed by filtration. To the filtrate, saturated sodium nitrite was added, and extraction was performed using dichloromethane. The extracted organic layer was dried using anhydrous sodium sulfate, then vacuum distilled to obtain the compound indicated in the title (53 mg).

Step 2. Preparation of 6-((4,6-dimethyl-2-oxo-1,2-dihydropyridin-3-yl)methyl)-2-(4-(dimethylamino)bicyclo[2.2.2]octan-1-yl)-9-ethynyl-2,4-dimethyl-7,8-dihydro-[1,3]dioxolo[4,5-g]isoquinolin-5(6H)-one

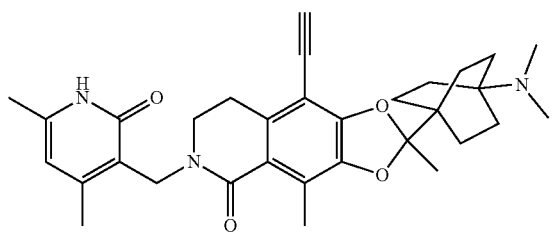

The 6-((4,6-dimethyl-2-oxo-1,2-dihydropyridin-3-yl)methyl)-2-(4-(dimethylamino)bicyclo[2.2.2]octan-1-yl)-2,4-dimethyl-5-oxo-5,6,7,8-tetrahydro-[1,3]dioxolo[4,5-g]isoquinolin-9-carbaldehyde (50 mg, 0.09 mmol) synthesized in [Step 1] above was added to methanol (1.0 mL), and then potassium carbonate (20 mg, 0.149 mmol)dimethyl(1-thiazo-2-oxopropyl)phosphonate (12.3 mg, 0.187 mmol) diluted in dichloromethane (1.0 mL) were added in sequence. The reaction solution was agitated for 16 hours at room temperature and neutralized with saturated ammonium chloride, then saline solution and dichloromethane were added to extract the organic layer. The extracted organic layer was dried using anhydrous sodium sulfate, then vacuum distilled. The residue was purified using basic silica gel column chromatography to obtain the compound indicated in the title (8 mg).

TABLE 1

| Compound No. | Structure / $^1$H-NMR spectrum (300 MHz) | Nomenclature | MS[M + H]$^+$ |
|---|---|---|---|
| 1 | $^1$H-NMR spectrum (300 MHz, CDCl$_3$) δ 5.90 (s, 1H), 4.77 (s, 2H), 3.49 (t, 2H), 2.79 (t, 2H), 2.49 (s, 3H), 2.28 (s, 3H), 2.26 (s, 3H), 2.21 (s, 6H), 1.70-1.59 (m, 12H), 1.53 (s, 3H). | 9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one | 540.3 |
| 2 | $^1$H-NMR spectrum (300 MHz, CDCl$_3$) δ 5.90 (s, 1H), 4.77 (s, 2H), 3.49 (t, 2H), 2.79 (t, 2H), 2.49 (s, 3H), 2.28 (s, 3H), 2.26 (s, 3H), 2.21 (s, 6H), 1.70-1.59 (m, 12H), 1.53 (s, 3H). | 9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer A | 540.3 |
| 3 | $^1$H-NMR spectrum (300 MHz, CDCl$_3$) δ 5.90 (s, 1H), 4.77 (s, 2H), 3.49 (t, 2H), 2.79 (t, 2H), 2.49 (s, 3H), 2.28 (s, 3H), 2.26 (s, 3H), 2.21 (s, 6H), 1.70-1.59 (m, 12H), 1.53 (s, 3H). | 9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer B | 540.3 |
| 4 | $^1$H-NMR spectrum (300 MHz, CDCl$_3$) δ 5.91 (s, 1H), 4.75 (s, 2H), 3.85 (s, 3H), 3.40 (t, 2H), 2.82 (t, 2H), 2.53 (s, 3H), 2.34 (s, 3H), 2.26 (s, 6H), 1.71-1.67 (m, 12H), 1.28 (s, 3H). | 9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one | 556.3 |
| 5 | $^1$H-NMR spectrum (300 MHz, CDCl$_3$) δ 5.91 (s, 1H), 4.75 (s, 2H), 3.85 (s, 3H), 3.40 (t, 2H), 2.82 (t, 2H), 2.53 (s, 3H), 2.34 (s, 3H), 2.26 (s, 6H), 1.71-1.67 (m, 12H), 1.28 (s, 3H). | 9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one isomer A | 556.3 |

TABLE 1-continued

| Compound No. | Structure ¹H-NMR spectrum (300 MHz) | Nomenclature | MS[M + H]⁺ |
|---|---|---|---|
| 6 | | 9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one isomer B | 556.3 |
| | ¹H-NMR spectrum (300 MHz, CDCl₃) δ 5.91 (s, 1H), 4.75 (s, 2H), 3.85 (s, 3H), 3.40 (t, 2H), 2.82 (t, 2H), 2.53 (s, 3H), 2.34 (s, 3H), 2.26 (s, 6H), 1.71-1.67 (m, 12H), 1.28 (s, 3H). | | |
| 7 | | 9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one | 572.2 |
| | ¹H-NMR spectrum (300 MHz, CDCl₃) δ 12.08 (bs, 1H), 5.98 (s, 1H), 4.86 (s, 2H), 3.33 (t, 2H), 2.81 (t, 2H), 2.52 (s, 3H), 2.41 (s, 3H), 2.29 (s, 3H), 2.22 (s, 6H), 1.80-1.70 (m, 6H), 1.70-1.60 (m, 6H), 1.53 (s, 3H). | | |
| 8 | | 9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one isomer A | 572.2 |
| | ¹H-NMR spectrum (300 MHz, CDCl₃) δ 12.08 (bs, 1H), 5.98 (s, 1H), 4.86 (s, 2H), 3.33 (t, 2H), 2.81 (t, 2H), 2.52 (s, 3H), 2.41 (s, 3H), 2.29 (s, 3H), 2.22 (s, 6H), 1.80-1.70 (m, 6H), 1.70-1.60 (m, 6H), 1.53 (s, 3H). | | |
| 9 | | 9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one isomer B | 572.2 |
| | ¹H-NMR spectrum (300 MHz, CDCl₃) δ 12.08 (bs, 1H), 5.98 (s, 1H), 4.86 (s, 2H), 3.33 (t, 2H), 2.81 (t, 2H), 2.52 (s, 3H), 2.41 (s, 3H), 2.29 (s, 3H), 2.22 (s, 6H), 1.80-1.70 (m, 6H), 1.70-1.60 (m, 6H), 1.53 (s, 3H). | | |
| 10 | | 9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one | 584.2 |
| | ¹H-NMR spectrum (300 MHz, CDCl₃) δ 12.13 (brs, 1H), 5.92 (s, 1H), 4.77 (d, 2H), 3.49 (t, 2H), 2.79 (t, 2H), 2.48 (s, 3H), 2.28 (s, 3H), 2.27 (s, 3H), 2.20 (s, 6H), 1.70-1.67 (m, 6H), 1.62-1.58 (m, 6H), 1.53 (s, 3H). | | |
| 11 | | 9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer A | 584.2 |

TABLE 1-continued

| Compound No. | Structure / ¹H-NMR spectrum (300 MHz) | Nomenclature | MS[M + H]⁺ |
|---|---|---|---|
| | ¹H-NMR spectrum (300 MHz, CDCl₃) δ 11.48 (brs, 1H), 5.91 (s, 1H), 4.77 (d, 2H), 3.49 (t, 2H), 2.79 (t, 2H), 2.48 (s, 3H), 2.28 (s, 3H), 2.26 (s, 3H), 2.21 (s, 6H), 1.70-1.67 (m, 6H), 1.62-1.59 (m, 6H), 1.53 (s, 3H). | | |
| 12 | [Structure] | 9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer B | 584.2 |
| | ¹H-NMR spectrum (300 MHz, CDCl₃) δ 11.80 (brs, 1H), 5.91 (s, 1H), 4.77 (d, 2H), 3.49 (t, 2H), 2.79 (t, 2H), 2.48 (s, 3H), 2.28 (s, 3H), 2.27 (s, 3H), 2.20 (s, 6H), 1.70-1.67 (m, 6H), 1.62-1.59 (m, 6H), 1.53 (s, 3H). | | |
| 13 | [Structure] | 9-cyclopropyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one | 546.3 |
| | ¹H-NMR spectrum (300 MHz, CDCl₃) δ 12.18 (br, 1H), 5.91 (s, 1H), 4.79 (s, 2H), 3.47-3.42 (m, 3H), 2.86-2.82 (t, 2H), 2.48 (s, 3H), 2.28 (s, 6H), 2.23 (s, 6H), 1.65-1.50 (m, 12H), 1.45 (s, 3H), 0.87-0.83 (d, 2H), 0.75-0.56 (m, 2H). | | |
| 14 | [Structure] | 6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one | 506.3 |
| | ¹H-NMR spectrum (300 MHz, CDCl₃) δ 2.29 (br, 1H), 6.30 (s, 1H), 5.91 (s, 1H), 4.78 (s, 2H), 3.48-3.42 (t, 2H), 2.73-2.61 (t, 2H), 2.52 (s, 3H), 2.28-2.26 (d, 6H), 2.22 (s, 6H), 1.68-1.58 (m, 12H), 1.46 (s, 3H). | | |
| 15 | [Structure] | 9-(cyclopent-1-en-1-yl)-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one | 572.3 |
| | ¹H-NMR spectrum (300 MHz, CDCl₃) δ 5.91 (s, 1H), 5.61 (s, 1H), 4.79 (d, 2H), 3.38 (m, 2H), 2.69 (m, 2H), 2.50 (s, 3H), 2.41 (m, 2H), 2.29 (s, 3H), 2.26 (s, 3H), 2.22 (s, 6H), 1.97 (m, 2H), 1.85 (m, 2H), 1.65 (m, 6H), 1.62 (m, 6H), 1.47 (s, 3H). | | |
| 16 | [Structure] | 9-cyclopentyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one | 574.4 |
| | ¹H-NMR spectrum (300 MHz, CDCl₃) δ 5.91 (s, 1H), 4.79 (s, 2H), 3.43 (m, 2H), 3.01 (m, 1H), 2.71 (m, 2H), 2.49 (s, 3H), 2.28 (s, 3H), 2.27 (s, 3H), 2.26 (s, 6H), 1.81 (m, 6H), 1.66 (m, 14H), 1.45 (s, 3H). | | |

TABLE 1-continued

| Compound No. | Structure / ¹H-NMR spectrum (300 MHz) | Nomenclature | MS[M + H]⁺ |
|---|---|---|---|
| 17 | ¹H-NMR spectrum (300 MHz, CDCl₃) δ 11.58 (brs, 1H), 6.57 (dd, 1H), 5.90 (s, 1H), 5.82 (dd, 1H), 5.43 (dd, 1H), 4.78 (s, 2H), 3.46 (t, 2H), 2.74 (t, 2H), 2.51 (s, 3H), 2.28 (s, 3H), 2.25 (s, 3H), 2.24 (s, 6H), 1.58-1.78 (m. 12H), 1.50 (s, 3H). | 6-((4,6-dimethyl-2-oxo-1,2-dihydropyridin-3-yl)methyl)-2-(4-(dimethylamino)bicyclo[2.2.2]octan-1-yl)-2,4-dimethyl-9-vinyl-7,8-dihydro-[1,3]dioxolo[4,5-g]isoquinolin-5(6H)-one | 532.3 |
| 18 | ¹H-NMR spectrum (300 MHz, CDCl₃) δ 10.93 (brs, 1H), 5.87 (s, 1H), 4.77 (s, 2H), 3.45 (t, 2H), 2.64 (t, 2H), 2.47 (s, 3H), 2.43-2.52 (q, 2H), 2.27 (s, 3H), 2.23 (s, 6H), 1.53-1.72 (m, 15H), 1.45 (s, 3H), 1.03 (t, 3H). | 6-((4,6-dimethyl-2-oxo-1,2-dihydropyridin-3-yl)methyl)-2-(4-(dimethylamino)bicyclo[2.2.2]octan-1-yl)-9-ethyl-2,4-dimethyl-7,8-dihydro-[1,3]dioxolo[4,5-g]isoquinolin-5(6H)-one | 534.3 |
| 19 | ¹H-NMR spectrum (300 MHz, CDCl₃) δ 5.91 (s, 1H), 5.31-5.30 (m, 1H), 4.83 (s, 1H), 4.81-4.80 (d, 2H), 3.44-3.40 (m, 2H), 2.72-2.68 (m, 2H), 2.53 (s, 3H), 2.31 (s, 3H), 2.27 (s, 3H), 2.24 (s, 6H), 1.98 (s, 3H), 1.69-1.64 (m, 12H), 1.48 (s, 3H). | 6-((4,6-dimethyl-2-oxo-1,2-dihydropyridin-3-yl)methyl)-2-(4-(dimethylamino)bicyclo[2.2.2]octan-1-yl)-2,4-dimethyl-9-(prop-1-en-2-yl)-7,8-dihydro-[1,3]dioxolo[4,5-g]isoquinolin-5(6H)-one | 546.3 |
| 20 | ¹H-NMR spectrum (300 MHz, CDCl₃) δ 5.91 (s, 1H), 4.80 (s, 2H), 3.47-3.44 (m, 2H), 3.02-2.95 (m, 1H), 2.74-2.72 (m, 2H), 2.50 (s, 3H), 2.31 (s, 3H), 2.26 (s, 3H), 2.24 (s, 6H), 1.72-1.63 (m, 18H), 1.48 (s, 3H). | 6-((4,6-dimethyl-2-oxo-1,2-dihydropyridin-3-yl)methyl)-2-(4-(dimethylamino)bicyclo[2.2.2]octan-1-yl)-9-isopropyl-2,4-dimethyl-7,8-dihydro-[1,3]dioxolo[4,5-g]isoquinolin-5(6H)-one | 548.3 |
| 21 | ¹H-NMR spectrum (300 MHz, CDCl₃) δ 12.22 (brs, 1H), 5.92 (s, 1H), 4.78 (d, 2H), 3.48 (t, 2H), 3.36 (s, 1H), 2.87 (t, 2H), 2.52 (s, 3H), 2.28 (s, 3H), 2.27 (s, 3H), 2.22 (s, 6H), 1.71-1.68 (m, 6H), 1.63-1.60 (m, 6H), 1.53 (s, 3H). | 6-((4,6-dimethyl-2-oxo-1,2-dihydropyridin-3-yl)methyl)-2-(4-(dimethylamino)bicyclo[2.2.2]octan-1-yl)-9-ethynyl-2,4-dimethyl-7,8-dihydro-[1,3]dioxolo[4,5-g]isoquinolin-5(6H)-one | 530.3 |

[Synthesis Example 17] 6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one [Compound 22]

Step 1. Preparation of t-butyl(4-(2,4,9-trimethyl-5-oxo-5,6,7,8-tetrahydro-[1,3]dioxolo[4,5-g]isoquinolin-2-yl)bicyclo[2.2.2]octan-1-yl)carbamate

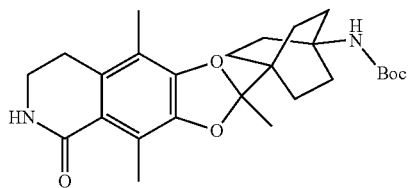 [SMILES: Cc1c2c(c(C)c3c1OC(C)(C14CCC(NC(=O)OC(C)(C)C)(CC1)CC4)O3)C(=O)NCC2]

6,7-dihydroxy-5,8-dimethyl-3,4-dihydroisoquinolin-1(2H)-one (570 mg, 2.77 mmol, [Intermediate 1], t-butyl (4-ethynylbicyclo[2.2.2]octan-1-yl)carbamate (1.38 g, 5.53 mmol), Ru₃(CO)₁₂ (176 mg, 0.277 mmol) and Bippyphos (420 mg, 0.828 mmol) were added to acetonitrile (28 mL), and after argon gas substitution, the mixture was refluxed for 12 hours at 120° C. The reaction solution was chilled to room temperature, then concentrated under vacuum. The residue was purified using silica gel column chromatography to obtain the compound indicated in the title (350 mg).

Step 2. Preparation of t-butyl(4-(6-((2-(benzyloxy)-4,6-dimethylpyridin-3-yl)methyl)-2,4,9-trimethyl-5-oxo-5,6,7,8-tetrahydro-[1,3]dioxolo[4,5-g]isoquinolin-2-yl)bicyclo[2.2.2]octan-1-yl)carbamate

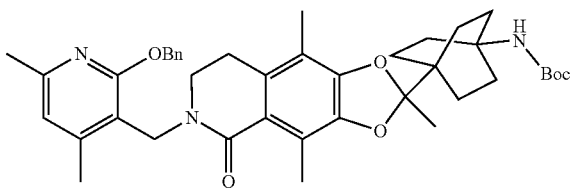 [SMILES: Cc1cc(C)c(CN2CCc3c(C)c4c(c(C)c3C2=O)OC(C)(C23CCC(NC(=O)OC(C)(C)C)(CC2)CC3)O4)c(OCc2ccccc2)n1]

The t-butyl(4-(2,4,9-trimethyl-5-oxo-5,6,7,8-tetrahydro-[1,3]dioxolo[4,5-g]isoquinolin-2-yl)bicyclo[2.2.2]octan-1-yl)carbamate synthesized in [Step 1] above (350 mg, 0.77 mmol) was added to N,N-dimethylformamide (5.0 mL). The reaction solution was chilled to 0° C., then 1.0M potassium t-butoxide (1.0 mL, 0.1 mmol) was added dropwise before agitating for 5 minutes. A solution of 2-(benzyloxy)-3-(chloromethyl)-4,6-dimethylpyridin synthesized using the method stated in WO2014097041 (260 mg, 0.1 mmol) dissolved in tetrahydrofuran (4.0 mL) was added, and the mixture was agitated for 4 hours at 0° C. After the reaction, an ammonium chloride solution was added, and extraction was performed using 10% methanol-chloroform. The extracted organic layer was dried using anhydrous sodium sulfate, then distilled under vacuum. The residue was purified using basic silica gel column chromatography to obtain the compound indicated in the title (320 mg).

Step 3. Preparation of t-butyl (4-(6-((4,6-dimethyl-2-oxo-1,2-dihydropyridin-3-yl)methyl)-2,4,9-trimethyl-5-oxo-5,6,7,8-tetrahydro-[1,3]dioxolo[4,5-g]isoquinolin-2-yl)bicyclo[2.2.2]octan-1-yl)carbamate

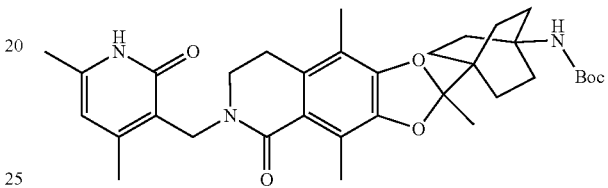

The t-butyl(4-(6-((2-(benzyloxy)-4,6-dimethylpyridin-3-yl)methyl)-2,4,9-trimethyl-5-oxo-5,6,7,8-tetrahydro-[1,3]dioxolo[4,5-g]isoquinolin-2-yl)bicyclo[2.2.2]octan-1-yl)carbamate synthesized in [Step 2] above (319 mg, 0.47 mmol) and 10% palladium/carbon (30 mg) were added to methanol (3 mL) and ethyl acetate (3 mL), then a hydrogen balloon was installed. The reaction solution was agitated for 1 hour at room temperature, celite filtered, then vacuum distilled to obtain the compound indicated in the title (200 mg).

Step 4. Preparation of 2-(4-aminobicyclo[2.2.2]octan-1-yl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one

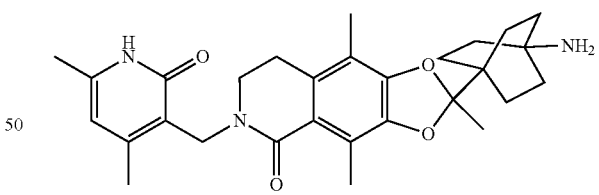

The t-butyl (4-(6-((4,6-dimethyl-2-oxo-1,2-dihydropyridin-3-yl)methyl)-2,4,9-trimethyl-5-oxo-5,6,7,8-tetrahydro-[1,3]dioxolo[4,5-g]isoquinolin-2-yl)bicyclo[2.2.2]octan-1-yl)carbamate synthesized in [Step 3] above (200 mg, 0.34 mmol) and 4N hydrochloric acid-1,4-dioxane solution (1.7 mL) were added sequentially to methanol (1 mL), and the reaction solution was agitated for 1 hour at room temperature. After the reaction, saturated sodium bicarbonate water was added to neutralize, and extraction was performed using 20% methanol-chloroform. The extracted organic layer was dried using anhydrous sodium sulfate, then concentrated under vacuum to obtain the compound indicated in the title (166 mg).

Step 5. Preparation of 6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one

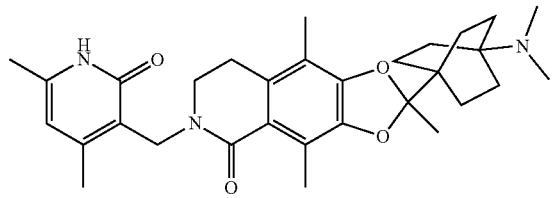

The 2-(4-aminobicyclo[2.2.2]octan-1-yl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one synthesized in [Step 4] above (166 mg, 0.34 mmol) and 37% formaldehyde aqueous solution (0.2 mL, 2.67 mmol) were added in sequence to methanol (3 mL). After 10 minutes agitation at room temperature, sodium triacetoxyborohydride (530 mg, 2.5 mmol) was added, followed by 18 hours agitation at room temperature. After the reaction, neutralization was performed using sodium bicarbonate, followed by extraction using 20% methanol-chloroform. The extracted organic layer was dried using anhydrous sodium sulfate, then concentrated under vacuum. The residue was purified using basic silica gel column chromatography to obtain the compound indicated in the title (168 mg).

[Synthesis Example 18] 6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one Isomers A and B [Compound 23, Compound 24]

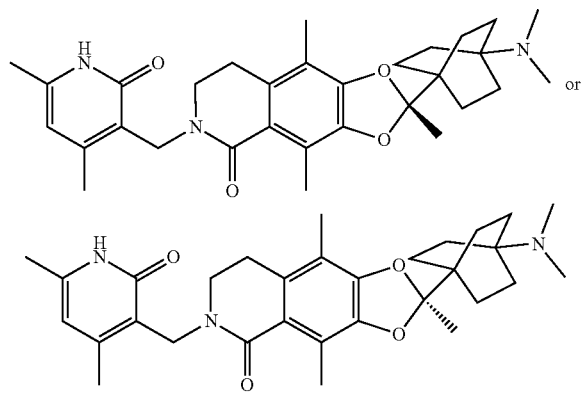

The 6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one synthesized in [Synthesis Example 17] was separated into isomers under the following conditions. The absolute stereochemistry of the respective isomers was not measured.

Column: Daicel Chiralcel OZ-H, 10×250 mm

Temperature: 35° C.

Flow rate: 1.8 mL/min

Wavelength: 270 nm

Elution solvent: ethanol:n-hexane:diethylamine=800:200:0.2 (v/v %)

$1^{st}$ peak: 20 minutes—Isomer A (>99.0% ee) [Compound 23]

$2^{nd}$ peak: 25 minutes—Isomer B (>99.0% ee) [Compound 24]

[Synthesis Example 19] 2-(4-(dimethylamino)bicyclo[2.2.2]octan-1-yl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one [Compound 25]

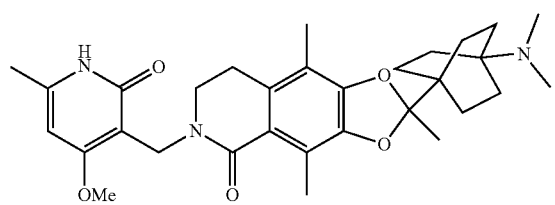

The same reactions were carried out as [Synthesis Example 17], except that in [Step 2] of [Synthesis Example 17], 2-(benzyloxy)-3-(chloromethyl)-4-methoxy-6-methylpyridin was used instead of 2-(benzyloxy)-3-(chloromethyl)-4,6-dimethylpyridin, to obtain the compound indicated in the title (81 mg).

[Synthesis Example 20] 2-(4-(dimethylamino)bicyclo[2.2.2]octan-1-yl)-2,4,9-trimethyl-6-((6-methyl-2-oxo-4-propyl-1,2-dihydropyridin-3-yl)methyl)-7,8-dihydro[1,3]dioxolo[4,5-g]isoquinolin-5(6H)-one [Compound 26]

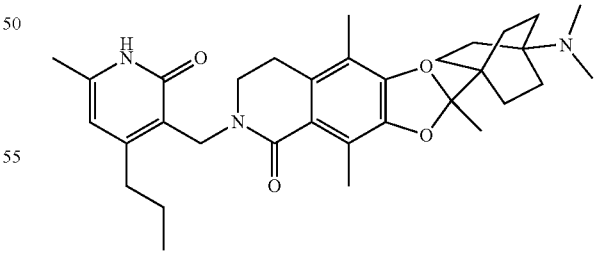

The same reactions were carried out as [Synthesis Example 17], except that in [Step 2] of [Synthesis Example 17], 2-(benzyloxy)-3-(chloromethyl)-6-methyl-4-propylpyridin was used instead of 2-(benzyloxy)-3-(chloromethyl)-4,6-dimethylpyridin, to obtain the compound indicated in the title (11 mg).

TABLE 2

| Compound No. | Structure ¹H-NMR spectrum (300 MHz) | Nomenclature | MS[M + H]⁺ |
|---|---|---|---|
| 22 | | 6-((4,6-dimethyl-2-oxo-1,2-dihydropyridin-3-yl)methyl)-2-(4-(dimethylamino)bicyclo[2.2.2]octan-1-yl )-2,4,9-trimethyl-7,8-dihydro-[1,3]dioxolo[4,5-g]isoquinolin-5(6H)-one | 520.3 |
| | ¹H-NMR spectrum (300 MHz, CDCl₃) δ 12.22 (brs, 1H), 5.91 (s, 1H), 4.79 (d, 2H), 3.44 (t, 2H), 2.61 (t, 2H), 2.50 (s, 3H), 2.28 (s, 3H), 2.27 (s, 3H), 2.20 (s, 6H), 2.03 (s, 3H), 1.69-1.66 (m, 6H), 1.60-1.57 (m, 6H), 1.47 (s, 3H). | | |
| 23 | | 6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one isomer A | 520.3 |
| | ¹H-NMR spectrum (300 MHz, CDCl₃) δ 11.76 (brs, 1H), 5.90 (s, 1H), 4.79 (d, 2H), 3.44 (t, 2H), 2.61 (t, 2H), 2.50 (s, 3H), 2.28 (s, 3H), 2.27 (s, 3H), 2.21 (s, 6H), 2.03 (s, 3H), 1.69-1.61 (m, 6H), 1.59-1.56 (m, 6H), 1.47 (s, 3H). | | |
| 24 | | 6-((4,6-dimethyl-2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one isomer B | 520.3 |
| | ¹H-NMR spectrum (300 MHz, CDCl₃) δ 11.47 (brs, 1H), 5.90 (s, 1H), 4.79 (d, 2H), 3.44 (t, 2H), 2.61 (t, 2H), 2.50 (s, 3H), 2.28 (s, 3H), 2.26 (s, 3H), 2.20 (s, 6H), 2.03 (s, 3H), 1.69-1.66 (m, 6H), 1.60-1.57 (m, 6H), 1.47 (s, 3H). | | |
| 25 | | 2-(4-(dimethylamino)bicyclo[2.2.2]octan-1-yl)-6-((4-methoxy-6-methyl-2-oxo-1,2-dihydropyridin-3-yl)methyl)-2,4,9-trimethyl-7,8-dihydro[1,3]dioxolo[4,5-g]isoquinolin-5(6H)-one | 536.3 |
| | ¹H-NMR spectrum (300 MHz, CDCl₃) δ 12.32 (brs, 1H), 5.88 (s, 1H), 4.75 (d, 2H), 3.82 (s, 3H), 3.35 (t, 2H), 2.62 (t, 2H), 2.51 (s, 3H), 2.31 (s, 3H), 2.22 (s, 6H), 2.03 (s, 3H), 1.69-1.66 (m, 6H), 1.61-1.58 (m, 6H), 1.47 (s, 3H). | | |
| 26 | | 2-(4-(dimethylamino)bicyclo[2.2.2]octan-1-yl)-2,4,9-trimethyl-6-((6-methyl-2-oxo-4-propyl-1,2-Dihydropyridin-3-yl)methyl)-7,8-dihydro[1,3]dioxolo[4,5-g]isoquinolin-5(6H)-one | 548.4 |
| | ¹H-NMR spectrum (300 MHz, CDCl₃) δ 12.16 (brs, 1H), 5.94 (s, 1H), 4.81 (d, 2H), 3.44 (t, 2H), 2.62 (t, 2H), 2.60 (d, 2H), 2.50 (d, 3H), 2.28 (s, 3H), 2.21 (s, 6H), 2.03 (s, 3H), 1.69-1.66 (m, 6H), 1.61-1.58 (m, 6H), 1.55 (t, 2H), 1.53 (s, 3H), 0.95 (t, 3H). | | |

[Synthesis Example 21] 4-chloro-6-((4,6-dimethyl-2-oxo-1,2-dihydropyridin-3-yl)methyl)-2-(4-(dimethylamino)bicyclo[2.2.2]octan-1-yl)-2,9-dimethyl-7,8-dihydro-[1,3]dioxolo[4,5-g]isoquinolin-5(6H)-one [Compound 27]

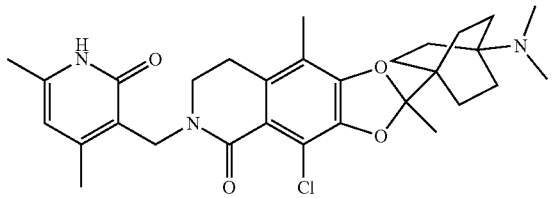

The same reactions were carried out as [Synthesis Example 17], except that in [Step 1] of [Synthesis Example 17], 8-chloro-6,7-dihydroxy-5-methyl-3,4-dihydroisoquinolin-1(2H)-one [Intermediate 2] was used instead of 6,7-dihydroxy-5,8-dimethyl-3,4-dihydroisoquinolin-1(2H)-one, to obtain the compound indicated in the title (76 mg).

[Synthesis Example 22] 4,9-dichloro-6-((4,6-dimethyl-2-oxo-1,2-dihydropyridin-3-yl)methyl)-2-(4-(dimethylamino)bicyclo[2.2.2]octan-1-yl)-2-methyl-7,8-dihydro-[1,3]dioxolo[4,5-g]isoquinolin-5(6H)-one [Compound 28]

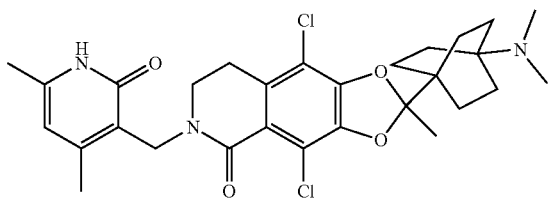

The same reactions were carried out as [Synthesis Example 17], except that in [Step 1] of [Synthesis Example 17], 5,8-dichloro-6,7-dihydroxy-3,4-dihydroisoquinolin-1(2H)-one [Intermediate 3] was used instead of 6,7-dihydroxy-5,8-dimethyl-3,4-dihydroisoquinolin-1(2H)-one, to obtain the compound indicated in the title (10 mg).

[Synthesis Example 23] 9-chloro-6-((4,6-dimethyl-2-oxo-1,2-dihydropyridin-3-yl)methyl)-2-(4-(dimethylamino)bicyclo[2.2.2]octan-1-yl)-4-methyl-7,8-dihydro-[1,3]dioxolo[4,5-g]isoquinolin-5(6H)-one [Compound 29]

Step 1. Preparation of methyl-4-(4-methyl-5-oxo-5,6,7,8-tetrahydro-[1,3]dioxolo[4,5-g]isoquinolin-2-yl)bicyclo[2.2.2]octan-1-carboxylate

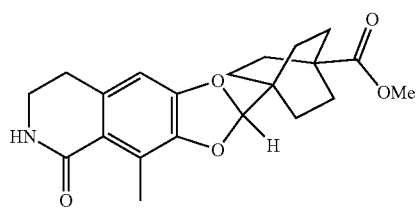 [SMILES: COC(=O)C12CCC(C3Oc4cc5c(c(C)c4O3)C(=O)NCC5)(CC1)CC2]

6,7-dihydroxy-8-methyl-3,4-dihydroisoquinolin-1(2H)-one (600 mg, 3.106 mmol), methyl-4-formylbicyclo[2.2.2]octan-1-carboxylate (914 mg, 4.659 mmol) and 4-methyl-benzenesulfonate monohydroxide (118 mg, 0.621 mmol) were added to toluene (6 mL), and a Dean-Stark trap was used to reflux for 12 hours at 120° C. The reaction solution was chilled to room temperature, then dichloromethane was added. Insoluble solids were filtered out, and the filtrate was concentrated under vacuum. The residue was purified using silica gel column chromatography to obtain the compound indicated in the title (452 mg).

Step 2. Preparation of methyl-4-(9-chloro-4-methyl-5-oxo-5,6,7,8-tetrahydro-[1,3]dioxolo[4,5-g]isoquinolin-2-yl)bicyclo[2.2.2]octan-1-carboxylate

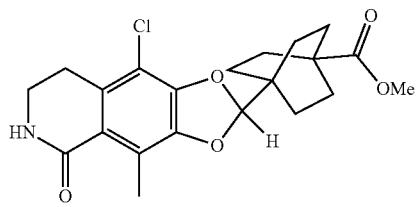 [SMILES: COC(=O)C12CCC(C3Oc4c(C)c5c(c(Cl)c4O3)CCNC5=O)(CC1)CC2]

The methyl-4-(4-methyl-5-oxo-5,6,7,8-tetrahydro-[1,3]dioxolo[4,5-g]isoquinolin-2-yl)bicyclo[2.2.2]octan-1-carboxylate synthesized in [Step 1] above (400 mg, 1.077 mmol) and N-chlorosuccinimide (173 mg, 1.292 mmol) were added in sequence to acetic acid (11 mL). The reaction solution was agitated for 1 hour at 50° C., then chilled to 0° C. Surplus water was added dropwise, and extraction was performed using dichloromethane. The extracted organic layer was washed with salt water, then dried using anhydrous sodium sulfate and vacuum distilled. The residue was purified using silica gel column chromatography to obtain the compound indicated in the title (140 mg).

Step 3. Preparation of 4-(9-chloro-4-methyl-5-oxo-5,6,7,8-tetrahydro-[1,3]dioxolo[4,5-g]isoquinolin-2-yl)bicyclo[2.2.2]octan-1-carboxylate

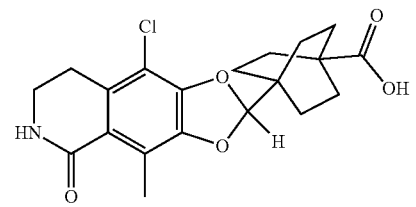 [SMILES: Cc1c2c(c(Cl)c3c1C(=O)NCC3)OC(C13CCC(C(=O)O)(CC1)CC3)O2]

The methyl-4-(9-chloro-4-methyl-5-oxo-5,6,7,8-tetrahydro-[1,3]dioxolo[4,5-g]isoquinolin-2-yl)bicyclo[2.2.2]octan-1-carboxylate synthesized in [Step 2] above (140 mg, 0.345 mmol) and lithium hydroxide monohydrate (58 mg, 1.380 mmol) were added to tetrahydrofuran (2 mL) and water 0.5 mL) in sequence. The reaction solution was agitated for 14 hours at 60° C., then chilled to room temperature after which the tetrahydrofuran was vacuum distilled. The residue was neutralized with 1N hydrochloric acid, then extraction was performed using chloroform and isopropyl alcohol. The organic layer was dried using anhy- Step 4. Preparation of t-butyl-(4-(9-chloro-4-methyl-5-oxo-5,6,7,8-tetrahydro-[1,3]dioxolo[4,5-g]isoquinolin-2-yl)bicyclo[2.2.2]octan-1-yl)carbamate

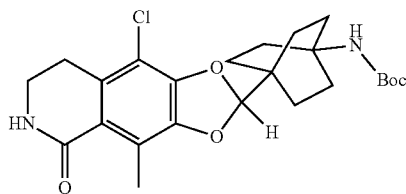 [SMILES: Cc1c2c(c(Cl)c3c1C(=O)NCC3)OC(C13CCC(NC(=O)OC(C)(C)C)(CC1)CC3)O2]

The 4-(9-chloro-4-methyl-5-oxo-5,6,7,8-tetrahydro-[1,3]dioxolo[4,5-g]isoquinolin-2-yl)bicyclo[2.2.2]octan-1-carboxylate synthesized in [Step 3] above (100 mg, 0.255 mmol), diphenylphosphoryl azide (0.07 mL, 0.306 mmol) and triethyl amine (0.04 mL, 0.306 mmol) were added to t-butanol (0.5 mL) and toluene (0.5 mL), then agitated for 30 minutes at room temperature and heated to 80° C. then agitated for 24 hours. The reaction solution was chilled to room temperature, then vacuum distilled. The residue was purified using silica gel column chromatography to obtain the compound indicated in the title (19 mg).

Step 5. Preparation of 9-chloro-6-((4,6-dimethyl-2-oxo-1,2-dihydropyridin-3-yl)methyl)-2-(4-(dimethylamino)bicyclo[2.2.2]octan-1-yl)-4-methyl-7,8-dihydro-[1,3]dioxolo[4,5-g]isoquinolin-5(6H)-one

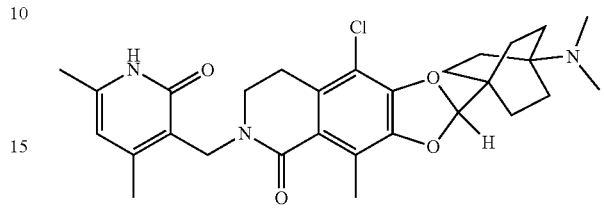

The same reactions were carried out as [Synthesis Example 17], except that in [Step 2] of [Synthesis Example 17], the t-butyl-(4-(9-chloro-4-methyl-5-oxo-5,6,7,8-tetrahydro-[1,3]dioxolo[4,5-g]isoquinolin-2-yl)bicyclo[2.2.2]octan-1-yl)carbamate synthesized in [Step 4] above was used instead of t-butyl(4-(2,4,9-trimethyl-5-oxo-5,6,7,8-tetrahydro-[1,3]dioxolo[4,5-g]isoquinolin-2-yl)bicyclo[2.2.2]octan-1-yl)carbamate, to obtainthe compound indicated in the title (2.8 mg).

TABLE 3

| Compound No. | Structure<br>$^1$H-NMR spectrum (300 MHz) | Nomenclature | MS[M + H]$^+$ |
|---|---|---|---|
| 27 | | 4-chloro-6-((4,6-dimethyl-2-oxo-1,2-dihydropyridin-3-yl)methyl)-2-(4-(dimethylamino)bicyclo[2.2.2]octan-1-yl)-2,9-dimethyl-7,8-dihydro-[1,3]dioxolo[4,5-g]isoquinolin-5(6H)-one | 540.3 |
| | $^1$H-NMR spectrum (300 MHz, CDCl$_3$) δ 11.34 (bs, 1H), 5.9 (s, 1H), 4.76 (s, 2H), 3.53 (t, 2H), 2.63 (t, 2H), 2.33 (s, 3H), 2.26 (s, 3H), 2.23 (s, 6H), 2.04 (s, 3H), 1.57-1.74 (m, 12H), 1.52 (s, 3H). | | |
| 28 | | 4,9-dichloro-6-((4,6-dimethyl-2-oxo-1,2-dihydropyridin-3-yl)methyl)-2-(4-(dimethylamino)bicyclo[2.2.2]Octan-1-yl)-2-methyl-7,8-dihydro-[1,3]dioxolo[4,5-g]isoquinolin-5(6H)-one | 560.2 |
| | $^1$H-NMR spectrum (300 MHz, CDCl$_3$) δ 12.57 (brs, 1H), 5.93 (s, 1H), 4.75 (d, 2H), 3.58 (t, 2H), 2.82 (t, 2H), 2.33 (s, 3H), 2.29 (s, 3H), 2.21 (s, 6H), 1.71-1.68 (m, 6H), 1.63-1.62 (m, 6H), 1.59 (s, 3H). | | |
| 29 | | 9-chloro-6-((4,6-dimethyl-2-oxo-1,2-dihydropyridin-3-yl)methyl)-2-(4-(dimethylamino)bicyclo[2.2.2]octan-1-yl)-4-methyl-7,8-dihydro-[1,3]dioxolo[4,5-g]isoquinolin-5(6H)-one | 526.2 |
| | $^1$H-NMR spectrum (300 MHz, CDCl$_3$) δ 5.92 (s, 1H), 5.81 (s, 1H), 4.76 (s, 2H), 3.49 (m, 2H), 2.80 (m, 2H), 2.51 (s, 3H), 2.29 (s, 3H), 2.27 (s, 3H), 2.25 (s, 6H), 1.65 (s, 12H). | | |

[Synthesis Example 24] (R)-6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one [Compound 30] and (S)-6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one [Compound 31]

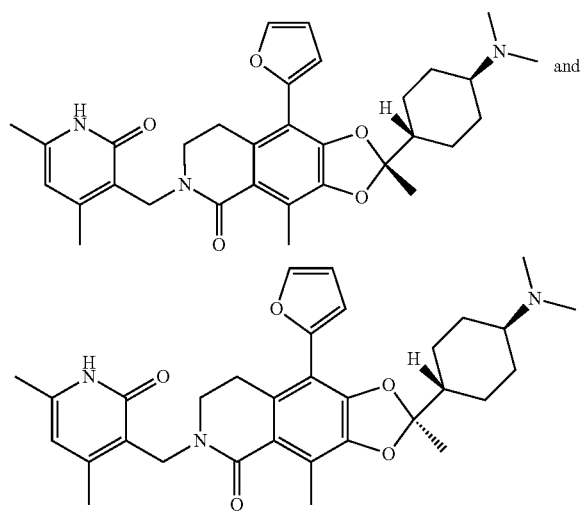

Step 1. Preparation of methyl 3,4-dimethoxy-2-methylbenzoate

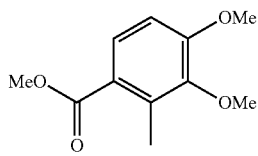

Methyl 3,4-dihydroxy-2-methylbenzoate (20 g, 110 mmol), potassium carbonate (45.6 g, 330 mmol), dimethyl sulfate (26 mL, 270 mmol) and tetrabutylammonium iodide (0.4 mL, 1.1 mmol) were added to acetone (200 mL), and the reaction solution was refluxed for 12 hours at 65° C. The reaction solution was chilled to room temperature, and the solids were filtered out before washing with acetone. The filtrate was vacuum distilled, then used without further purification.

Step 2. Preparation of 3,4-dimethoxy-2-methylbenzoic acid

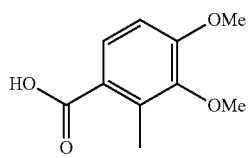

The methyl 3,4-dimethoxy-2-methylbenzoate (23.1 g, 110 mmol) synthesized in [Step 1] above and sodium hydroxide (13.2 g, 330 mmol) were added to a methanol/water (1/1, 300 mL) mixture, and the reaction solution was refluxed for 4 hours at 80° C. The reaction solution was chilled, then acidified to approximately pH 1 using a 6.0N hydrochloric acid aqueous solution. The solid generated was collected through filtration after agitation for 1 hour at low temperature, washed with water, then dried to obtain the compound indicated in the title (21 g), which was used without additional purification.

Step 3. Preparation of N-(2,2-dimethoxyethyl)-3,4-dimethoxy-2-methylbenzamide

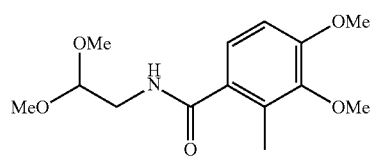 [SMILES: COc1ccc(C(=O)NCC(OC)OC)c(C)c1OC]

The 3,4-dimethoxy-2-methylbenzoic acid synthesized in [Step 2] above (21. g, 107 mmol), 1-hydroxybenzotriazole (18.8 g, 139 mmol), 1-ethyl-3-(3-dimethylaminopropyl)carbodiimide hydrochloride (26.6 g, 139 mmol), aminoacetaldehyde dimethylacetal (15 mL, 139 mmol) and triethylamine (38.7 mL, 278 mmol) were added in sequence to N,N-dimethylformamide (147 mL), and the mixture was agitated for 12 hours at room temperature. The reaction solution was diluted with dichloromethane and water, then the organic layer was extracted. The extracted organic layer was washed with water and salt water, dried using sodium sulfate, vacuum distilled, and used without further purification.

Step 4. Preparation of 7-hydroxy-6-methoxy-8-methylisoquinolin-1(2H)-one

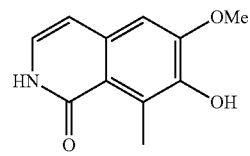

The N-(2,2-dimethoxyethyl)-3,4-dimethoxy-2-methylbenzamide synthesized in [Step 3] above (30.3 g, 107 mmol) was added to concentrated sulfuric acid (140 mL), then agitated for 4 hours at 60° C. The reaction solution was chilled to room temperature, then poured into ice water and agitated for 30 minutes. The generated solid was collected by filtration, washed with surplus water, then dried to obtain the compound indicated in the title (17 g), which was used without further purification.

Step 5. Preparation of 7-hydroxy-6-methoxy-8-methyl-3,4-dihydroisoquinolin-1(2H)-one

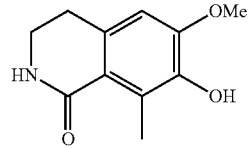

The 7-hydroxy-6-methoxy-8-methylisoquinolin-1(2H)-one synthesized in [Step 4] above (30 g, 0.146 mol) and 10% palladium/carbon (15 g) were added to ethanol (600 mL), and a hydrogen balloon was installed. The reaction solution was agitated for 12 hours at 60° C., then chilled to room temperature, celite filtered, and vacuum distilled to obtain the compound indicated in the title (30 g).

Step 6. Preparation of 6,7-dihydroxy-8-methyl-3,4-dihydroisoquinolin-1(2H)-one

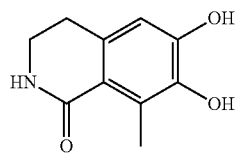

The 7-hydroxy-6-methoxy-8-methyl-3,4-dihydroisoquinolin-1(2H)-one synthesized in [Step 5] above (31.9 g, 0.154 mol) was added to dichloromethane (320 mL) in a nitrogen atmosphere, and the reaction solution was chilled to 0° C. Tribromoboron (37 mL, 0.38 mol) was added, then the reaction solution was slowly heated to room temperature and agitated for 12 hours. Ice water was added to the reaction solution. The solid generated was agitated for 1 hour and collected by filtration, washed using surplus water and dichloromethane, then dried to obtain the compound indicated in the title (21.9 g).

Step 7. Preparation of t-butyl-((trans-4-(2,4-dimethyl-5-oxo-5,6,7,8-tetrahydro-[1,3]dioxolo[4,5-g]isoquinolin-2-yl)cyclohexyl)carbamate

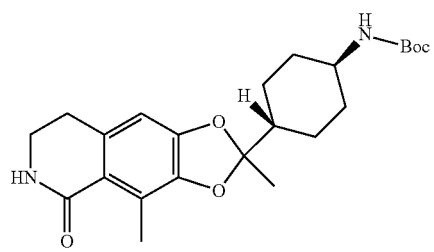 [SMILES: Cc1c2c(cc3c1C(=O)NCC3)OC(C)([C@H]1CC[C@H](NC(=O)OC(C)(C)C)CC1)O2]

The 6,7-dihydroxy-8-methyl-3,4-dihydroisoquinolin-1(2H)-one synthesized in [Step 6] above (7.12 g, 36.85 mmol), t-butyl-(trans-4-ethnylcyclohexyl)carbamate (12.34 g, 55.28 mmol), Ru$_3$(CO)$_{12}$ (1.17 g, 1.84 mmol) and Bippyphos (2.8 g, 5.52 mmol) were added in sequence to acetonitrile (350 mL), argon gas substituted, then refluxed for 17 hours at 130° C. The reaction solution was chilled to room temperature, then concentrated under vacuum. The residue was purified using silica gel column chromatography to obtain the compound indicated in the title (13.4 g).

Step 8. Preparation of t-butyl-((trans-4-(9-bromo-2,4-dimethyl-5-oxo-5,6,7,8-tetrahydro-[1,3]dioxolo[4,5-g]isoquinolin-2-yl)cyclohexyl)carbamate

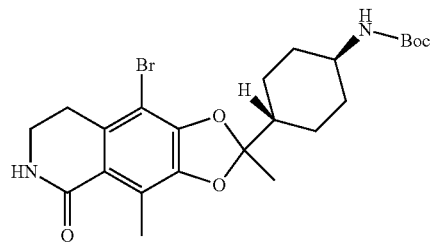 [SMILES: Cc1c2c(c(Br)c3c1C(=O)NCC3)OC(C)([C@H]1CC[C@H](NC(=O)OC(C)(C)C)CC1)O2]

The t-butyl-((trans-4-(2,4-dimethyl-5-oxo-5,6,7,8-tetrahydro-[1,3]dioxolo[4,5-g]isoquinolin-2-yl)cyclohexyl)carbamate synthesized in [Step 7] above (48.7 g, 0.117 mmol) was added to acetonitrile (550 mL), followed by addition of N-bromosuccinimide (25.0 g, 0.14 mmol). The reaction solution was agitated for 12 hours at room temperature, followed by addition of saturated sodium thiosulfate and extraction using ethyl acetate. The extracted organic layer was dried using anhydrous sodium sulfate, then vacuum distilled. The residue was purified using silica gel column chromatography to obtain the compound indicated in the title (38.7 g).

Step 9. Preparation of t-butyl-((trans-4-(9-(furan-2-yl)-2,4-dimethyl-5-oxo-5,6,7,8-tetrahydro-[1,3]dioxolo[4,5-g]isoquinolin-2-yl)cyclohexyl)carbamate

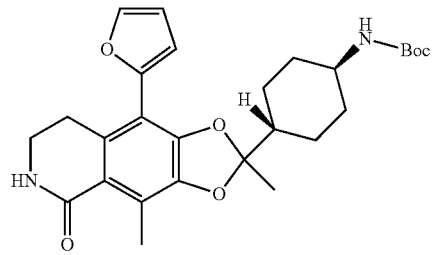 [SMILES: Cc1c2c(c(-c3ccco3)c3c1C(=O)NCC3)OC(C)([C@H]1CC[C@H](NC(=O)OC(C)(C)C)CC1)O2]

The t-butyl-((trans-4-(9-bromo-2,4-dimethyl-5-oxo-5,6,7,8-tetrahydro-[1,3]dioxolo[4,5-g]isoquinolin-2-yl)cyclohexyl)carbamate synthesized in [Step 8] above (0.3 g, 0.606 mmol), furan-2-boronic acid (280 mg, 3.028 mmol), 1,1'-bis(diphenylphosphino)ferrocene-palladium(II)dichloride. dichloromethane complex (115 mg, 0.1 mmol) and potassium carbonate (420 mg, 3.028 mmol) were added to 1,4-dioxane (20 mL) and water (5 mL), argon gas substituted, then refluxed for 15 hours at 100° C. The reaction solution was chilled to room temperature, then concentrated under vacuum. The residue was purified using silica gel column chromatography to obtain the compound indicated in the title (180 mg).

Step 10. Preparation of t-butyl-(trans-4-(6-((2-(benzyloxy)-4,6-dimethylpyridin-3-yl)methyl)-9-(furan-2-yl)-2,4-dimethyl-5-oxo-5,6,7,8-tetrahydro-[1,3]dioxolo[4,5-g]isoquinolin-2-yl)cyclohexyl)carbamate

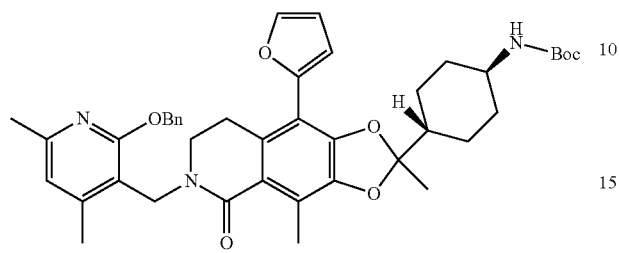

The t-butyl-((trans-4-(9-(furan-2-yl)-2,4-dimethyl-5-oxo-5,6,7,8-tetrahydro-[1,3]dioxolo[4,5-g]isoquinolin-2-yl)cyclohexyl)carbamate synthesized in [Step 9] above (180 mg, 0.373 mmol) was added to N,N-dimethylformamide (1.5 mL). The reaction solution was chilled to 0° C., then t-butoxide (0.5 mL, 0.485 mmol) was added dropwise and agitated for 5 minutes. A solution of 2-(benzyloxy)-3-(chloromethyl)4,6-dimethylpyridin (127 mg, 0.485 mmol) synthesized according to the method stated in WO2014097041 dissolved in N, N-dimethylformamide (1.5 mL) was added, followed by 3 hours agitation at 0° C. After the reaction ended, an ammonium chloride solution was added, and extraction was performed using 10% methanol-chloroform. The extracted organic layer was dried using anhydrous sodium sulfate, then distilled under vacuum. The residue was purified using basic silica gel column chromatography to obtain the compound indicated in the title (170 mg).

Step 11. Preparation of 2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one

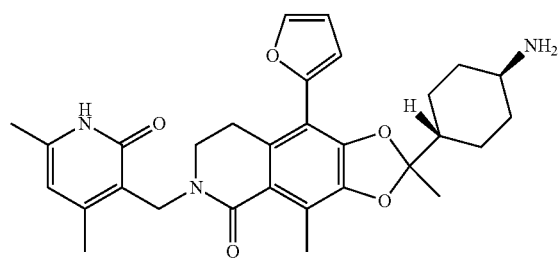 [SMILES: Cc1cc(C)c(CN2CCc3c(c(C)c4c(c3-c3ccco3)OC(C)([C@H]3CC[C@H](N)CC3)O4)C2=O)c(=O)[nH]1]

The t-butyl-(trans-4-(6-((2-(benzyloxy)-4,6-dimethylpyridin-3-yl)methyl)-9-(furan-2-yl)-2,4-dimethyl-5-oxo-5,6,7,8-tetrahydro-[1,3]dioxolo[4,5-g]isoquinolin-2-yl)cyclohexyl)carbamate synthesized in [Step 10] above (170 mg, 0.24 mmol) was dissolved in dichloromethane (2 mL), and trifluoroacetic acid (0.18 mL, 2.4 mmol) was added. The reaction solution was agitated for 11 hours at room temperature. After the reaction ended, saturated sodium bicarbonate water was added to neutralize, and extraction was performed using 20% methanol-chloroform. The extracted organic layer was dried using anhydrous sodium sulfate, then concentrated under vacuum and purified using basic silica gel column chromatography to obtain the compound indicated in the title (43 mg).

Step 12. Preparation of 6-((4,6-dimethyl-2-oxo-1,2-dihydropyridin-3-yl)methyl)-2-trans-4-(dimethylamino)cyclohexyl-9-(furan-2-yl)-2,4-dimethyl-7,8-dihydro-[1,3]dioxolo[4,5-g]isoquinolin-5(6H)-one

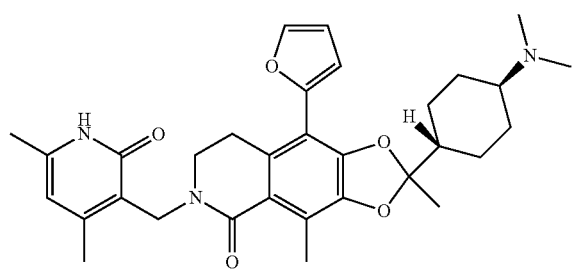

The 2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one synthesized in [Step 11] above (40 mg, 0.077 mmol) and 37% formaldehyde aqueous solution (25 uL, 0.231 mmol) were added in sequence to methanol (0.8 mL), then agitated for 30 minutes at room temperature. Sodium triacetoxyborohydride (81 mg, 0.385 mmol) was added followed by 12 hours agitation at room temperature. After the reaction ended, saturated sodium bicarbonate water was added to neutralize, and extraction was performed using 20% methanol-chloroform. The extracted organic layer was washed with salt water, dried with anhydrous sodium sulfate, then vacuum distilled. The residue was purified using basic silica gel column chromatography to obtain the compound indicated in the title (33 mg).

Step 13. Preparation of (R)-6-((4,6-dimethyl-2-oxo-1,2-dihydropyridin-3-yl)methyl)-2-trans-4-(dimethylamino)cyclohexyl-9-(furan-2-yl)-2,4-dimethyl-7,8-dihydro-[1,3]dioxolo[4,5-g]isoquinolin-5(6H)-one [Compound 30] and (S)-6-((4,6-dimethyl-2-oxo-1,2-dihydropyridin-3-yl)methyl)-2-trans-4-(dimethylamino)cyclohexyl-9-(furan-2-yl)-2,4-dimethyl-7,8-dihydro-[1,3]dioxolo[4,5-g]isoquinolin-5(6H)-one [Compound 31]

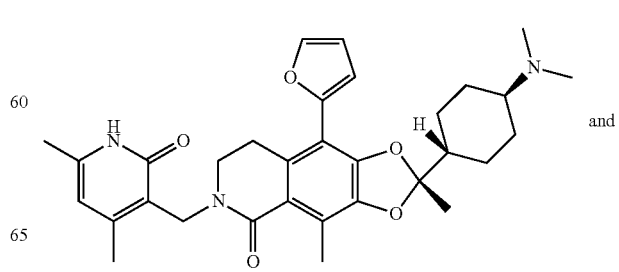

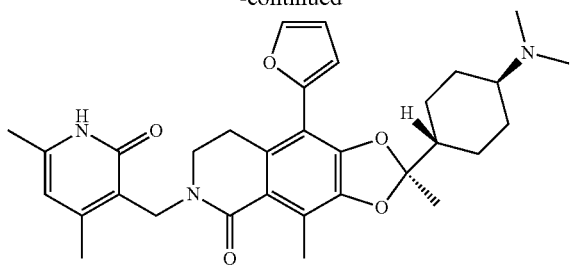

The 6-((4,6-dimethyl-2-oxo-1,2-dihydropyridin-3-yl)methyl)-2-trans-4-(dimethylamino)cyclohexyl-9-(furan-2-yl)-2,4-dimethyl-7,8-dihydro-[1,3]dioxolo[4,5-g]isoquinolin-5(6H)-one synthesized in [Step 12] was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 18 minutes (specific optical rotation $[α]^{20}_D$: −39.81 (C=0.5, methanol:dichloromethane) [Compound 30]
$2^{nd}$ peak: 24 minutes (specific optical rotation $[α]^{20}_D$: +39.57 (C=0.5, methanol:dichloromethane) [Compound 31]

[Synthesis Example 25] Preparation of (R)-6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one [Compound 32] and (S)-6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one [Compound 33]

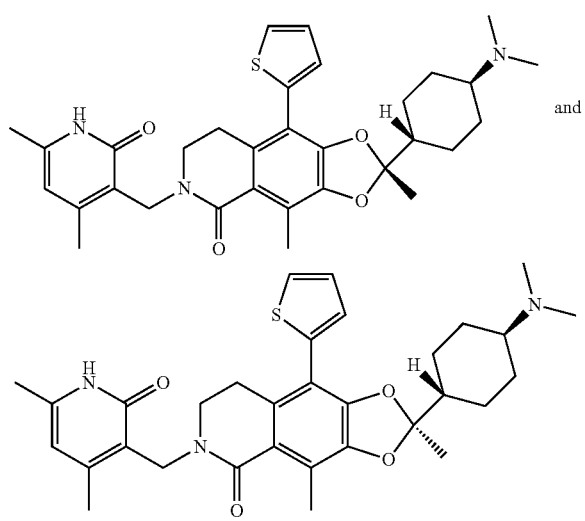

The same reactions as [Synthesis Example 24] were carried out, except that thiophen-2-boronic acid was used instead of furan-2-boronic acid in [Step 9] of [Synthesis Example 24], to obtain synthesized 6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one (53 mg).

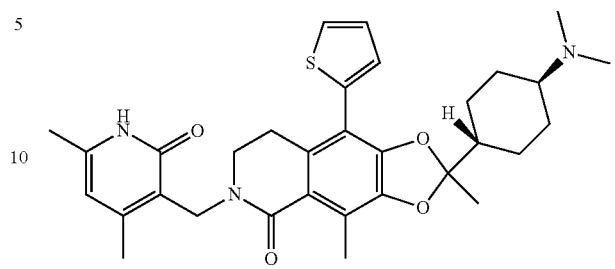

The 6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 18 minutes [Compound 32]
$2^{nd}$ peak: 24 minutes [Compound 33]

[Synthesis Example 26] (R)-6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one [Compound 34] and (S)-6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one [Compound 35]

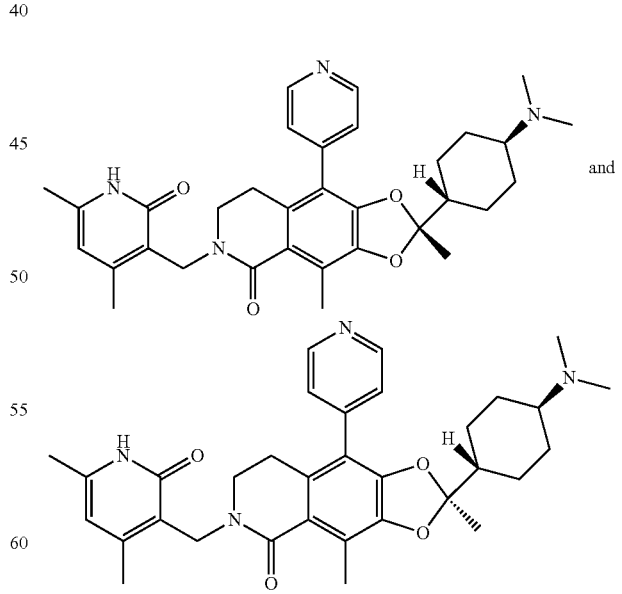

The same reactions as [Synthesis Example 24] were carried out, except that pyridin-4-boronic acid was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one (55 mg).

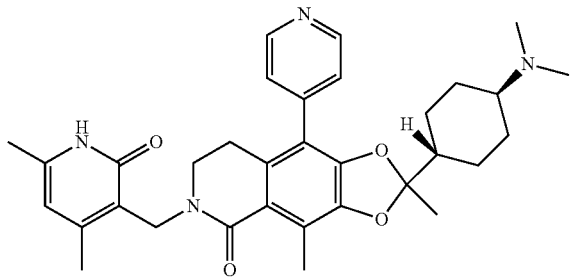

The 6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 22 minutes [Compound 34]
$2^{nd}$ peak: 35 minutes [Compound 35]

[Synthesis Example 27] (R)-6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one [Compound 36] and (S)-6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-on [Compound 37]

The same reactions as [Synthesis Example 24] were carried out, except that 6-fluoropyridin-3-boronic acid was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one (36 mg).

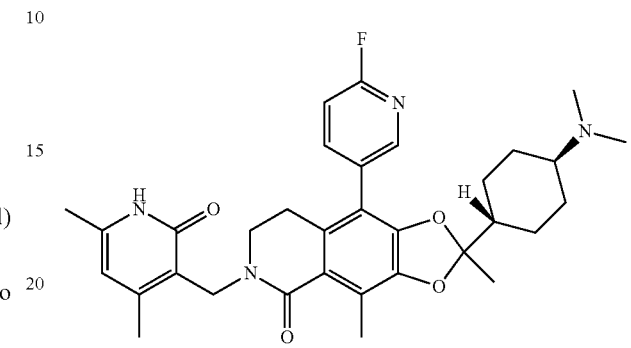

The 6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one synthesized above was separated into isomers under the following conditions.

Column: Daicel Chiralcel OZ-H, 10×250 mm

Temperature: 40° C.

Flow rate: 1.8 mL/min

Wavelength: 270 nm

Elution solvent: ethanol:n-hexane:diethylamine=800:200:0.2 (v/v %)

$1^{st}$ peak: 22 minutes [Compound 36]

$2^{nd}$ peak: 35 minutes [Compound 37]

[Synthesis Example 28] (R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-on [Compound 38] and (S)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one [Compound 39]

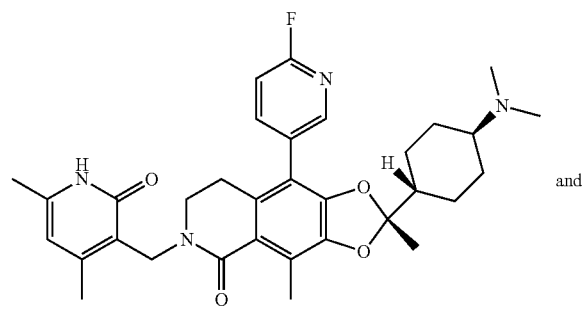

and

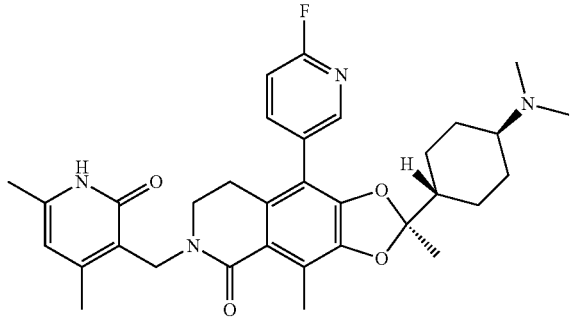

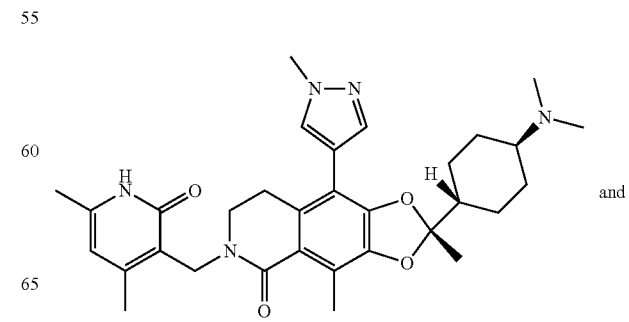

and

-continued

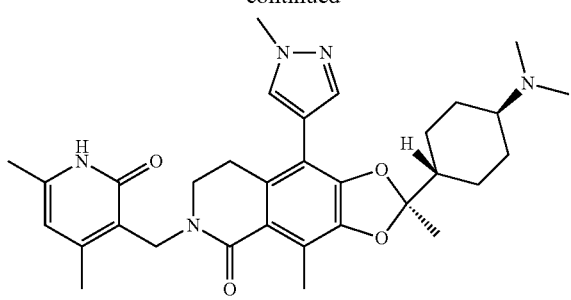

The same reactions as [Synthesis Example 24] were carried out, except that 1-methylpyrazol-4-boronic acid pinacol ester was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one (68 mg).

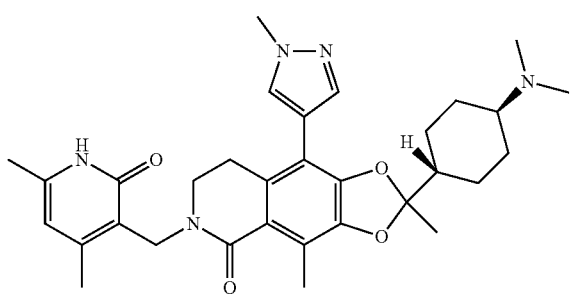

The 6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one synthesized above was separated into isomers under the following conditions.

Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 26 minutes [Compound 38]
$2^{nd}$ peak: 38 minutes [Compound 39]

[Synthesis Example 29] (R)-6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one [Compound 40] and (S)-6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one [Compound 41]

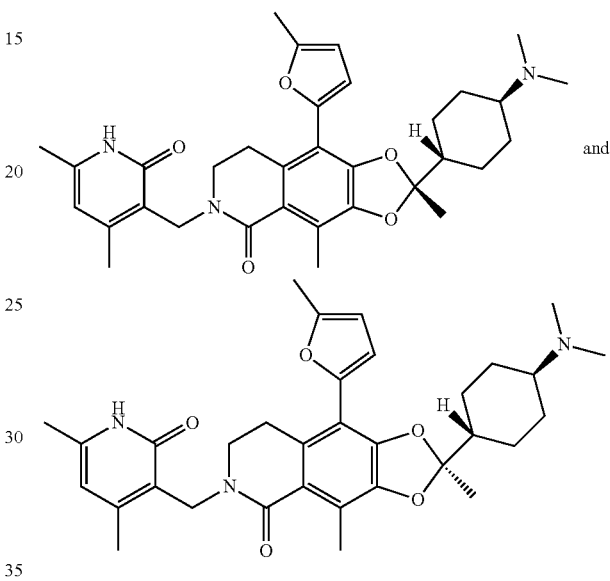

and

The same reactions as [Synthesis Example 24] were carried out, except that 5-methylfuran-2-boronic acid pinacol ester was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one (48 mg).

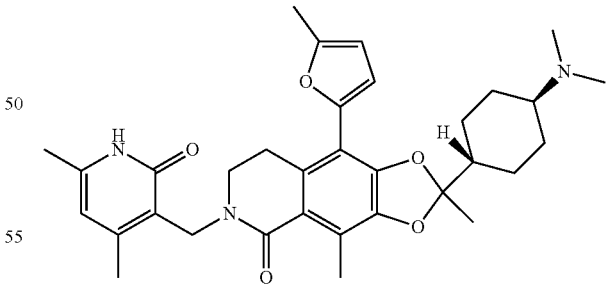

The 6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm Elution solvent: ethanol:n-hexane:diethylamine=800:200: 0.2 (v/v %)
1st peak: 19 minutes [Compound 40]
2nd peak: 24 minutes [Compound 41]

[Synthesis Example 30] (R)-6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one [Compound 42] and (S)-6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one [Compound 43]

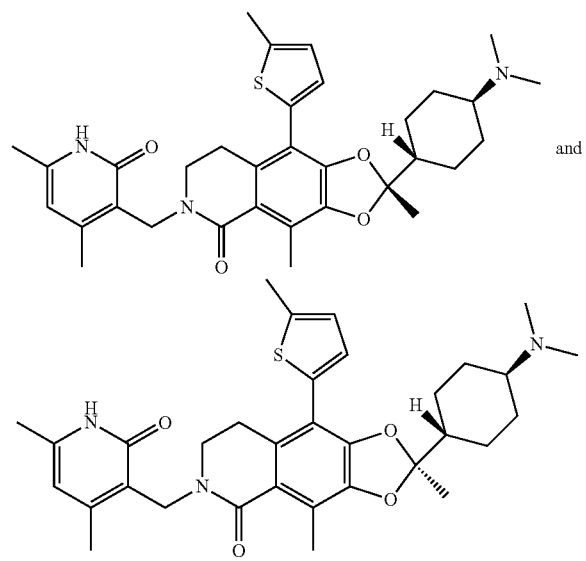

The same reactions as [Synthesis Example 24] were carried out, except that 5-methylthiophen-2-boronic acid pinacol ester was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one (49 mg).

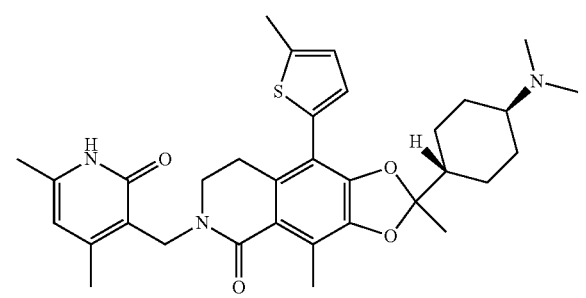

The 6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one synthesized above was separated into isomers under the following conditions.

Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200: 0.2 (v/v %)
1st peak: 19 minutes [Compound 42]
2nd peak: 24 minutes [Compound 43]

[Synthesis Example 31] (R)-6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one [Compound 44] and (S)-6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one [Compound 45]

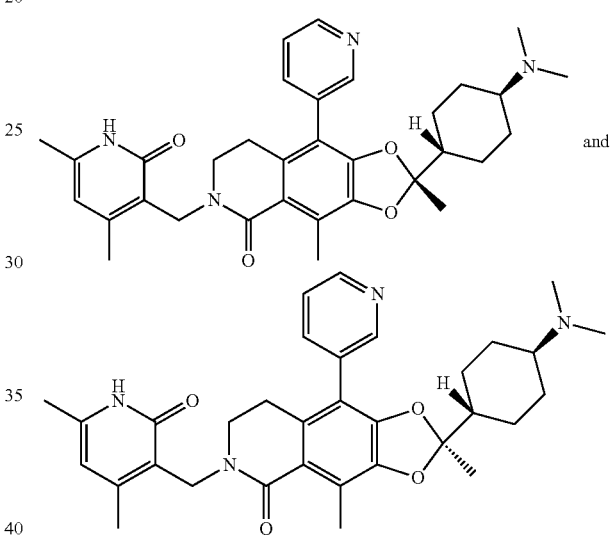

The same reactions as [Synthesis Example 24] were carried out, except that pyridin-3-boronic acid was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one (49 mg).

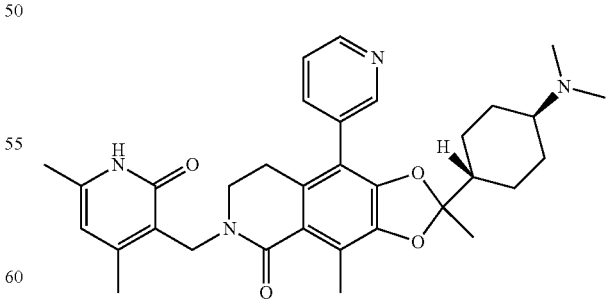

The 6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one synthesized above was separated into isomers under the following conditions.

Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 22 minutes [Compound 44]
$2^{nd}$ peak: 35 minutes [Compound 45]

[Synthesis Example 32] (R)-6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one [Compound 46] and (S)-6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one [Compound 47]

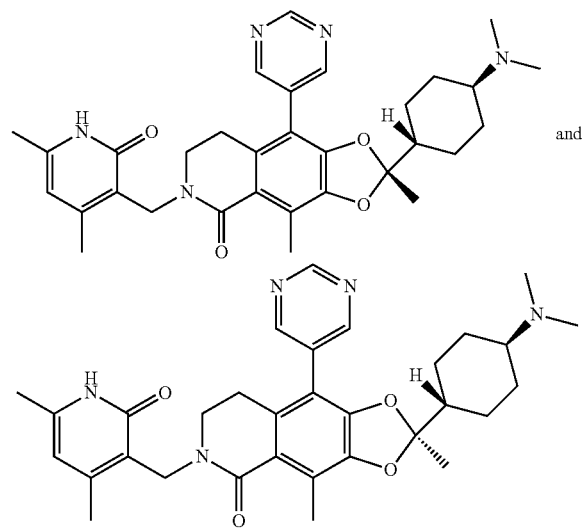

and

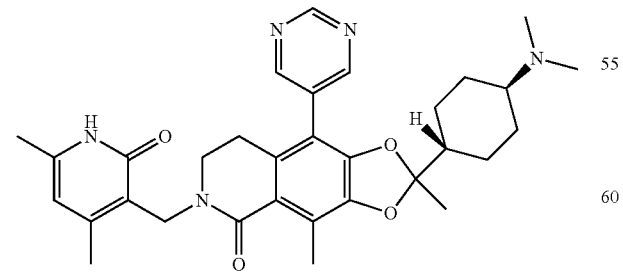

The same reactions as [Synthesis Example 24] were carried out, except that pyrimidin-5-boronic acid was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one (58 mg).

The 6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g] isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 28 minutes [Compound 46]
$2^{nd}$ peak: 35 minutes [Compound 47]

[Synthesis Example 33] (R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one [Compound 48] and (S)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5 (6H)-one [Compound 49]

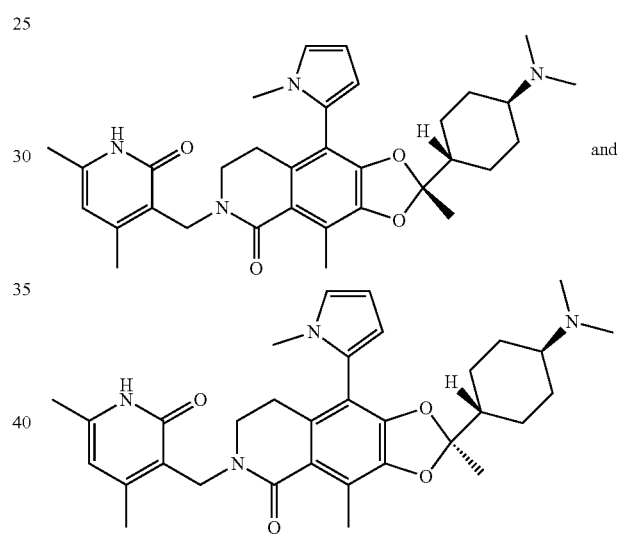

and

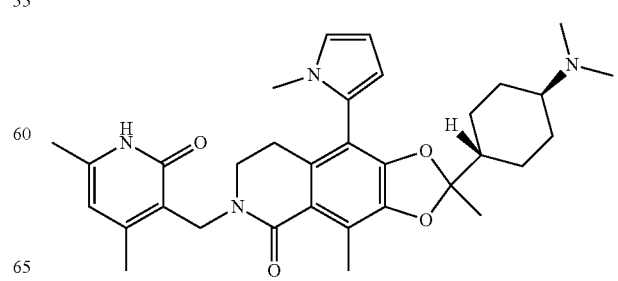

The same reactions as [Synthesis Example 24] were carried out, except that N-methylpyrrol-2-boronic acid pinacol ester was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one (9 mg).

The 6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200: 0.2 (v/v %)
$1^{st}$ peak: 25 minutes [Compound 48]
$2^{nd}$ peak: 36 minutes [Compound 49]

[Synthesis Example 34] (R)-6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one [Compound 50] and (S)-6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one [Compound 51]

The 6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200: 0.2 (v/v %)
$1^{st}$ peak: 18 minutes [Compound 50]
$2^{nd}$ peak: 24 minutes [Compound 51]

[Synthesis Example 35] (R)-6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one [Compound 52] and (S)-6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one [Compound 53]

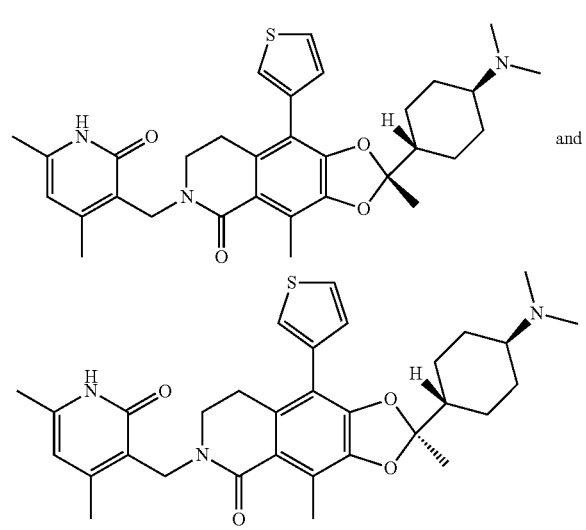
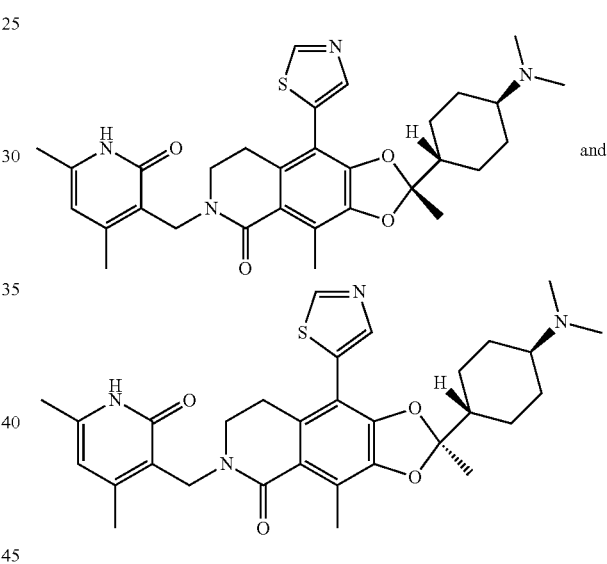

The same reactions as [Synthesis Example 24] were carried out, except that thiophen-3-boronic acid was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one (66 mg).

The same reactions as [Synthesis Example 24] were carried out, except that 5-(tetramethyl-1,3-2-dioxyborolan-2-yl)-1,3-thiazol was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one (7 mg).

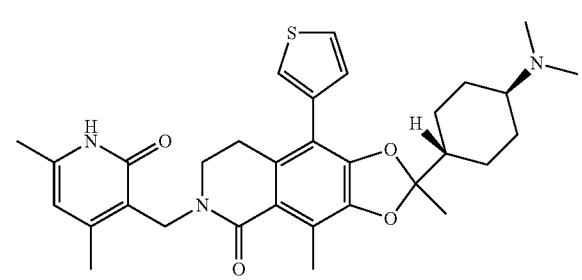
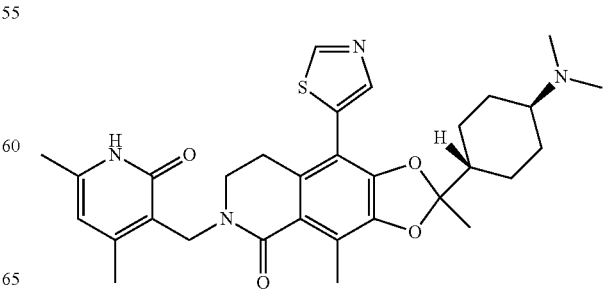

The 6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 26 minutes [Compound 52]
$2^{nd}$ peak: 38 minutes [Compound 53]

[Synthesis Example 36] (R)-6-((4,6-dimethyl-2-oxo-1,2-dihydropyridin-3-yl)methyl)-2-(trans-4-(dimethylamino)cyclohexyl)-9-(1H-Imidazol-1-yl)-2,4-dimethyl-7,8-dihydro-[1,3]dioxolo[4,5-g]isoquinolin-5(6H)-one [Compound 54] and (S)-6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one [Compound 55]

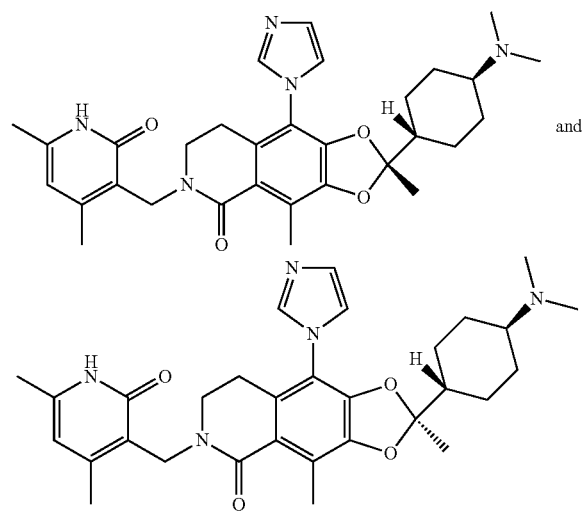
and

The t-butyl-((trans-4-(9-bromo-2,4-dimethyl-5-oxo-5,6,7,8-tetrahydro-[1,3]dioxolo[4,5-g]isoquinolin-2-yl)cyclohexyl)carbamate synthesized in [Step 8] of [Synthesis Example 24] (0.7 g, 1.125 mmol), iron(II)acetylacetonate (44 mg, 0.125 mmol), copper acetate hydrate (25 mg, 0.125 mmol), potassium carbonate (346 mg, 2.506 mmol) and imidazol (1.28 g, 1.879 mmol) were added in sequence to N,N-dimethylacetamide (7 mL). After nitrogen gas substitution, the mixture was refluxed for 13 hours at 80° C. The reaction solution was chilled to room temperature, and filtered through a celite layer. The residue obtained by vacuum distilling the filtrate was purified using basic silica gel column chromatography to obtain t-butyl-((trans-4-(9-(1H-imidazol-1-yl)-2,4-dimethyl-5-oxo-5,6,7,8-tetrahydro-[1,3]dioxolo[4,5-g]isoquinolin-2-yl)cyclohexyl)carbamate (100 mg).

Using the t-butyl-((trans-4-(9-(1H-imidazol-1-yl)-2,4-dimethyl-5-oxo-5,6,7,8-tetrahydro-[1,3]dioxolo[4,5-g]isoquinolin-2-yl)cyclohexyl)carbamate synthesized above, the method of [Step 10] onwards in [Synthesis Example 24] was carried out to obtain 6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one (10 mg).

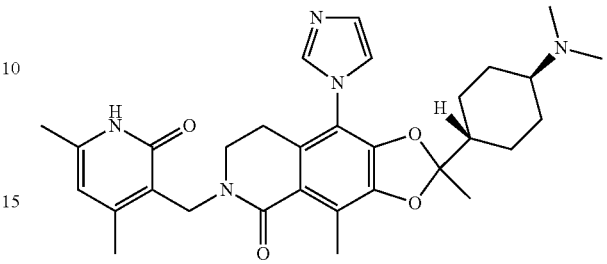

The 6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one synthesized was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
$1^{st}$ peak: 28 minutes [Compound 54]
$2^{nd}$ peak: 40 minutes [Compound 55]

[Synthesis Example 37] (R)-6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one [Compound 56] and (S)-6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one [Compound 57]

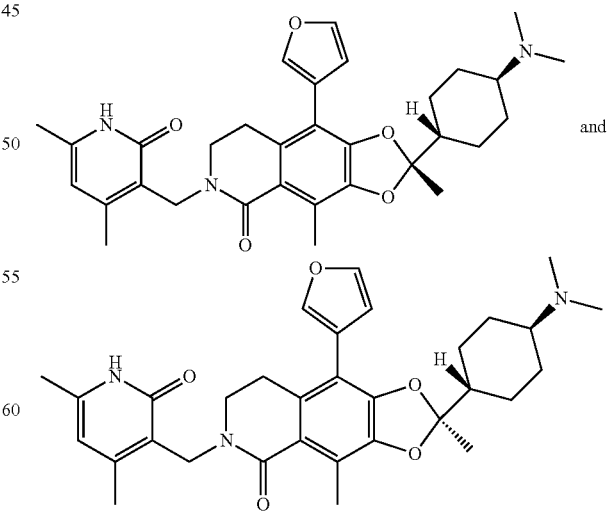

The same reactions as [Synthesis Example 24] were carried out, except that furan-3-boronic acid was used instead of furan-2-boronic acid in [Step 9] of [Synthesis Example 24], to obtain 6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one (50 mg).

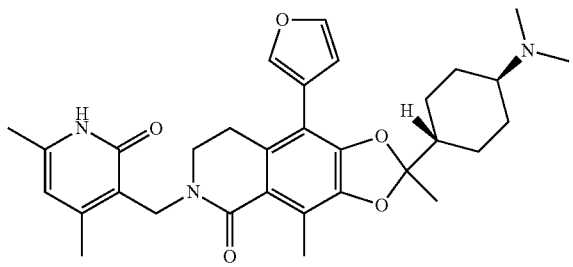

The 6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200: 0.2 (v/v %)
$1^{st}$ peak: 18 minutes [Compound 56]
$2^{nd}$ peak: 24 minutes [Compound 57]

[Synthesis Example 38] (R)-2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one [Compound 58] and (S)-2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one [Compound 59]

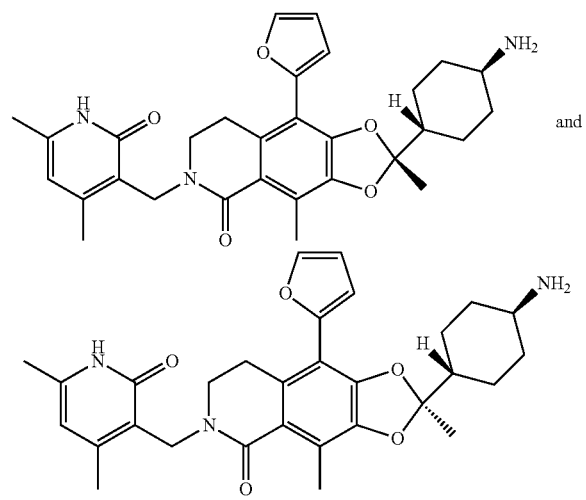

The 2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one synthesized in [Step 11] of [Synthesis Example 24] was separated into isomers under the following conditions. The absolute stereochemistry of the respective isomers was not measured.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200: 0.2 (v/v %)
$1^{st}$ peak: 24 minutes [Compound 58]
$2^{nd}$ peak: 37 minutes [Compound 59]

[Synthesis Example 39] (R)-6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one [Compound 60] and (S)-6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one [Compound 61]

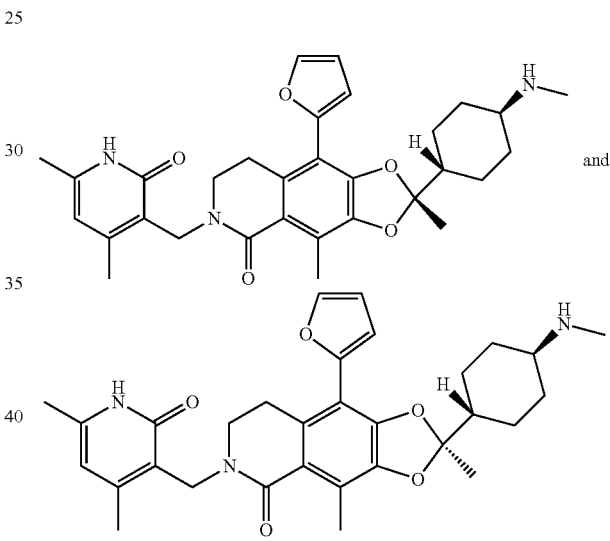

The reactions of up to [Step 11] of [Synthesis Example 24] were carried out, except that in [Step 7] of [Synthesis Example 24], t-butyl(trans-4-ethynylcyclohexyl)(methyl)carbamate was used instead of t-butyl(trans-4-ethynylcyclohexyl)carbamate, to obtain 6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one (250 mg).

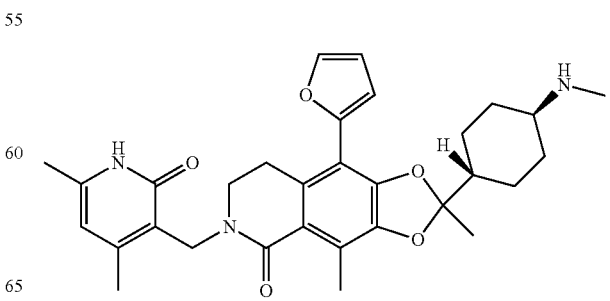

The 6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one synthesized above was separated into isomers under the following conditions.
Column: Daicel Chiralcel OZ-H, 10×250 mm
Temperature: 40° C.
Flow rate: 1.8 mL/min
Wavelength: 270 nm
Elution solvent: ethanol:n-hexane:diethylamine=800:200:0.2 (v/v %)
1$^{st}$ peak: 18 minutes [Compound 60]
2$^{nd}$ peak: 24 minutes [Compound 61]

[Synthesis Example 40] (S)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 62] and (R)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 63]

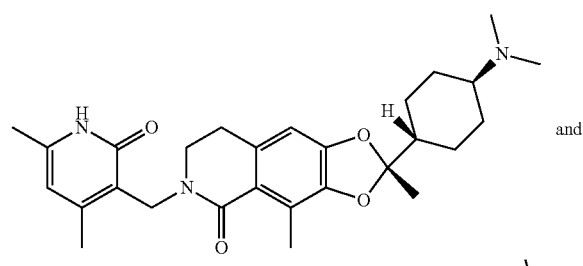
and
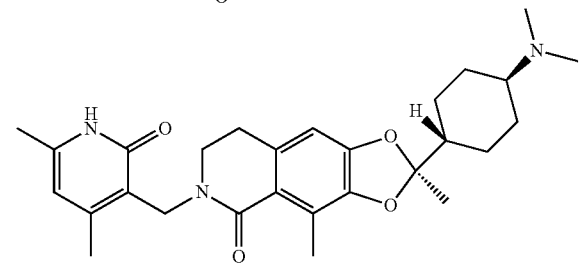

The same reactions as [Synthesis Example 24] were carried out, excluding [Step 8] and [Step 9] of [Synthesis Example 24], to obtain 6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one (50 mg).

The 6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one synthesized above was separated into isomers under the following conditions.

Column: Daicel Chiralcel OZ-H, 10×250 mm

Temperature: 40° C.

Flow rate: 1.8 mL/min

Wavelength: 270 nm

Elution solvent: ethanol:n-hexane:diethylamine=800:200:0.2 (v/v %)

1$^{st}$ peak: 18 minutes [Compound 62]

2$^{nd}$ peak: 24 minutes [Compound 63]

TABLE 4

| Compound No. | Structure $^1$H-NMR spectrum (300 MHz) | Nomenclature | MS[M + H]$^+$ |
|---|---|---|---|
| 30 | | (R)-6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one | 546.3 |

$^1$H-NMR spectrum (300 MHz, CDCl$_3$) δ 12.84 (brs, 1H), 7.45 (s, 1H) 6.60 (d, 1H), 6.48 (d, 1H), 5.91 (s, 1H), 4.80 (s, 2H), 3.40 (t, 2H), 2.94-2.89 (m, 2H), 2.54 (s, 3H), 2.29 (d, 3H), 2.26 (s, 9H), 2.13-2.11 (m, 1H), 2.01-1.90 (m, 4H), 1.83-1.76 (m, 1H), 1.59 (s, 3H), 1.32-1.13 (m, 4H).

TABLE 4-continued

| Compound No. | Structure / ¹H-NMR spectrum (300 MHz) | Nomenclature | MS[M + H]⁺ |
|---|---|---|---|
| 31 | ¹H-NMR spectrum (300 MHz, CDCl₃) δ 12.84 (brs, 1H), 7.45 (s, 1H) 6.60 (d, 1H), 6.48 (d, 1H), 5.91 (s, 1H), 4.80 (s, 2H), 3.40 (t, 2H), 2.94-2.89 (m, 2H), 2.54 (s, 3H), 2.29 (d, 3H), 2.26 (s, 9H), 2.13-2.11 (m, 1H), 2.01-1.90 (m, 4H), 1.83-1.76 (m, 1H), 1.59 (s, 3H), 1.32-1.13 (m, 4H). | (S)-6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one | 546.3 |
| 32 | ¹H-NMR spectrum (300 MHz, CDCl₃) δ 11.89 (brs, 1H), 7.36 (d, 1H), 7.07 (t, 1H), 6.99 (d, 1H), 5.89 (s, 1H), 4.78 (d, 2H), 3.39 (t, 2H), 2.74 (t, 2H), 2.55 (s, 3H), 2.30 (s, 3H), 2.27 (s, 6H), 2.24 (s, 3H), 2.19 (t, 1H), 2.15-1.96 (m, 4H), 1.82 (t, 1H), 1.57 (s, 3H), 1.31-1.14 (m, 4H). | (R)-6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one | 562.3 |
| 33 | ¹H-NMR spectrum (300 MHz, CDCl₃) δ 11.89 (brs, 1H), 7.36 (d, 1H), 7.07 (t, 1H), 6.99 (d, 1H), 5.89 (s, 1H), 4.78 (d, 2H), 3.39 (t, 2H), 2.74 (t, 2H), 2.55 (s, 3H), 2.30 (s, 3H), 2.27 (s, 6H), 2.24 (s, 3H), 2.19 (t, 1H), 2.15-1.96 (m, 4H), 1.82 (t, 1H), 1.57 (s, 3H), 1.31-1.14 (m, 4H). | (S)-6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one | 562.3 |
| 34 | ¹H-NMR spectrum (300 MHz, CDCl₃) δ 11.72 (brs, 1H), 8.64 (s, 2H), 7.20 (s, 2H), 5.89 (s, 1H), 4.76 (d, 2H), 3.38 (t, 2H), 2.60 (t, 2H), 2.56 (s, 3H), 2.31 (s, 3H), 2.31 (s, 6H), 2.22 (s, 3H), 2.21 (t, 1H), 2.01-1.97 (m, 4H), 1.78 (t, 1H), 1.56 (s, 3H), 1.26-1.18 (m, 4H). | (R)-6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one | 557.3 |

TABLE 4-continued

| Compound No. | Structure / ¹H-NMR spectrum (300 MHz) | Nomenclature | MS[M + H]⁺ |
|---|---|---|---|
| 35 | ¹H-NMR spectrum (300 MHz, CDCl₃) δ 11.72 (brs, 1H), 8.64 (s, 2H) 7.20 (s, 2H), 5.89 (s, 1H), 4.76 (d, 2H), 3.38 (t, 2H), 2.60 (t, 2H), 2.56 (s, 3H), 2.31 (s, 3H), 2.31 (s, 6H), 2.22 (s, 3H), 2.21 (t, 1H), 2.01-1.97 (m, 4H), 1.78 (t, 1H), 1.56 (s, 3H), 1.26-1.18 (m, 4H). | (S)-6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one | 557.3 |
| 36 | ¹H-NMR spectrum (300 MHz, CDCl₃) δ 12.59 (brs, 1H), 8.14 (s, 1H), 7.69 (t, 1H), 6.99 (d, 1H), 5.92 (s, 1H), 4.78 (d, 2H), 3.39 (t, 2H), 2.56 (s, 3H), 2.55 (t, 2H), 2.31 (s, 3H), 2.28 (s, 6H), 2.24 (s, 3H), 2.19 (t, 1H), 2.16-1.94 (m, 4H), 1.77 (t, 1H), 1.56 (s, 3H), 1.26-1.18 (m, 4H). | (R)-6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one | 575.3 |
| 37 | ¹H-NMR spectrum (300 MHz, CDCl₃) δ 12.59 (brs, 1H), 8.14 (s, 1H), 7.69 (t, 1H), 6.99 (d, 1H), 5.92 (s, 1H), 4.78 (d, 2H), 3.39 (t, 2H), 2.56 (s, 3H), 2.55 (t, 2H), 2.31 (s, 3H), 2.28 (s, 6H), 2.24 (s, 3H), 2.19 (t, 1H), 2.16-1.94 (m, 4H), 1.77 (t, 1H), 1.56 (s, 3H), 1.26-1.18 (m, 4H). | (S)-6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one | 575.3 |
| 38 | | (R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one | 560.3 |

| Compound No. | Structure<br>¹H-NMR spectrum (300 MHz) | Nomenclature | MS[M + H]⁺ |
|---|---|---|---|
| | ¹H-NMR spectrum (300 MHz, CDCl₃) δ 12.9 (brs, 1H), 7.55 (s, 1H), 7.5 (s, 1H), 5.91 (s, 1H), 4.78 (s, 2H), 3.93 (s, 3H), 3.39 (t, 2H), 2.77 (t, 2H), 2.52 (s, 3H), 2.29 (s, 3H), 2.25 (s, 9H), 2.17-2.11 (m, 1H), 1.97-1.94 (m, 4H), 1.81-1.78 (m, 1H), 1.56 (s, 3H), 1.26-1.17 (m, 4H). | | |
| 39 | | (S)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one | 560.3 |
| | ¹H-NMR spectrum (300 MHz, CDCl₃) δ 12.9 (brs, 1H), 7.55 (s, 1H), 7.5 (s, 1H), 5.91 (s, 1H), 4.78 (s, 2H), 3.93 (s, 3H), 3.39 (t, 2H), 2.77 (t, 2H), 2.52 (s, 3H), 2.29 (s, 3H), 2.25 (s, 9H), 2.17-2.11 (m, 1H), 1.97-1.94 (m, 4H), 1.81-1.78 (m, 1H), 1.56 (s, 3H), 1.26-1.17 (m, 4H). | | |
| 40 | | (R)-6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one | 560.3 |
| | ¹H-NMR spectrum (300 MHz, CDCl₃) δ 11.81 (brs, 1H), 6.51 (d, 1H), 6.07 (d, 1H), 5.92 (s, 1H), 4.79 (d, 2H), 3.41 (t, 2H), 2.95 (t, 2H), 2.53 (s, 3H), 2.32 (s, 3H), 2.31 (s, 3H), 2.27 (s, 9H), 2.15 (t, 1H), 2.12-1.83 (m, 4H), 1.80 (t, 1H), 1.59 (s, 3H), 1.33-1.21 (m, 4H). | | |
| 41 | | (S)-6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one | 560.3 |
| | ¹H-NMR spectrum (300 MHz, CDCl₃) δ 11.81 (brs, 1H), 6.51 (d, 1H) 6.07 (d, 1H), 5.92 (s, 1H), 4.79 (d, 2H), 3.41 (t, 2H), 2.95 (t, 2H), 2.53 (s, 3H), 2.32 (s, 3H), 2.31 (s, 3H), 2.27 (s, 9H), 2.15 (t, 1H), 2.12-1.83 (m, 4H), 1.80 (t, 1H), 1.59 (s, 3H), 1.33-1.21 (m, 4H). | | |
| 42 | | (R)-6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one | 576.3 |

TABLE 4-continued

| Compound No. | Structure / ¹H-NMR spectrum (300 MHz) | Nomenclature | MS[M + H]⁺ |
|---|---|---|---|

¹H-NMR spectrum (300 MHz, CDCl₃) δ 11.25 (brs, 1H), 6.77 (d, 1H) 6.71 (d, 1H), 5.89 (s, 1H), 4.78 (d, 2H), 3.43-3.30 (m, 2H), 2.91-2.69 (m, 2H), 2.54 (s, 3H), 2.49 (s, 3H), 2.30 (s, 3H), 2.28 (s, 6H), 2.23 (s, 3H), 2.21-2.10 (m, 1H), 2.05-1.90 (m, 4H), 1.83-1.76 (m, 1H), 1.57 (s, 3H), 1.32-1.13 (m, 4H).

| 43 | [structure] | (S)-6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one | 576.3 |

¹H-NMR spectrum (300 MHz, CDCl₃) δ 11.25 (brs, 1H), 6.77 (d, 1H) 6.71 (d, 1H), 5.89 (s, 1H), 4.78 (d, 2H), 3.43-3.30 (m, 2H), 2.91-2.69 (m, 2H), 2.54 (s, 3H), 2.49 (s, 3H), 2.30 (s, 3H), 2.28 (s, 6H), 2.23 (s, 3H), 2.21-2.10 (m, 1H), 2.05-1.90 (m, 4H), 1.83-1.76 (m, 1H), 1.57 (s, 3H), 1.32-1.13 (m, 4H).

| 44 | [structure] | (R)-6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one | 557.3 |

¹H-NMR spectrum (300 MHz, CDCl₃) δ 12.06 (brs, 1H), 8.58-8.53 (m, 2H), 7.58 (dt, 1H), 7.33 (dd, 1H), 5.90 (s, 1H), 4.77 (s, 2H), 3.37 (t, 2H), 2.57 (t, 2H), 2.56 (s, 3H), 2.31 (s, 3H), 2.28 (s, 6H), 2.21 (s, 3H), 2.20-2.09 (m, 1H), 2.05-1.87 (m, 4H), 1.83-1.71 (m, 1H), 1.53 (s, 3H), 1.32-1.13 (m, 4H).

| 45 | [structure] | (S)-6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one | 557.3 |

¹H-NMR spectrum (300 MHz, CDCl₃) δ 12.06 (brs, 1H), 8.58-8.53 (m, 2H), 7.58 (dt, 1H), 7.33 (dd, 1H), 5.90 (s, 1H), 4.77 (s, 2H), 3.37 (t, 2H), 2.57 (t, 2H), 2.56 (s, 3H), 2.31 (s, 3H), 2.28 (s, 6H), 2.21 (s, 3H), 2.20-2.09 (m, 1H), 2.05-1.87 (m, 4H), 1.83-1.71 (m, 1H), 1.53 (s, 3H), 1.32-1.13 (m, 4H).

| 46 | [structure] | (R)-6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one | 558.3 |

TABLE 4-continued

| Compound No. | Structure / ¹H-NMR spectrum (300 MHz) | Nomenclature | MS[M + H]⁺ |
|---|---|---|---|
| | ¹H-NMR spectrum (300 MHz, CDCl₃) δ 11.56 (brs, 1H), 9.17 (s, 1H) 8.69 (s, 2H), 5.90 (s, 1H), 4.77 (s, 2H), 3.40 (t, 2H), 2.57 (t, 2H), 2.56 (s, 3H), 2.32 (s, 3H), 2.28 (s, 6H), 2.23 (s, 3H), 2.20-2.09 (m, 1H), 2.05-1.87 (m, 4H), 1.84-1.70 (m, 1H), 1.57 (s, 3H), 1.32-1.15 (m, 4H). | | |
| 47 | [Structure] | (S)-6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one | 558.3 |
| | ¹H-NMR spectrum (300 MHz, CDCl₃) δ 11.56 (brs, 1H), 9.17 (s, 1H) 8.69 (s, 2H), 5.90 (s, 1H), 4.77 (s, 2H), 3.40 (t, 2H), 2.57 (t, 2H), 2.56 (s, 3H), 2.32 (s, 3H), 2.28 (s, 6H), 2.23 (s, 3H), 2.20-2.09 (m, 1H), 2.05-1.87 (m, 4H), 1.84-1.70 (m, 1H), 1.57 (s, 3H), 1.32-1.15 (m, 4H). | | |
| 48 | [Structure] | (R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one | 559.3 |
| | ¹H-NMR spectrum (300 MHz, CDCl₃) δ 12.24 (brs, 1H), 6.69 (d, 1H), 6.17 (dd, 1H), 5.99 (d, 1H), 5.88 (s, 1H), 4.80 (q, 2H), 3.39 (s, 3H), 3.36-3.31 (m, 2H), 2.56 (s, 4H), 2.48-2.43 (m, 1H), 2.25 (dd, 12H) 2.13-2.08 (m, 1H), 1.95-1.93 (m, 4H), 1.76-1.73 (m, 1H), 1.53 (d, 3H), 1.28-1.15 (m, 4H). | | |
| 49 | [Structure] | (S)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one | 559.3 |
| | ¹H-NMR spectrum (300 MHz, CDCl₃) δ 12.24 (brs, 1H), 6.69 (d, 1H), 6.17 (dd, 1H), 5.99 (d, 1H), 5.88 (s, 1H), 4.80 (q, 2H), 3.39 (s, 3H), 3.36-3.31 (m, 2H), 2.56 (s, 4H), 2.48-2.43 (m, 1H), 2.25 (dd, 12H) 2.13-2.08 (m, 1H), 1.95-1.93 (m, 4H), 1.76-1.73 (m, 1H), 1.53 (d, 3H), 1.28-1.15 (m, 4H). | | |
| 50 | [Structure] | (R)-6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one | 562.3 |
| | ¹H-NMR spectrum (300 MHz, CDCl₃) δ 11.44 (brs, 1H), 7.35 (t, 1H) 7.22 (d, 1H), 7.11 (d, 1H), 5.89 (s, 1H), 4.78 (d, 2H), 3.37 (t, 2H), 2.70 (t, 2H), 2.55 (s, 3H), 2.31 (s, 3H), 2.27 (s, 6H), 2.23 (s, 3H), 2.15 (t, 1H), 1.98-1.95 (m, 4H), 1.77 (t, 1H), 1.56 (s, 3H), 1.26-1.23 (m, 4H). | | |

| Compound No. | Structure / ¹H-NMR spectrum (300 MHz) | Nomenclature | MS[M + H]⁺ |
|---|---|---|---|
| 51 | | (S)-6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one | 562.3 |
| | ¹H-NMR spectrum (300 MHz, CDCl₃) δ 11.44 (brs, 1H), 7.35 (t, 1H), 7.22 (d, 1H), 7.11 (d, 1H), 5.89 (s, 1H), 4.78 (d, 2H), 3.37 (t, 2H), 2.70 (t, 2H), 2.55 (s, 3H), 2.31 (s, 3H), 2.27 (s, 6H), 2.23 (s, 3H), 2.15 (t, 1H), 1.98-1.95 (m, 4H), 1.77 (t, 1H), 1.56 (s, 3H), 1.26-1.23 (m, 4H). | | |
| 52 | | (R)-6-((4,6-dimethyl-2-oxo-1,2-dihydropyridin-3-yl)methyl)-2-(trans-4-(dimethylamino)cclohyexl,)-24-dimethyl-9-(thiazol-5-yl)-7,8-dihydro-[1,3]dioxolo[4,5-g]isoquinolin-5(6H)-one | 563.3 |
| | ¹H-NMR spectrum (300 MHz, CDCl₃) δ 11.78 (brs, 1H), 8.85 (s, 1H) 7.81 (s, 1H), 5.91 (s, 1H), 4.77 (s, 2H), 3.44-3.39 (m, 2H), 2.75-2.70 (m, 2H), 2.55 (s, 3H), 2.31 (s, 10H), 2.24-2.19 (m, 3H), 2.01-1.97 (m, 4H), 1.80-1.75 (m, 1H), 1.57 (s, 3H), 1.30-1.15 (m, 4H). | | |
| 53 | | (S)-6-((4,6-dimethyl-2-oxo-1,2-dihydropyridin-3-yl)methyl)-2-(trans-4-(dethylamino)cyclohexyl)-2,4-dimethyl-9-(thiazol-5-yl)-7,8-dihydro-[1,3]dioxolo[4,5-g]isoquinolin-5(6H)-one | 563.3 |
| | ¹H-NMR spectrum (300 MHz, CDCl₃) δ 11.78 (brs, 1H), 8.85 (s, 1H), 7.81 (s, 1H), 5.91 (s, 1H), 4.77 (s, 2H), 3.44-3.39 (m, 2H), 2.75-2.70 (m, 2H), 2.55 (s, 3H), 2.31 (s, 10H), 2.24-2.19 (m, 3H), 2.01-1.97 (m, 4H), 1.80-1.75 (m, 1H), 1.57 (s, 3H), 1.30-1.15 (m, 4H). | | |
| 54 | | (R)-6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one | 546.3 |
| | ¹H-NMR spectrum (300 MHz, CDCl₃) δ 12.37 (brs, 1H), 7.50 (s, 1H) 7.18 (s, 1H), 6.94 (s, 1H), 5.90 (s, 1H), 4.73 (s, 2H), 3.42 (t, 2H), 2.55 (s, 3H), 2.47-2.44 (m, 2H), 2.37 (s, 6H), 2.30 (s, 4H), 2.18-2.16 (m, 3H), 2.10-1.90 (m, 4H), 1.84-1.77 (m, 1H), 1.57 (s, 3H), 1.35-1.16 (m, 4H). | | |

TABLE 4-continued

| Compound No. | Structure / $^1$H-NMR spectrum (300 MHz) | Nomenclature | MS[M + H]$^+$ |
|---|---|---|---|
| 55 | $^1$H-NMR spectrum (300 MHz, CDCl$_3$) δ 12.37 (brs, 1H), 7.50 (s, 1H), 7.18 (s, 1H), 6.94 (s, 1H), 5.90 (s, 1H), 4.73 (s, 2H), 3.42 (t, 2H), 2.55 (s, 3H), 2.47-2.44 (m, 2H), 2.37 (s, 6H), 2.30 (s, 4H), 2.18-2.16 (m, 3H), 2.10-1.90 (m, 4H), 1.84-1.77 (m, 1H), 1.57 (s, 3H), 1.35-1.16 (m, 4H). | (S)-6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one | 546.3 |
| 56 | $^1$H-NMR spectrum (300 MHz, CDCl$_3$) δ 11.79 (brs, 1H), 7.50 (d, 1H), 7.47 (t, 1H), 6.53 (d, 1H), 5.91 (s, 1H), 4.79 (d, 2H), 3.41 (t, 2H), 2.76 (t, 2H), 2.54 (s, 3H), 2.31 (s, 3H), 2.27 (s, 6H), 2.25 (s, 3H), 2.15 (t, 1H), 1.98-1.96 (m, 4H), 1.82 (t, 1H), 1.58 (s, 3H), 1.32-1.24 (m, 4H). | (R)-6-((4,6-dimethyl-2-oxo-1,2-dihydropyridin-3-yl)methyl)-2-(trans-4-(dimethylamino)cyclohex]l)-9-(furan-3-yl)-2,4-dimethyl-7,8-dihydro-[1,3]dioxolo[4,5-g]isoquinolin-5(6H)-one | 546.3 |
| 57 | $^1$H-NMR spectrum (300 MHz, CDCl$_3$) δ 11.79 (brs, 1H), 7.50 (d, 1H), 7.47 (t, 1H), 6.53 (d, 1H), 5.91 (s, 1H), 4.79 (d, 2H), 3.41 (t, 2H), 2.76 (t, 2H), 2.54 (s, 3H), 2.31 (s, 3H), 2.27 (s, 6H), 2.25 (s, 3H), 2.15 (t, 1H), 1.98-1.96 (m, 4H), 1.82 (t, 1H), 1.58 (s, 3H), 1.32-1.24 (m, 4H). | (S)-6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one | 546.3 |
| 58 | $^1$H-NMR spectrum (300 MHz, CDCl$_3$) δ 7.45 (d, 1H), 6.59 (d, 1H), 6.48 (d, 1H), 5.91 (s, 1H), 4.79 (d, 2H), 3.41 (t, 2H), 2.92 (t, 2H), 2.64 (t, 1H), 2.54 (s, 3H), 2.31 (s, 3H), 2.25 (s, 3H), 1.95-1.91 (m, 4H), 1.85 (t, 1H), 1.77 (brs, 2H), 1.59 (s, 3H), 1.34-1.29 (m, 4H). | (R)-2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one | 518.3 |

TABLE 4-continued

| Compound No. | Structure / ¹H-NMR spectrum (300 MHz) | Nomenclature | MS[M + H]⁺ |
|---|---|---|---|
| 59 | | (S)-2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one | 518.3 |
| | ¹H-NMR spectrum (300 MHz, CDCl₃) δ 7.45 (d, 1H), 6.59 (d, 1H), 6.48 (d, 1H), 5.91 (s, 1H), 4.79 (d, 2H), 3.41 (t, 2H), 2.92 (t, 2H), 2.64 (t, 1H), 2.54 (s, 3H), 2.31 (s, 3H), 2.25 (s, 3H), 1.95-1.91 (m, 4H), 1.85 (t, 1H), 1.77 (brs, 2H), 1.59 (s, 3H), 1.34-1.29 (m, 4H). | | |
| 60 | | (R)-6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one | 532.3 |
| | ¹H-NMR spectrum (300 MHz, CDCl₃) δ 7.45 (d, 1H), 6.61 (d, 1H), 6.48 (d, 1H), 5.93 (s, 1H), 4.81 (d, 2H), 3.41 (t, 2H), 2.92 (t, 2H), 2.55 (s, 3H), 2.43 (s, 3H), 2.35 (t, 1H), 2.30 (s, 3H), 2.28 (s, 3H), 1.99 (t, 4H), 1.85 (t, 1H), 1.60 (s, 3H), 1.30 (brs, 1H), 1.29-1.23 (m, 4H). | | |
| 61 | | (S)-6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one | 532.3 |
| | ¹H-NMR spectrum (300 MHz, CDCl₃) δ 7.45 (d, 1H), 6.61 (d, 1H), 6.48 (d, 1H), 5.93 (s, 1H), 4.81 (d, 2H), 3.41 (t, 2H), 2.92 (t, 2H), 2.55 (s, 3H), 2.43 (s, 3H), 2.35 (t, 1H), 2.30 (s, 3H), 2.28 (s, 3H), 1.99 (t, 4H), 1.85 (t, 1H), 1.60 (s, 3H), 1.30 (brs, 1H), 1.29-1.23 (m, 4H). | | |
| 62 | | (S)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 480.3 |
| | ¹H-NMR spectrum (300 MHz, CDCl₃) δ 12.32 (brs, 1H), 6.34 (s, 1H) 5.93 (s, 1H), 4.77 (d, 2H), 3.44 (t, 2H), 3.14 (t, 1H), 2.77 (s, 6H), 2.69 (t, 2H), 2.51 (s, 3H), 2.34 (d, 2H), 2.29 (s, 6H), 2.10 (d, 2H), 1.86 (t, 1H), 1.64 (m, 2H), 1.60 (s, 3H), 1.56-1.53 (m, 2H). | | |

TABLE 4-continued

| Compound No. | Structure $^1$H-NMR spectrum (300 MHz) | Nomenclature | MS[M + H]$^+$ |
|---|---|---|---|
| 63 | | (R)-6-((4,6-dimethyl-2-oxo-1,2-dthydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 480.3 |

$^1$H-NMR spectrum (300 MHz, CDCl$_3$) δ 12.32 (brs, 1H), 6.34 (s, 1H) 5.93 (s, 1H), 4.77 (d, 2H), 3.44 (t, 2H), 3.14 (t, 1H), 2.77 (s, 6H), 2.69 (t, 2H), 2.51 (s, 3H), 2.34 (d, 2H), 2.29 (s, 6H), 2.10 (d, 2H), 1.86 (t, 1H), 1.64 (m, 2H), 1.60 (s, 3H), 1.56-1.53 (m, 2H).

Experimental Example 1: Evaluation of EZH1/EZH2 Methyltransferase Inhibitory Activity The inhibitory activity of the synthesized compounds above against EZH1 or EZH2 methyltransferase was measured. The experiments were consigned to Reaction Biology, and EZH1 or EZH2 activity was measured using a radiometric scintillation proximity assay. To measure the IC$_{50}$ of the synthesized compounds for EZH1 or EZH2, 2.3 nmol/L EZH1 or EZH2, 1 μmol/L histone H3 (21-44)-lys(biotin), 1.5 μmol/L S-adenyl methionine (SAM), and 500 nmol/L $^3$H-SAM were added to the compounds or DMSO with a buffer solution and reacted for 90 minutes at room temperature. The buffer solution was comprised of 50 mmol/L Tris-HCl pH 8.0, 50 mmol/L NaCl, 1 mmol/L EDTA, 1 mmoL/L DTT, 1 mmol/L PMSF and 1% DMSO. Trichloroacetic acid was added to end the reaction, and SPA beads coated with PVT streptavidin were added followed by 1 hour reaction at room temperature. A TopCount NXT plate reader was used to measure the methylation value of the substrate peptide. The measured values were converted to percent activity, setting the mean value for wells treated with DMSO as 100% and the background mean value as 0%. The IC$_{50}$ values were found using the "log(inhibitor) vs. normalized response-variable slope" analysis method of the GraphPad PRISM v6 program.

Experimental Example 2: Cell Growth Inhibition Test

The cell growth inhibition of the synthesized compounds against KARPAS-422 cells was verified. The cultured cell strain was prepared at 1.8×10$^4$ cells/400 μL and placed in a 48-well plate. An RPMI 1640 medium including 20% fetal bovine serum was treated with the test compounds serially diluted to the prescribed concentrations (0.001 to 1000 nM, 1/10 dilution), followed by culturing for 7 days. The CTG method was used to measure the survivability of the cells, and the concentration inhibiting cell growth of the cell strain by 50% (GI$_{50}$) was calculated using GraphPad Prism software.

The results of Experimental Example 1 and Experimental Example 2 are shown in [Table 5] below.

TABLE 5

| Compound No. | Enzyme inhibitory activity (IC$_{50}$, nM) | | Cell growth inhibitory activity (GI$_{50}$, nM) |
|---|---|---|---|
| | EZH1 | EZH2 | KARPAS-422 (EZH2$^{Y641N}$ mutant) |
| 1 | — | — | 10~100 |
| 2 | 15 | 0.36 | 4.5 |
| 3 | — | — | 100~1,000 |
| 4 | — | — | — |
| 5 | 17 | 1.2 | 4.5 |
| 6 | — | — | >1,000 |
| 7 | — | — | — |
| 8 | 167 | 15 | 3.9 |
| 9 | — | — | 100~1,000 |
| 10 | — | — | 4.1~55 |
| 11 | 15 | 0.35 | 3.8~12 |
| 12 | — | — | >1,000 |
| 13 | — | — | 30 |
| 14 | — | — | 45 |
| 15 | — | — | — |
| 16 | — | — | 36 |
| 17 | — | — | — |
| 18 | — | — | 27 |
| 19 | — | — | — |
| 20 | — | — | 47 |
| 21 | — | — | 18 |
| 22 | — | — | 12~19 |
| 23 | 12 | 0.59 | 3.7~6.8 |
| 24 | | | 100~1,000 |
| 25 | | | 14 |
| 26 | | | 46 |
| 27 | | | 9.8 |
| 28 | | | 13 |
| 29 | | | 36 |
| 30 | 8.3~10 | 1.2~1.7 | 3.9~8.4 |
| 31 | | | >1,000 |
| 32 | 12 | 2.5 | 3.4 |
| 33 | | | >1,000 |
| 34 | 32 | 3.4 | 3.7 |
| 35 | | | >1,000 |
| 36 | — | — | 5.8 |
| 37 | | | >1,000 |
| 38 | — | — | 5.8 |
| 39 | | | >1,000 |
| 40 | 22 | 2.2 | 4.4~5.5 |
| 41 | | | >1,000 |
| 42 | — | — | 5.7 |
| 43 | | | >1,000 |
| 44 | 14 | 3.3 | 5.1 |
| 45 | — | | >1,000 |
| 46 | | | 7.0 |
| 47 | | | >1,000 |
| 48 | 20 | 3.3 | 5.5 |
| 49 | — | — | >1,000 |
| 50 | 22 | 3.8 | 4.9 |

TABLE 5-continued

| Compound No. | Enzyme inhibitory activity (IC$_{50}$, nM) | | Cell growth inhibitory activity (GI$_{50}$, nM) |
| --- | --- | --- | --- |
| | EZH1 | EZH2 | KARPAS-422 (EZH2$^{Y641N}$ mutant) |
| 51 | | | >1,000 |
| 52 | 18 | 2.7 | 5.9 |
| 53 | | | >1,000 |
| 54 | | | 28 |
| 55 | | | >1,000 |
| 56 | | | 7.2 |
| 57 | | | >1,000 |
| 58 | | | 28 |
| 59 | | | >1,000 |
| 60 | | | 19 |
| 61 | | | >1,000 |
| 62 | | | |
| 63 | | | |
| Control A | 83~197 | 2.0~2.9 | 19~114 |
| Control B | 17~46 | 0.73~2.0 | 1.3~15 |

Comparative Example

Control A is N-((4,6-dimethyl-2-oxo-1,2-dihydiropyridin-3-yl)methyl)-5-(ethyl(tetrahydro-2H-pyran-4-yl)amino)-4-methyl-4'-(morpholinomethyl)-[1,1'-biphenyl]-3-carboxamide (Tazemetostat). The synthesis of this compound is stated under Embodiment 44 on p. 220 of International Patent Application WO2012/142504, and its structure is as follows:

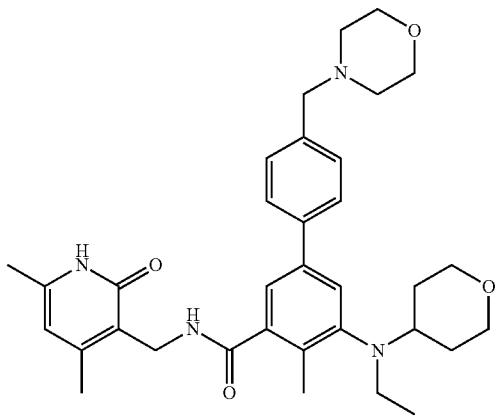 [SMILES: CCN(c1cc(-c2ccc(CN3CCOCC3)cc2)cc(C(=O)NCc2c(C)cc(C)[nH]c2=O)c1C)C1CCOCC1]

Control B is (2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (Valemetostat). The synthesis of this compound is stated under Embodiment 35 on p. 137 of International Patent Application WO2014/141616, and its structure is as follows

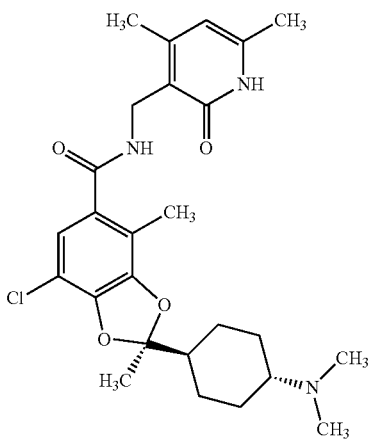 [SMILES: Cc1cc(C)c(CNC(=O)c2cc(Cl)c3c(c2C)O[C@@](C)([C@H]2CC[C@H](N(C)C)CC2)O3)c(=O)[nH]1]

Comparative Experimental Example: EZH1/EZH2 Methyltransferase Inhibitory Activity and Cell Growth Inhibition Experiment Using Hematologic Malignancy Cell Strain Control A [N-((4,6-dimethyl-2-oxo-1,2-dihydiropyridin-3-yl)methyl)-5-(ethyl(tetrahydro-2H-pyran-4-yl)amino)-4-methyl-4'-(morpholinomethyl)-[1,1'-biphenyl]-3-carboxamide (Tazemetostat)] and Control B [(2R)-7-chloro-2-[trans-4-(dimethylamino)cyclohexyl]-N-[(4,6-dimethyl-2-oxo-1,2-dihydropyridin-3-yl)methyl]-2,4-dimethyl-1,3-benzodioxole-5-carboxamide (Valemetostat)] synthesized using the methods stated in the comparative examples were used to carry out EZH1/EZH2 methyltransferase inhibitory activity and hematologic malignancy cell strain growth inhibition experiments using methods identical to those described in Experimental Example 1 and Experimental Example 2.

The results are shown in [Table 5] above.

As seen in [Table 5], the compounds according to the present invention have outstanding EZH1 and/or EZH2 enzyme inhibitory activity compared to the controls, and as a result thereof have outstanding growth inhibitory activity against a hematologic malignancy cell strain.

INDUSTRIAL APPLICABILITY

The present invention relates to novel dioxoisoquinolinone derivative compounds and use thereof. More specifically, the present invention relates to novel dioxoisoquinolinone derivative compounds with inhibition activity of EZH1 (Enhancer of zeste homolog 1) and/or EZH2 (Enhancer of zeste homolog 2) activity, a pharmaceutically acceptable salt thereof, and/or pharmaceutical compositions comprising the same.

What is claimed is:

1. A compound selected from the group consisting of dioxoisoquinolinone derivative compounds of the following Formula 1a, a pharmaceutically acceptable salt, an optical isomer, a hydrate and a solvate thereof:

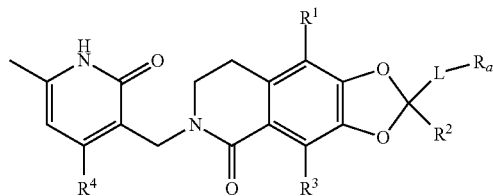

[Formula 1a]

wherein, in Formula 1a,
R¹ is H, halogen, $C_{1-6}$ alkyl, $C_{2-6}$ alkenyl, $C_{2-6}$ alkynyl, $C_{3-6}$ cycloalkyl, $C_{3-6}$ cycloalkenyl, nitrile, aryl, a 5 to 6-membered aromatic heterocyclyl comprising 1 to 3 heteroatoms independently selected from a group comprised of N, O and S, or an aliphatic heterocyclyl including or not including unsaturated bonds in parts of a 5 to 6-membered ring, wherein the ring comprises 1 to 2 heteroatoms selected independently from a group comprised of N, O and S;

The $C_{3-6}$ cycloalkyl, $C_{3-6}$ cycloalkenyl, aryl, or a 5 to 6-membered aromatic heterocyclyl comprising 1 to 3 heteroatoms independently selected from a group comprised of N, O and S, or an aliphatic heterocyclyl including or not including unsaturated bonds in parts of a 5 to 6-membered ring, wherein the ring comprises 1 to 2 heteroatoms selected independently from a group comprised of N, O and S, is substituted or unsubstituted by 1 to 3 selected independently from the following group A;

L is a bond or $C_{1-6}$ alkylene;
$R_a$ is a substituted $C_{5-9}$ bicycloalkyl;
R² is H or $C_{1-6}$ alkyl;
R³ is H, halogen or $C_{1-6}$ alkyl;
R⁴ is $C_{1-6}$ alkyl, $C_{1-6}$ alkoxy or thio-$C_{1-6}$ alkyl;

Group A comprises halogen, $C_{1-6}$ alkyl, $C_{1-6}$ alkoxy, a 5 to 6-membered aliphatic heterocyclyl whose ring comprises 1 to 2 heteroatoms independently selected from a group comprised of N, O and S, wherein the $C_{1-6}$ alkyl, $C_{1-6}$ alkoxy and a 5 to 6-membered aliphatic heterocyclyl are substituted or unsubstituted with 1 to 3 selected independently from the following Group B;

Group B comprises halogen, $C_{1-6}$ alkyl, $C_{1-6}$ alkoxy, a 5 to 6-membered aliphatic heterocyclyl whose ring comprises 1 to 2 heteroatoms independently selected from a group comprised of N, O and S, wherein the $C_{1-6}$ alkyl, $C_{1-6}$ alkoxy and a 5 to 6-membered aliphatic heterocyclyl are substituted or unsubstituted with 1 to 3 selected independently from the following Group C; and, Group C is halogen, $C_{1-6}$ alkyl, or a 5 to 6-membered aliphatic heterocyclyl whose ring comprises 1 to 2 heteroatoms independently selected from a group comprised of N, O and S.

2. The compound of claim 1, wherein
$R_a$ is a substituted bicyclo[2.2.2]octyl.

3. The compound of claim 2, wherein
the substituted bicyclo[2.2.2]octyl is substituted by NR⁵R⁶, where the R⁵ and R⁶ are, respectively and independently, H or $C_{1-6}$ alkyl.

4. The compound of claim 1, wherein
R¹ is H, halogen, $C_{1-3}$ alkyl, $C_{2-3}$ alkenyl, $C_{2-3}$ alkynyl, $C_{3-5}$ cycloalkyl or $C_{3-5}$ cycloalkenyl.

5. The compound of claim 1, wherein
R² is methyl.

6. The compound of claim 1, wherein
R³ is methyl or halogen.

7. The compound of claim 1, wherein
R⁴ is methyl, propyl, methoxy or thiomethyl.

8. The compound of claim 1, wherein the compound of Formula 1a is selected from the group consisting of the following compounds:

9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer A;

9-chloro-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer B;

9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one;

9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one isomer A;

9-chloro-2-(4-(dimethylamino)bicyclo[2.2.2]octan-1-yl)-6-((4-methoxy-6-methyl-2-oxo-1,2-dihydropyridin-3-yl)methyl)-2,4-dimethyl-7,8-dihydro[1,3]dioxolo[4,5-g]isoquinolin-5(6H)-one isomer B;

9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one;

9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one isomer A;

9-chloro-2-(4-(dimethylamino)bicyclo[2.2.2]octan-1-yl)-2,4-dimethyl-6-((6-methyl-4-(methylthio)-2-oxo-1,2-dihydropyridin-3-yl)methyl)-7,8-dihydro[1,3]dioxolo[4,5-g]isoquinolin-5(6H)-one isomer B;

9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one isomer A;

9-bromo-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]iso-quinolin-5(6H)-one isomer B;

9-cyclopropyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-(cyclopent-1-en-1-yl)-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

9-cyclopentyl-6-((4,6-dimethyl-2-oxo-1,2-dihydropyridin-3-yl)methyl)-2-(4-(dimethylamino)bicyclo[2.2.2]octan-1-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4-dimethyl-9-vinyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-9-ethyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4-dimethyl-9-(prop-1-en-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-9-isopropyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-9-ethyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-N g]isoquinolin-5(6H)-one;

6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one isomer A;

6-((4,6-dimethyl-2-oxo-1,2-dihydropyridin-3-yl)methyl)-2-(4-(dimethylamino)bicyclo[2.2.2]octan-1-yl)-2,4,9-trimethyl-7,8-dihydro-[1,3]dioxolo[4,5-g]isoquinolin-5(6H)-one isomer B;

2-(4-(dimethylamino)bicyclo[2.2.2]octan-1-yl)-6-((4-methoxy-6-methyl-2-oxo-1,2-dihydropyridin-3-yl)methyl)-2,4,9-trimethyl-7,8-dihydro[1,3]dioxolo[4,5-g]isoquinolin-5(6H)-one;

2-(4-(dimethylamino)bicyclo[2.2.2]octan-1-yl)-2,4,9-trimethyl-6-((6-methyl-2-oxo-4-propyl-1,2-dihydropyridin-3-yl)methyl)-7,8-dihydro[1,3]dioxolo[4,5-g]isoquinolin-5(6H)-one;

4-chloro-6-((4,6-dimethyl-2-oxo-1,2-dihydropyridin-3-yl)methyl)-2-(4-(dimethylamino)bicyclo[2.2.2]octan-1-yl)-2,9-dimethyl-7,8-dihydro-[1,3]dioxolo[4,5-g]isoquinolin-5(6H)-one;

4,9-dichloro-6-((4,6-dimethyl-2-oxo-1,2-dihydropyridin-3-yl)methyl)-2-(4-(dimethylamino)bicyclo[2.2.2]octan-1-yl)-2-methyl-7,8-dihydro-[1,3]dioxolo[4,5-g]isoquinolin-5(6H)-one; and 9-chloro-6-((4,6-dimethyl-2-oxo-1,2-dihydropyridin-3-yl)methyl)-2-(4-(dimethylamino)bicyclo[2.2.2]octan-1-yl)-4-methyl-7,8-dihydro-[1,3]dioxolo[4,5-g]isoquinolin-5(6H)-one.

9. A compound selected from the group consisting of dioxoisoquinolinone derivative compounds, a pharmaceutically acceptable salt, an optical isomer, a hydrate and a solvate thereof, wherein the dioxoisoquinolinone derivative compound is selected from the group consisting of:

(R)-6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-N (dimethylamino)cyclohexyl)-2,4-dimethyl-9-(thiophen-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one;

(R)-6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one;

(R)-2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one; and (R)-6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one.

10. A compound selected from the group consisting of dioxoisoquinolinone derivative compounds selected from the group consisting of the following compounds, a pharmaceutically acceptable salt, an optical isomer, a hydrate and a solvate thereof:

6-((4,6-dimethyl-2-oxo-1,2-dihydropyridin-3-yl)methyl)-2-(trans-4-(dimethylamino)cyclohexyl)-2,4-dimethyl-9-(thiophen-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(pyridin-4-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-(6-fluoropyridin-3-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(5-methylfuran-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(5-methylthiophen-2-yl)-7,8-dihydro-N [1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(pyrimidin-5-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrrol-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(thiophen-3-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-(1H-imidazol-1-yl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-(furan-3-yl)-2,4-dimethyl-7,8-dihydro-[1,3]dioxolo[4,5-g]isoquinolin-5(6H)-one;

2-(trans-4-aminocyclohexyl)-6-((4,6-dimethyl-2-oxo-1,2-dihydropyridin-3-yl)methyl)-9-(furan-2-yl)-2,4-dimethyl-7,8-dihydro-[1,3]dioxolo[4,5-g]isoquinolin-5(6H)-one; and, 6-((4,6-dimethyl-2-oxo-1,2-dihydropyridin-3-yl)methyl)-9-(furan-2-yl)-2,4-dimethyl-2-(trans-4-(methylamino)cyclohexyl)-7,8-dihydro-[1,3]dioxolo[4,5-g]isoquinolin-5(6H)-one.

11. A pharmaceutical composition comprising the compound of any one of claims 8 to 10 or a pharmaceutically acceptable salt thereof and one or more members selected from the group consisting of a pharmaceutically acceptable carrier, an adjuvant and a vehicle.

12. The pharmaceutical composition of claim 11, which has a form of a tablet, a pill, a powder, a capsule, a syrup or an emulsion.

13. Use of the compound according to any one of claims 8 to 10, or a pharmaceutically acceptable salt thereof, or the pharmaceutical composition of claim 11 or claim 12, for the treatment of cancers or tumors associated with EZH1 and/or EZH2.

14. Use of the compound according to any one of claims 8 to 10, or a pharmaceutically acceptable salt thereof, or the pharmaceutical composition of claim 11 or claim 12, in the manufacture of a medicament for the treatment of cancers or tumors associated with EZH1 and/or EZH2.

15. A method of treating cancers or tumors associated with EZH1 and/or EZH2 comprising administering an effective amount of the compound according to any one of claims 8 to 10, or a pharmaceutically acceptable salt thereof, or the pharmaceutical composition of claim 11 or claim 12, to a subject in need thereof.

\* \* \* \* \*